United States Patent
Cortez, Jr. et al.

(10) Patent No.: US 12,369,905 B2
(45) Date of Patent: Jul. 29, 2025

(54) CLOSING TISSUE OPENINGS

(71) Applicant: EDWARDS LIFESCIENCES CORPORATION, Irvine, CA (US)

(72) Inventors: Felino V. Cortez, Jr., Bowie, MD (US); Luke Anthony Zanetti, Parkton, MD (US); Sai Prasad Uppalapati, Plano, TX (US); John Richard Carpenter, Santa Ana, CA (US); Stephen Cournane, Severn, MD (US); Stephen Epstein, Millersville, MD (US); Ashley Nicolette Hinga, Eldersburg, MD (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 336 days.

(21) Appl. No.: 18/181,514

(22) Filed: Mar. 9, 2023

(65) Prior Publication Data
US 2023/0210523 A1     Jul. 6, 2023

Related U.S. Application Data

(63) Continuation of application No. PCT/US2021/049358, filed on Sep. 8, 2021.
(Continued)

(51) Int. Cl.
*A61B 17/04* (2006.01)
*A61B 17/062* (2006.01)

(52) U.S. Cl.
CPC ........ *A61B 17/0469* (2013.01); *A61B 17/062* (2013.01); *A61B 2017/0472* (2013.01)

(58) Field of Classification Search
CPC .............. A61B 17/0469; A61B 17/062; A61B 2017/0472
See application file for complete search history.

(56) References Cited

U.S. PATENT DOCUMENTS

| 3,131,957 A | 5/1964 | Musto |
| 3,752,516 A | 8/1973 | Mumma |

(Continued)

FOREIGN PATENT DOCUMENTS

| EP | 0791330 A3 | 11/1997 |
| EP | 3505077 A1 | 7/2019 |

(Continued)

OTHER PUBLICATIONS

Alfieri, 0. el al., "The double-orifice technique in mitral valve repair: a +A198:A225simple solution for complex problems," (2001) J. Thorne. Cardiovasc. Surg., 122(4):674-681.
(Continued)

*Primary Examiner* — Phong Son H Dang
(74) *Attorney, Agent, or Firm* — Chang & Hale

(57) ABSTRACT

A suture system can comprise a first and a second curved double arm needle, and a needle docking device configured to maintain the first and the second curved double arm needles in alignment with and parallel to one another and at predetermined orientations relative to the needle docking device. The system can include a needle manipulating instrument having a distal portion configured to engage the first and the second curved double arm needles while the first and second curved double arm needles are in the needle docking device, and to maintain the needles in predetermined orientations.

17 Claims, 43 Drawing Sheets

Related U.S. Application Data

(60) Provisional application No. 63/076,891, filed on Sep. 10, 2020.

(56) References Cited

U.S. PATENT DOCUMENTS

| | | | |
|---|---|---|---|
| 4,403,797 A | 9/1983 | Ragland, Jr. | |
| 4,662,376 A | 5/1987 | Belanger | |
| 4,807,625 A | 2/1989 | Singleton | |
| 5,144,961 A | 9/1992 | Chen et al. | |
| 5,147,316 A | 9/1992 | Castillenti | |
| 5,312,423 A | 5/1994 | Rosenbluth et al. | |
| 5,391,176 A | 2/1995 | de la Torre | |
| 5,405,352 A | 4/1995 | Weston | |
| 5,454,821 A | 10/1995 | Harm et al. | |
| 5,472,446 A | 12/1995 | de la Torre | |
| 5,507,754 A | 4/1996 | Green et al. | |
| 5,527,323 A | 6/1996 | Jervis et al. | |
| 5,554,184 A | 9/1996 | Machiraju | |
| 5,626,614 A | 5/1997 | Hart | |
| 5,643,293 A | 7/1997 | Kogasaka et al. | |
| 5,681,331 A | 10/1997 | de la Torre et al. | |
| 5,716,368 A | 2/1998 | de la Torre et al. | |
| 5,727,569 A | 3/1998 | Benetti et al. | |
| 5,728,109 A | 3/1998 | Schulze et al. | |
| 5,746,752 A | 5/1998 | Burkhart | |
| 5,769,862 A | 6/1998 | Kammerer et al. | |
| 5,797,928 A | 8/1998 | Kogasaka | |
| 5,824,065 A | 10/1998 | Gross | |
| 5,860,992 A * | 1/1999 | Daniel | A61B 17/0491 |
| | | | 606/139 |
| 5,931,868 A | 8/1999 | Gross | |
| 5,957,936 A | 9/1999 | Yoon et al. | |
| 5,971,447 A | 10/1999 | Steck, III | |
| 6,010,531 A | 1/2000 | Donlon et al. | |
| 6,074,417 A | 6/2000 | Peredo | |
| RE36,974 E * | 11/2000 | Bonutti | A61B 17/0401 |
| | | | 606/232 |
| 6,269,819 B1 | 8/2001 | Oz et al. | |
| 6,332,893 B1 | 12/2001 | Mortier et al. | |
| 6,562,051 B1 | 5/2003 | Bolduc et al. | |
| 6,626,930 B1 | 9/2003 | Allen et al. | |
| 6,629,534 B1 | 10/2003 | St. Goar et al. | |
| 6,752,810 B1 | 6/2004 | Gao et al. | |
| 6,840,246 B2 | 1/2005 | Downing | |
| 6,921,408 B2 | 7/2005 | Sauer | |
| 6,940,246 B2 | 9/2005 | Mochizuki et al. | |
| 6,978,176 B2 | 12/2005 | Lattouf | |
| 6,991,635 B2 | 1/2006 | Takamoto et al. | |
| 6,997,950 B2 | 2/2006 | Chawla | |
| 7,112,207 B2 | 9/2006 | Allen et al. | |
| 7,291,168 B2 | 11/2007 | Macoviak et al. | |
| 7,294,148 B2 | 11/2007 | McCarthy | |
| 7,309,086 B2 | 12/2007 | Carrier | |
| 7,316,706 B2 | 1/2008 | Bloom et al. | |
| 7,373,207 B2 | 5/2008 | Lattouf | |
| 7,431,692 B2 | 10/2008 | Zollinger et al. | |
| 7,513,908 B2 | 4/2009 | Lattouf | |
| 7,534,260 B2 | 5/2009 | Lattouf | |
| 7,608,091 B2 | 10/2009 | Goldfarb et al. | |
| 7,618,449 B2 | 11/2009 | Tremulis et al. | |
| 7,632,308 B2 | 12/2009 | Loulmet | |
| 7,635,386 B1 | 12/2009 | Gammie | |
| 7,666,196 B1 | 2/2010 | Miles | |
| 7,744,609 B2 | 6/2010 | Allen et al. | |
| 7,837,727 B2 | 11/2010 | Goetz et al. | |
| 7,871,368 B2 | 1/2011 | Zollinger et al. | |
| 7,871,433 B2 | 1/2011 | Lattouf | |
| 7,959,650 B2 | 6/2011 | Kaiser et al. | |
| 8,029,518 B2 | 10/2011 | Goldfarb et al. | |
| 8,029,565 B2 | 10/2011 | Lattouf | |
| 8,043,368 B2 | 10/2011 | Crabtree | |
| 8,147,542 B2 | 4/2012 | Maisano et al. | |
| 8,187,323 B2 | 5/2012 | Mortier et al. | |
| 8,221,438 B2 * | 7/2012 | Ortiz | A61B 17/072 |
| | | | 606/139 |
| 8,226,711 B2 | 7/2012 | Mortier et al. | |
| 8,241,304 B2 | 8/2012 | Bachman | |
| 8,252,050 B2 | 8/2012 | Maisano et al. | |
| 8,292,884 B2 | 10/2012 | Evine et al. | |
| 8,303,622 B2 | 11/2012 | Alkhatib | |
| 8,333,788 B2 | 12/2012 | Maiorino | |
| 8,382,829 B1 | 2/2013 | Call et al. | |
| 8,439,969 B2 | 5/2013 | Gillinov et al. | |
| 8,454,656 B2 | 6/2013 | Tuval | |
| 8,465,500 B2 | 6/2013 | Speziali | |
| 8,475,525 B2 | 7/2013 | Maisano et al. | |
| 8,500,800 B2 | 8/2013 | Maisano et al. | |
| 8,608,758 B2 | 12/2013 | Singhatat et al. | |
| 8,663,278 B2 | 3/2014 | Mabuchi et al. | |
| 8,771,296 B2 | 7/2014 | Nobles et al. | |
| 8,828,053 B2 | 9/2014 | Sengun et al. | |
| 8,852,213 B2 | 10/2014 | Gammie et al. | |
| 8,888,791 B2 | 11/2014 | Jaramillo et al. | |
| 8,940,008 B2 | 1/2015 | Kunis | |
| 9,131,884 B2 | 9/2015 | Holmes et al. | |
| 9,192,287 B2 | 11/2015 | Saadat et al. | |
| 10,542,968 B2 * | 1/2020 | Einarsson | A61B 17/42 |
| 12,258,139 B2 * | 3/2025 | Witalis | B64D 31/06 |
| 2002/0013571 A1 | 1/2002 | Goldfarb et al. | |
| 2003/0023254 A1 | 1/2003 | Chiu | |
| 2003/0094180 A1 | 5/2003 | Benetti | |
| 2003/0105519 A1 | 6/2003 | Fasol et al. | |
| 2003/0120264 A1 | 6/2003 | Lattouf | |
| 2003/0120341 A1 | 6/2003 | Shennib et al. | |
| 2004/0044365 A1 | 3/2004 | Bachman | |
| 2004/0093023 A1 | 5/2004 | Allen et al. | |
| 2004/0199183 A1 | 10/2004 | Oz et al. | |
| 2005/0004667 A1 | 1/2005 | Swinford et al. | |
| 2005/0019735 A1 | 1/2005 | Demas | |
| 2005/0075654 A1 | 4/2005 | Kelleher | |
| 2005/0119735 A1 | 6/2005 | Spence et al. | |
| 2005/0149067 A1 | 7/2005 | Takemoto et al. | |
| 2005/0149093 A1 | 7/2005 | Pokorney | |
| 2005/0154402 A1 | 7/2005 | Sauer et al. | |
| 2005/0216036 A1 | 9/2005 | Nakao | |
| 2005/0216077 A1 | 9/2005 | Mathis et al. | |
| 2005/0261710 A1 | 11/2005 | Sakamoto et al. | |
| 2005/0267493 A1 | 12/2005 | Schreck et al. | |
| 2006/0030866 A1 | 2/2006 | Schreck | |
| 2006/0100698 A1 | 5/2006 | Lattouf | |
| 2006/0111739 A1 | 5/2006 | Staufer et al. | |
| 2006/0167541 A1 | 7/2006 | Lattouf | |
| 2006/0190030 A1 | 8/2006 | To et al. | |
| 2006/0282088 A1 | 12/2006 | Ryan | |
| 2007/0001857 A1 | 1/2007 | Hartmann et al. | |
| 2007/0049952 A1 | 3/2007 | Weiss | |
| 2007/0055292 A1 | 3/2007 | Ortiz et al. | |
| 2007/0112422 A1 | 5/2007 | Dehdashtian | |
| 2007/0112425 A1 | 5/2007 | Schaller et al. | |
| 2007/0118151 A1 | 5/2007 | Davidson | |
| 2007/0118154 A1 | 5/2007 | Crabtree | |
| 2007/0149995 A1 | 6/2007 | Quinn et al. | |
| 2007/0197858 A1 | 8/2007 | Goldfarb et al. | |
| 2007/0213582 A1 | 9/2007 | Zollinger et al. | |
| 2007/0270793 A1 | 11/2007 | Lattouf | |
| 2007/0293876 A1 * | 12/2007 | Abe | A61B 17/0482 |
| | | | 606/144 |
| 2008/0004597 A1 | 1/2008 | Lattouf et al. | |
| 2008/0009888 A1 | 1/2008 | Ewers et al. | |
| 2008/0065203 A1 | 3/2008 | Khalapyan | |
| 2008/0140093 A1 | 6/2008 | Stone et al. | |
| 2008/0167714 A1 | 7/2008 | St. Goar et al. | |
| 2008/0188893 A1 | 8/2008 | Selvitelli et al. | |
| 2008/0195126 A1 | 8/2008 | Solem | |
| 2008/0228223 A1 | 9/2008 | Alkhatib | |
| 2008/0249504 A1 | 10/2008 | Lattouf et al. | |
| 2008/0269781 A1 | 10/2008 | Funamura et al. | |
| 2009/0005863 A1 | 1/2009 | Goetz et al. | |
| 2009/0043153 A1 | 2/2009 | Zollinger et al. | |
| 2009/0105729 A1 | 4/2009 | Zentgraf | |
| 2009/0105751 A1 | 4/2009 | Zentgraf | |
| 2009/0276038 A1 | 11/2009 | Tremulis et al. | |
| 2010/0023056 A1 | 1/2010 | Johansson et al. | |
| 2010/0023117 A1 | 1/2010 | Yoganathan et al. | |

(56) References Cited

U.S. PATENT DOCUMENTS

| | | |
|---|---|---|
| 2010/0023118 A1 | 1/2010 | Medlock et al. |
| 2010/0042147 A1 | 2/2010 | Janovsky et al. |
| 2010/0174297 A1 | 7/2010 | Speziali |
| 2010/0179574 A1 | 7/2010 | Longoria et al. |
| 2010/0210899 A1 | 8/2010 | Schankereli |
| 2010/0298930 A1 | 11/2010 | Orlov |
| 2011/0015476 A1 | 1/2011 | Franco |
| 2011/0022083 A1 | 1/2011 | DiMatteo et al. |
| 2011/0022084 A1 | 1/2011 | Sengun et al. |
| 2011/0028995 A1 | 2/2011 | Miraki et al. |
| 2011/0029071 A1 | 2/2011 | Zlotnick et al. |
| 2011/0060407 A1 | 3/2011 | Ketai et al. |
| 2011/0106106 A1 | 5/2011 | Meier et al. |
| 2011/0144743 A1 | 6/2011 | Lattouf |
| 2011/0264208 A1 | 10/2011 | Duffy et al. |
| 2011/0270278 A1 | 11/2011 | Overes et al. |
| 2011/0288637 A1 | 11/2011 | De Marchena |
| 2011/0307055 A1 | 12/2011 | Goldfarb et al. |
| 2012/0004669 A1 | 1/2012 | Overes et al. |
| 2012/0143215 A1 | 6/2012 | Corrao et al. |
| 2012/0150223 A1 | 6/2012 | Manos et al. |
| 2012/0179184 A1 | 7/2012 | Orlov |
| 2012/0184971 A1 | 7/2012 | Zentgraf et al. |
| 2012/0203072 A1 | 8/2012 | Lattouf et al. |
| 2012/0226294 A1 | 9/2012 | Tuval |
| 2012/0226349 A1 | 9/2012 | Tuval et al. |
| 2013/0018459 A1 | 1/2013 | Maisano et al. |
| 2013/0035757 A1 | 2/2013 | Zentgraf et al. |
| 2013/0253641 A1 | 9/2013 | Lattouf |
| 2013/0282059 A1 | 10/2013 | Ketai et al. |
| 2013/0345749 A1 | 12/2013 | Sullivan et al. |
| 2014/0031926 A1 | 1/2014 | Kudlik et al. |
| 2014/0039607 A1 | 2/2014 | Kovach |
| 2014/0067052 A1 | 3/2014 | Chau et al. |
| 2014/0114404 A1 | 4/2014 | Gammie et al. |
| 2014/0214152 A1 | 7/2014 | Bielefeld |
| 2014/0243968 A1 | 8/2014 | Padala |
| 2014/0364938 A1 | 12/2014 | Longoria et al. |
| 2015/0032127 A1 | 1/2015 | Gammie et al. |
| 2015/0045879 A1 | 2/2015 | Longoria et al. |
| 2019/0175346 A1 | 6/2019 | Schaffner et al. |
| 2020/0155315 A1 | 5/2020 | Zhang et al. |

FOREIGN PATENT DOCUMENTS

| | | |
|---|---|---|
| JP | 2013517110 A | 5/2013 |
| WO | 2004037463 A1 | 5/2004 |
| WO | 2006127509 A2 | 11/2006 |
| WO | 2007100268 A2 | 9/2007 |
| WO | 2007119057 A1 | 10/2007 |
| WO | 2008013869 A2 | 1/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2012137208 A1 | 10/2012 |
| WO | 2013003228 A1 | 1/2013 |
| WO | 2014093861 A1 | 6/2014 |
| WO | 2015020816 A1 | 2/2015 |
| WO | 2016192481 A1 | 12/2016 |

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11

Carpentier, Alain, "Cardiac valve surgery—the 'French coffec-tion'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," ( 1991) J. Thorne. Cardiovasc. Surg., 101 (3 ):495-50 I.

David, T. E. et al., "Replacement of chordae tendineae with Gore-Tex sutures: a ten-year experience," ( 1996) J. Heart Valve Dis., 5( 4 ):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitral valve prolapse," (1997) J. Heal1 Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for detennining proper length of allificial chordae in mitral valve repair," ( 1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcne suture: a finite element study," (1996) J. Card. Surg., 11(2):136-145.

Langer, F. et al., "Ring plus String: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posteromedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *University of Maryland, Bal Tim Ore*, Case No. JPR2016-00208, Decision on Institution of Inter Faries Review,37 CFR §42. I 08, Paper 6, Entered May 24, 2016, 28 pages.

*Neochord, Inc.* v. *University of Maryland, Baltimore*, Case No. IPR2016-00208, Declaration of Dr. Lishan Aklog, dated Nov. 17, 2015, 91 pages.

*Neochord, Inc.* v. *University of Maryland, Baltimore*, Case No. IPR2016-00208, Petition for inter PartesReview of U.S. Pat. No. 7,635,386, dated Nov. 18, 2015, 65 pages.

Nigro, J. J. et al., "Neochordal repair of the posterior mitral leaflet," (2004) J. Thorne. Cardiovasc. Surg., 127 (2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al.—Transapical Approach for Mitral Valve Repair during Insertion of a Left Ventricular Assist Device, Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

(56) References Cited

OTHER PUBLICATIONS

Sarsam, M.A. I., "Simplified technique for determining the length of artificial cl1ordae in milral valve repair," (2002) Ann. Thorac. Surg., 73(5): 1659-1660.
Savage, E. B. et al., Use of mitral valve repair: analysis of contemporary United States experience reported to the society of thoracic surgeons national cardiac database, . . . (2003) Ann. Thorne. Surg., 75:820-825.
Speziali, G. et al., "Coll'ection of Mitral Valve Regurgitation by Off-Pump, Transapical Placement of Artificial Chordae Tendinae, Results of the European TACT Trial," AATS 93rd Annual Meeting 2013, www.aats.org, 26 pages.
Suematsu, Y. et al., "Three-dimensional echo-guided beating heaii surgery without cardiopulmonary bypass: Atrial septa! defect closure in a swine model," (2005) J. Thorne. Cardiovasc. Surg., 130: 1348-1357.
Von Oppell, U. 0. et al., "Chordal replacement for both minimally invasive and conventional mitral valve surgery using promcasurcd Gore-Tex loops," (2000) Ann. Thorne. Surg., 70(6):2166-2168.
Zussa, C. et al., Artificial mitral valve chordae: experimental and clinical experience;—( 1990) Ann. Thorne. Surg., 50 (3):367-373.
Zussa, C. et al., "Seven-year experience with chordal replacement with expanded polytetrafluoroethylene in floppymitral valve," (1994)1. Thorac. Cardiovasc. Surg., 108(1):37-41.
Zussa, C. et al., "Surgical technique for artificial mitral chordae implantation," ( 1991) Journal of Cardiac Surgery, 6(4):432-438.
Zussa, C., "Artificial chordae," (1995) J. Heart Valve Dis., 4(2):S249-S256.

\* cited by examiner

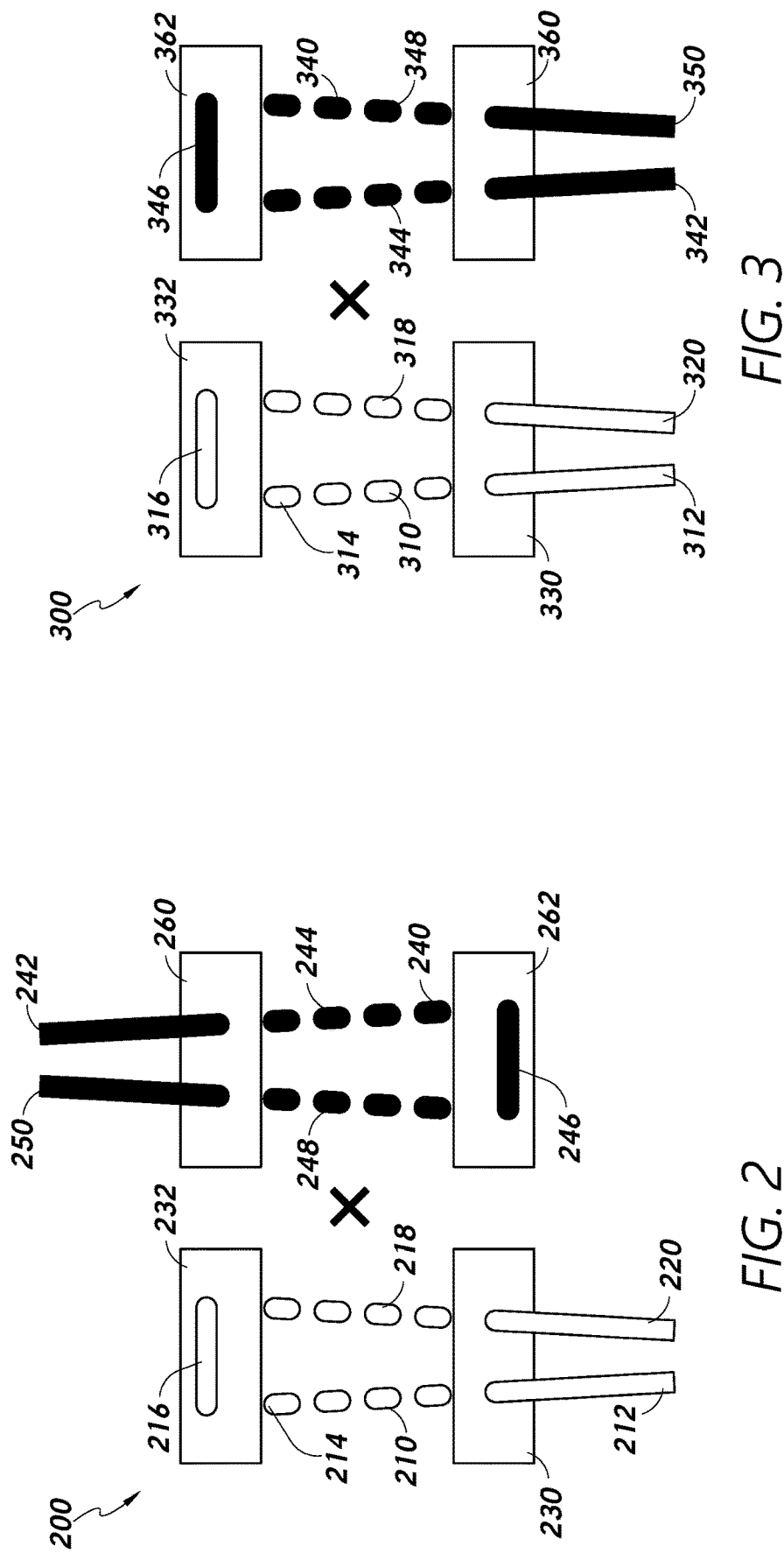

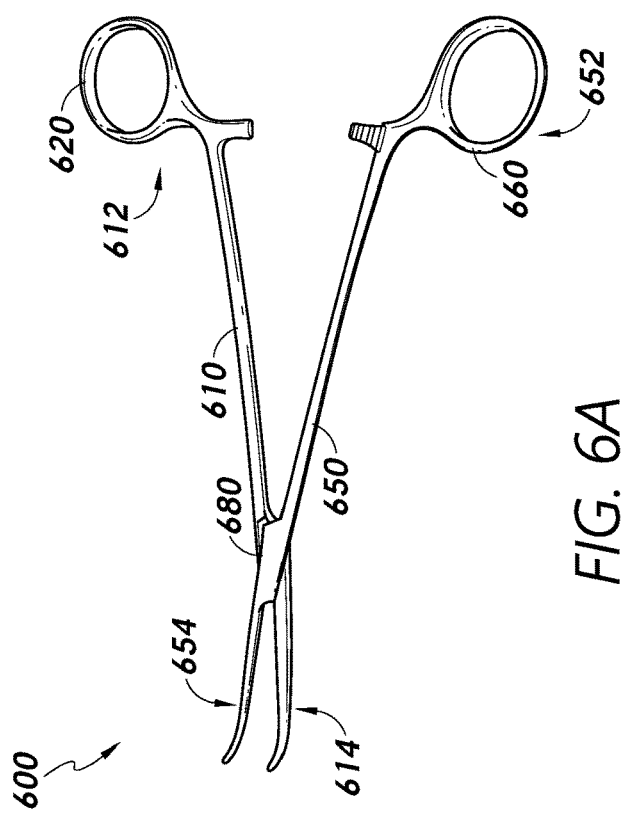
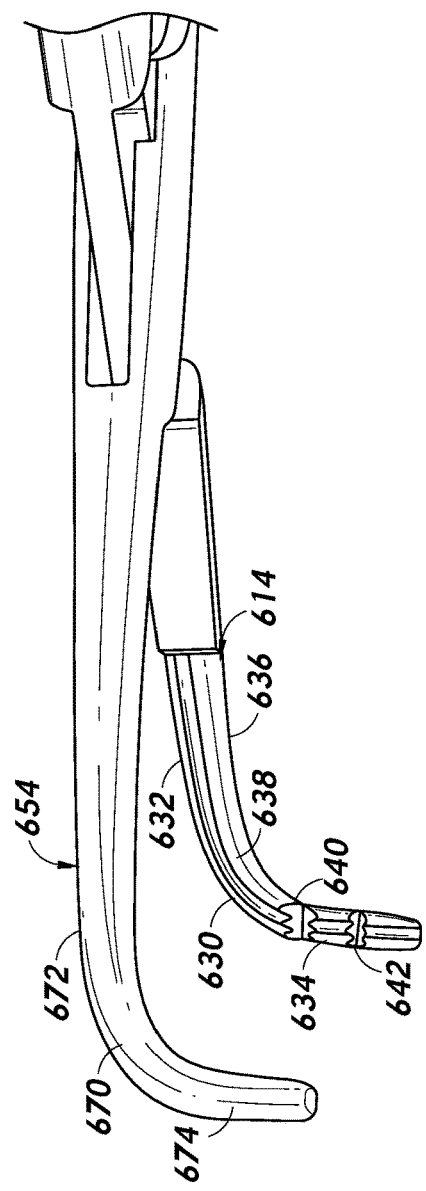
FIG. 6A
FIG. 6B

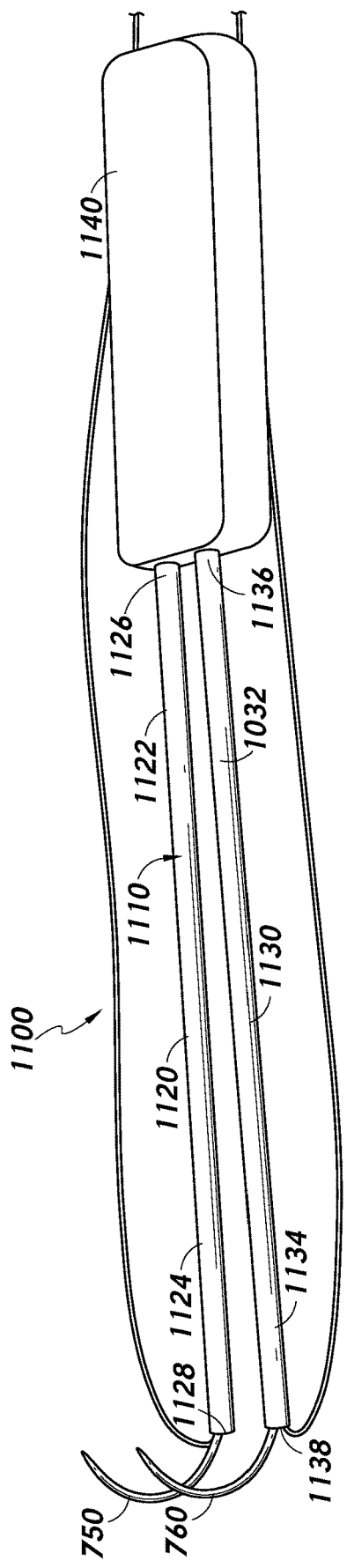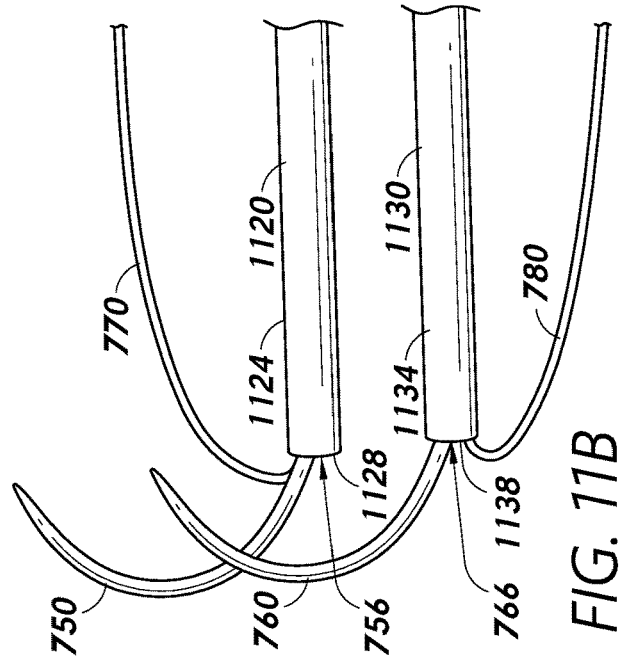
FIG. 11A
FIG. 11B

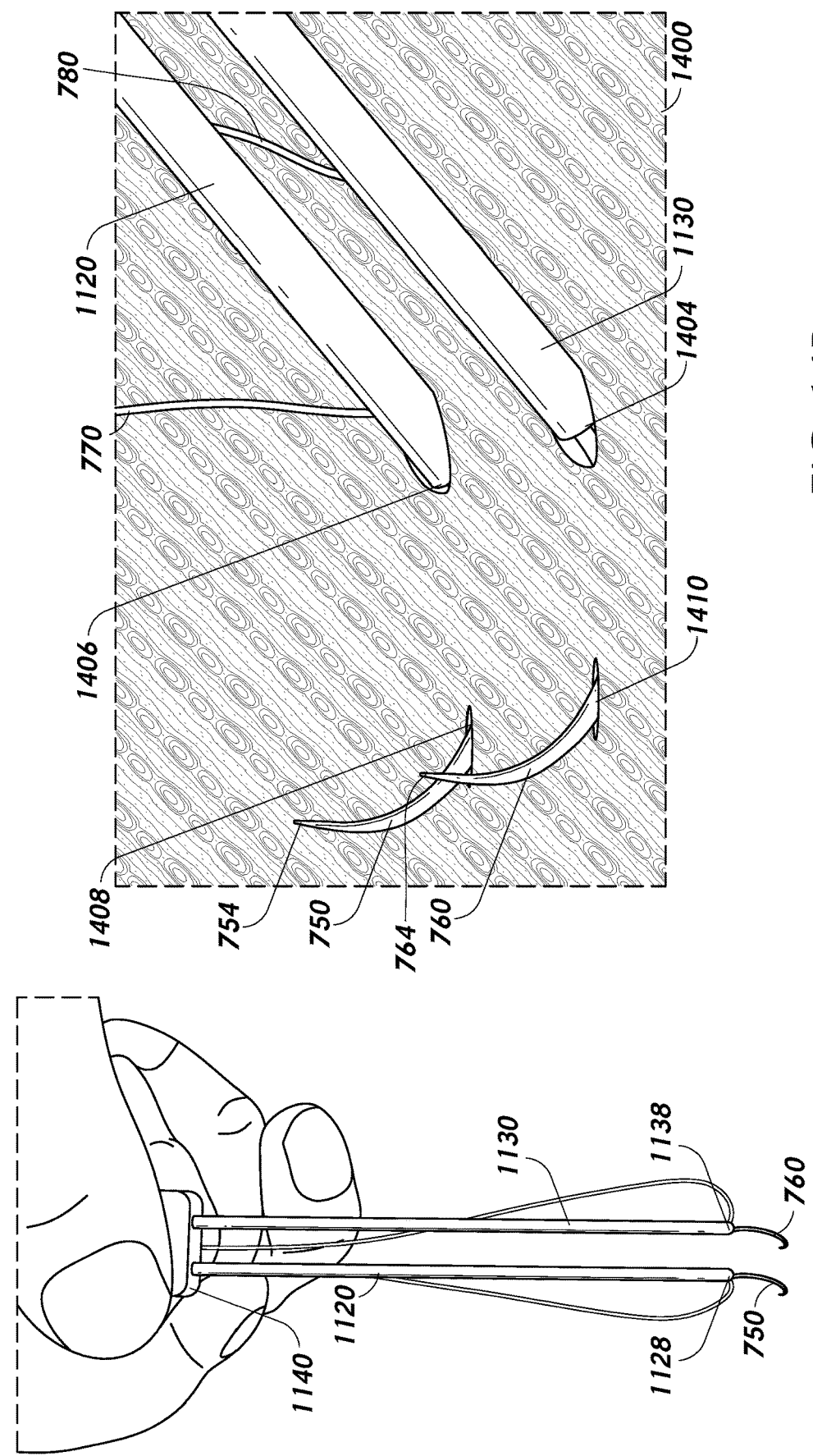

1500

```
┌─────────────────────────────────────────────────────────────┐
│ ENGAGE AND MAINTAIN FIRST PAIR OF CURVED DOUBLE             │ 1502
│ ARM NEEDLES IN ALIGNMENT WITH AND PARALLEL TO               │
│ ONE ANOTHER USING NEEDLE MANIPULATING                       │
│ INSTRUMENT                                                  │
└─────────────────────────────────────────────────────────────┘
                              │
                              ▼
┌─────────────────────────────────────────────────────────────┐
│ INSERT SHARP ENDS OF FIRST PAIR OF CURVED DOUBLE            │ 1504
│ ARM NEEDLES, WHILE FIRST PAIR OF CURVED DOUBLE              │
│ ARM NEEDLES IS HELD BY NEEDLE MANIPULATING                  │
│ INSTRUMENT, INTO TARGET TISSUE IN AREA ADJACENT             │
│ TO OPENING IN TARGET TISSUE TO MAKE FIRST STITCH            │
└─────────────────────────────────────────────────────────────┘
                              │
                              ▼
┌─────────────────────────────────────────────────────────────┐
│ INSERT SHARP ENDS OF ONE OF FIRST PAIR OF CURVED            │ 1506
│ DOUBLE ARM NEEDLES OR SECOND PAIR OF CURVED                 │
│ DOUBLE ARM NEEDLES, WHILE FIRST PAIR OR SECOND              │
│ PAIR OF CURVED DOUBLE ARM NEEDLES IS HELD BY                │
│ NEEDLE MANIPULATING INSTRUMENT, INTO TARGET                 │
│ TISSUE IN AREA ADJACENT TO OPENING TO MAKE                  │
│ SECOND STITCH                                               │
└─────────────────────────────────────────────────────────────┘
                              │
                              ▼
┌─────────────────────────────────────────────────────────────┐
│ TENSION SUTURES OF FIRST STITCH AND SECOND STITCH           │ 1508
│ TO REDUCE SIZE OF OPENING IN TARGET TISSUE                  │
└─────────────────────────────────────────────────────────────┘
```

FIG. 15

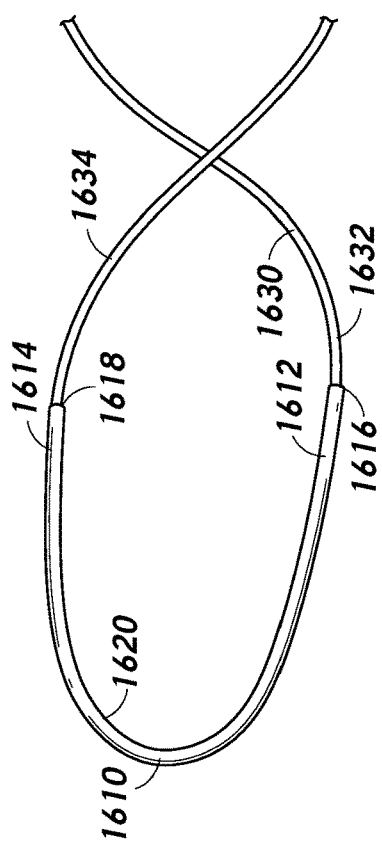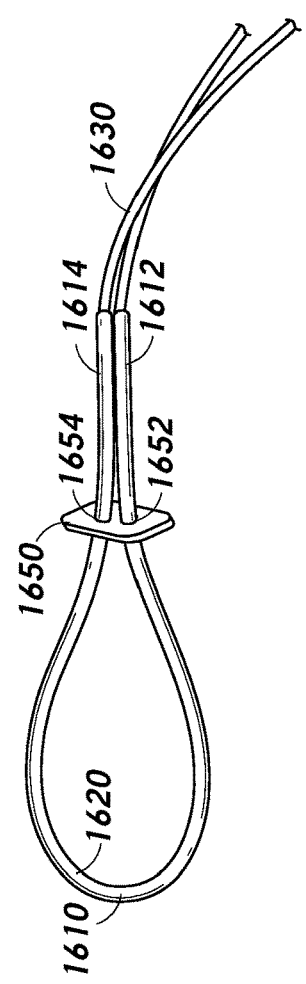
FIG. 19A
FIG. 19B

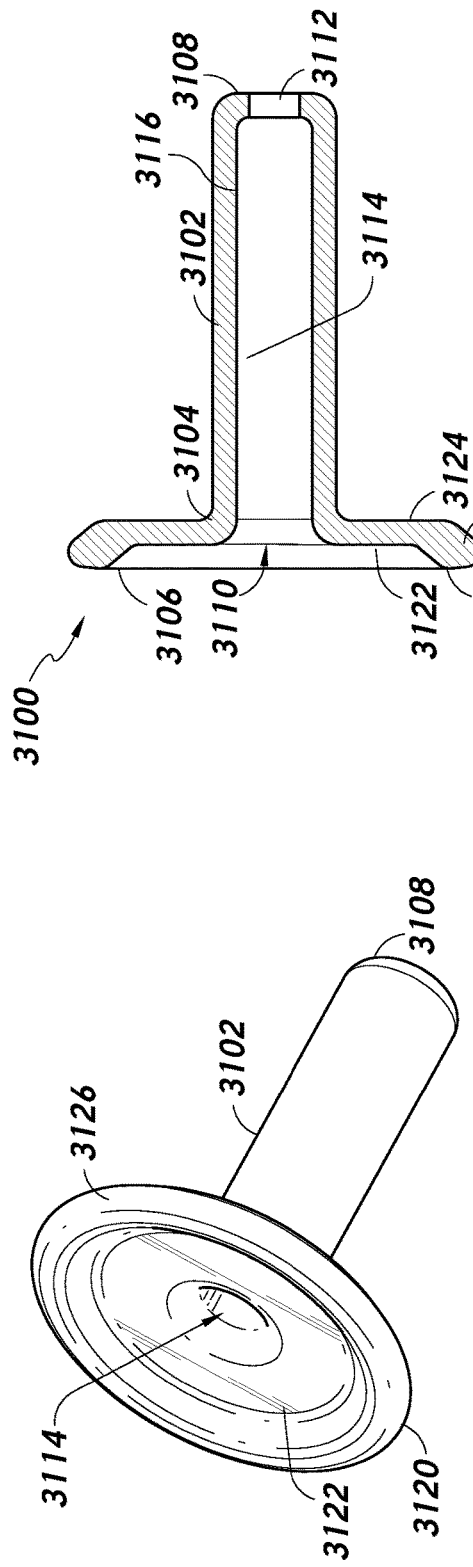
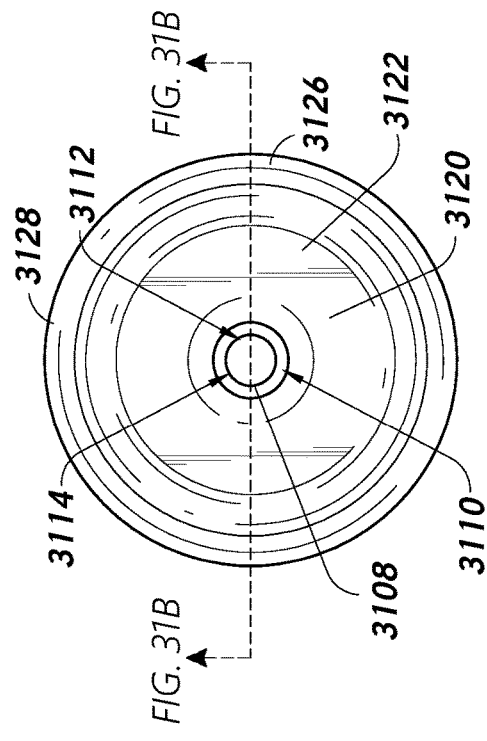
FIG. 31A
FIG. 31B
FIG. 31C

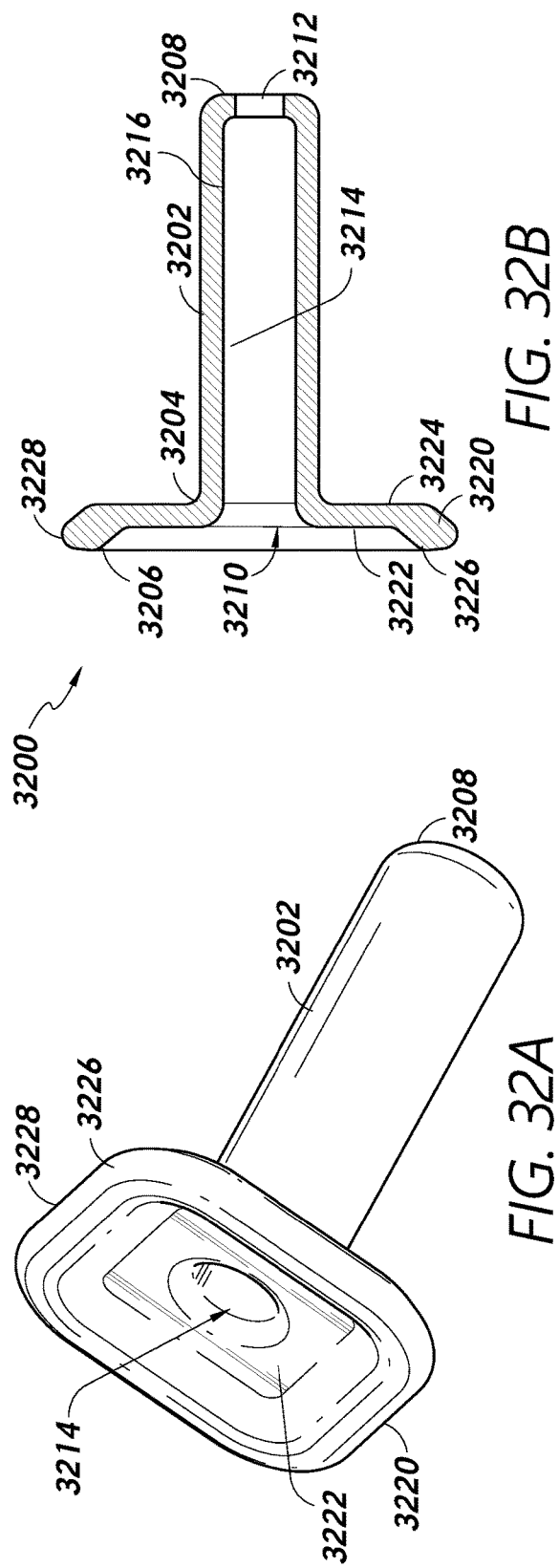
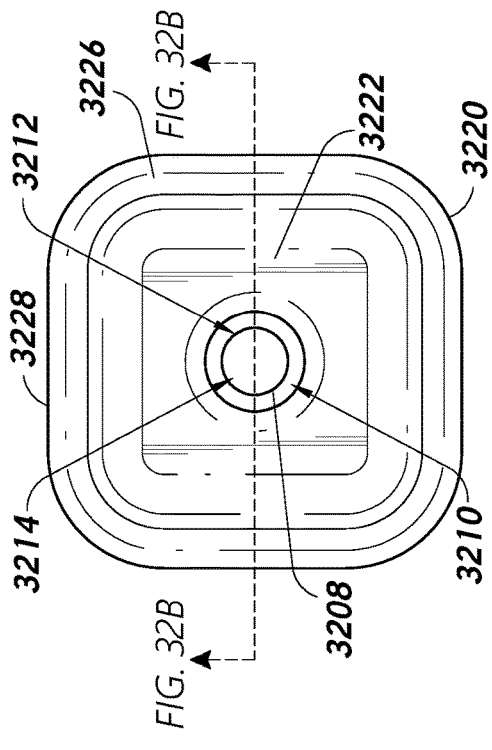

CLOSING TISSUE OPENINGS

CROSS REFERENCE TO RELATED APPLICATIONS

This application is a continuation of International Patent Application No. PCT/US2021/049358, filed Sep. 8, 2021, which claims the benefit of U.S. Patent Application No. 63/076,891, filed Sep. 10, 2020, the entire disclosures of each of which are incorporated by reference for all purposes.

BACKGROUND

Technical Field

The present disclosure generally relates to the field of closing tissue openings.

Description of Related Art

As part of medical procedures, openings can be formed in various types of tissues to allow access to target sites. Medical treatments and/or medical devices can be delivered to the target sites through the tissue openings. The tissue openings need to be closed around instrumentation positioned within the openings during the medical procedures so as to maintain hemostasis, and/or can be closed after completion of the medical procedures.

SUMMARY

In some cases, the present disclosure relates to systems, devices and methods for providing one or more improved patterns of stitching around an opening to reduce or eliminate damage to any tethers extending through the opening. In some cases, the present disclosure relates to systems, devices and methods for providing a protective sleeve configured to be positioned within the opening in the target tissue. Tethers extending through the opening can be threaded through the protective sleeve so as to prevent or reduce damage to the tethers.

In an implementation, a suture system can comprise a first and a second curved double arm needle, and a needle manipulating instrument. The needle manipulating instrument can comprise a distal portion configured to engage the first and the second curved double arm needles, and to maintain the needles in alignment with and parallel to one another and at a predetermined orientation relative to the needle manipulating instrument.

In some cases, the suture system can comprise a needle docking device configured to maintain the first and the second curved double arm needles in alignment with and parallel to one another and at predetermined orientations relative to the needle docking device. The distal portion of the needle manipulating instrument can be configured to engage the first and the second curved double arm needles while the first and second curved double arm needles are in the needle docking device, and to maintain the needles in alignment with and parallel to one another and at the predetermined orientation relative to the needle manipulating instrument while the needles are removed from the needle docking device.

In some cases, the needle docking device can comprise a first wall portion comprising a first pair of openings sized to allow extension therethrough of first respective portions the first and second curved double arm needles. The needle docking device can include a second wall portion spaced from the first wall portion, the second wall portion comprising a second pair of openings sized to allow extension therethrough of second respective portions of the first and second curved double arm needles. A distance between the first pair of openings and a distance between the second pair of openings can be predetermined to provide a predetermined distance between the first and second curved double arm needles.

In some cases, a cross-sectional size of each of the first and second curved double arm needles can vary along a respective length of the needles, and where a size of the first pair of openings and a size of the second pair of openings are configured to allow a predetermined length of the first and the second curved double arm needles to extend through the docking device.

In some cases, the needle docking device can have a solid configuration. In some cases, the docking device can comprise a first lumen extending between corresponding openings on the first wall portion and the second wall portion for receiving the first curved double arm needle and a second lumen extending between corresponding openings on the first wall portion and the second wall portion for receiving the second curved double arm needle. The first lumen and the second lumen can each comprise engagement features configured to engage with the first and second curved double arm needles to maintain a predetermined orientation of the needles.

In some cases, the needle manipulating instrument can comprises a surgical clamp. The surgical clamp can comprise a first arm pivotally coupled to a second arm, a first handle and a second handle associated with respective proximal portions of the first arm and the second arm, and a first distal portion of the first arm and a second distal portion of the second arm being configured to be pivoted toward one another to engage the first and the second curved double arm needles. The first and second distal portions can comprise a first curvature and a second curvature, respectively. The first arm can comprise a portion distal of the first curvature extending along a first axis which is perpendicular to that along which a portion proximal of the first curvature extends. The second arm can comprise a portion distal of the second curvature extending along a second axis which is perpendicular to that along which a portion proximal of the second curvature extends. At least one of the portion of the first arm distal of the first curvature and the portion of the second arm distal of the second curvature can comprise a first recess and a second recess on a surface oriented toward the other arm, the first and the second recesses being configured to receive the first and the second curved double arm needles.

In some cases, a length of each of the first arm and the second arm can be adjustable.

In some cases, the first distal portion and the second distal portion can be configured to pivot toward one another to position the first and the second curved double arm needles within corresponding first and second recesses and maintain the first and the second curved double arm needles at a predetermined distance from one another. In some cases, while the first and second curved double arm needles are held by the surgical clamp, the first and second curved double arm needles can be parallel to the portion of the first arm proximal of the first curvature and the portion of the second arm proximal of the second curvature, and where sharp ends of the first and the second curved double arm needles are aligned with one another and positioned distally of the surgical clamp.

In some cases, a cross-sectional size of each of the first and second curved double arm needles vary along a respective length of the needles, and where a width of the first recess and the second recess are configured to allow a predetermined length of the first and the second curved double arm needles to be positioned within the first and second recesses.

In some cases, the needle manipulating instrument can comprise a proximal handle, and a shaft portion extending distally from the proximal handle. A distal portion of the shaft portion can comprise a first and a second lumen extending to a distal end of the shaft portion and a respective needle engagement feature can be within each of the first and second lumens. The respective needle engagement feature can extend from a corresponding lumen wall and can be configured to engage with a respective proximal portion of the first or second curved double arm needle positioned within the lumen.

In some cases, the shaft portion can comprise a first and a second shaft extending distally from the proximal handle, where the first shaft comprises the first lumen and the second shaft comprises the second lumen. In some cases, the shaft portion can comprise a curvature. In some cases, the shaft portion is linear.

In some cases, respective proximal portions of the first and second curved double arm needles can be coupled to a suture, and where respective portions of the suture are received within the first lumen and the second lumen.

In some cases, wall portions of the shaft portion defining the first lumen and the second lumen comprise respective openings to allow extension therethrough of a suture portion coupled to the respective proximal portions of the first and second curved double arm needles, the respective openings opening to the distal end of the shaft portion.

In an implementation, a method of suturing can comprise engaging and maintaining a first pair of curved double arm needles in alignment with and parallel to one another using a needle manipulating instrument, and inserting sharp ends of the first pair of curved double arm needles, while the first pair of curved double arm needles is held by the needle manipulating instrument, into a target tissue in an area adjacent to an opening in the target tissue to make a first stitch. The method can include inserting sharp ends of one of the first pair of curved double arm needles or a second pair of curved double arm needles, while the first pair or the second pair of curved double arm needles is held by the needle manipulating instrument, into the target tissue in the area adjacent to the opening to make a second stitch, and tensioning sutures of the first stitch and the second stitch to reduce a size of the opening in the target tissue.

In some cases, engaging the first pair of curved double arm needles can comprise removing the first pair of curved double arm needles from a needle docking device.

In some cases, inserting sharp ends of the first pair of curved double arm needles into the target tissue can comprise inserting the first pair of curved double arm needles on a first side of the opening to position the first stitch on the first side of the opening, and where inserting sharp ends of the one of the first or the second pair of curved double arm needles into the target tissue can comprise inserting the one of the first or the second pair of curved double arm needles to a second side of the opening to position the second stitch parallel to and on a second side of the opening. In some cases, the first stitch and the second stitch comprise a same orientation. In some cases, the first stitch and the second stitch comprise opposing orientations.

In some cases, inserting sharp ends of the first pair of curved double arm needles into the target tissue can comprise inserting a first needle and a second needle of the first pair of curved double arm needles on a first set of opposing sides of the opening to position the first stitch on two sides of the opening, and where inserting sharp ends of the one of the first pair or second pair of curved double arm needles into the target tissue can comprise inserting a first needle and a second needle of the first or second pair of curved double arm needles on a second set of opposing sides of the opening to position the second stitch on two sides of the opening. In some cases, the first stitch and the second stitch are perpendicular to one another. In some cases, the first and second opposing sides can be the same set of opposing sides, where suture portions of the first stitch are outside of suture portions of the second stitch, and where the first stitch and the second stitch have opposing orientations.

In some cases, engaging and maintaining the first pair of curved double arm needles in alignment with and parallel to one another using the needle manipulating instrument can comprise pivoting a first distal portion of a first arm toward a second distal portion of a second arm of the needle manipulating instrument. The first distal portion and the second distal portion each can comprise a first curvature and a second curvature, respectively. The first arm can comprise a portion distal of the first curvature extending along a first axis perpendicular to that along which a portion proximal of the first curvature extends and the second arm can comprise a portion distal of the second curvature extending along a second axis perpendicular to that along which a portion proximal of the second curvature extends. Engaging and maintaining the first pair of curved double arm needles can include positioning a first and a second needle of the first pair of curved double arm needles within a first recess and a second recess on a surface of the first arm oriented toward the second arm and distal of the first curvature, respectively, to fixate the first pair of needles between the first arm and second arm.

In some cases, engaging and maintaining the first pair of curved double arm needles can further comprise positioning the first and the second needle of the first pair of curved double arm needles within a first recess and a second recess on a surface of the second arm oriented toward the first arm and distal of the second curvature, respectively, to fixate the first pair of needles between the first arm and second arm.

In some cases, engaging and maintaining the first pair of curved double arm needles in alignment with and parallel to one another using the needle manipulating instrument can comprise inserting respective proximal portions of a first and second needle of the first pair of curved double arm needles into a first and a second lumen of a shaft portion of the needle manipulating instrument, respectively, extending within the lumen a proximal handle. Engaging and maintaining the first pair of curved double arm needles can include engaging proximal portions of the first and second needle with respective needle engagement feature positioned within each of the first and second lumens.

In some cases, proximal ends of each needle of the first pair of curved double arm needles can be coupled to one another via a suture, and where the method can include threading each needle of the first pair of curved double arm needles through corresponding openings of a pad to position a portion of the suture over the pad.

In an implementation, a suture system can comprise a cord configured to be positioned over a target tissue and to at least partially surround an opening in the target tissue, and a plurality of anchors configured to be partially embedded in the target tissue, each of the plurality of anchors being configured to be coupled to the cord at predetermined intervals to anchor the cord to the target tissue.

In some cases, the system can include a fastener configured to be coupled to two corresponding portions of the cord and maintain the two corresponding portions of the cord at predetermined positions relative to one another such that the cord at least partially surrounds the opening in the target tissue.

In some cases, the system can include an elongate tube comprising a lumen extending therethrough, the lumen being configured to slidably receive at least a portion of the cord, where the elongate tube is configured to be positioned over the target tissue and at least partially surround the opening in the target tissue, and where each of the plurality of anchors are configured to be coupled to the elongate tube to anchor the elongate tube to the target tissue.

In some cases, the system can include a fastener configured to couple to two corresponding portions of the elongate tube and maintain the two corresponding portions of the elongate tube at predetermined positions relative to one another such that the elongate tube at least partially surrounds the opening in the target tissue.

In some cases, the fastener can comprise two openings configured to allow the corresponding portions of the cord or the elongate tube to extend therethrough to couple to the cord or the elongate tube. In some cases, the fastener is a pledget. In some cases, the system can include a plurality of anchors configured to be coupled to the fastener to anchor the fastener to the target tissue.

In some cases, the system can include a tourniquet, where the tourniquet can comprise a lumen extending therethrough, the lumen being configured to allow extension therethrough of at least some portions of the elongate tube proximal of the fastener and at least some portions of the cord proximal of the fastener. In some cases, a proximal portion of the tourniquet can comprise a cord engagement feature configured to allow fixating of a portion of the cord relative to the tourniquet. In some cases, the cord engagement feature can comprise a protrusion around which the portion of the cord is configured to be wound around.

In some cases, the system can comprise an elongate tube applicator comprising a distal portion configured to engage the elongate tube to maintain the elongate tube in a predetermined shape over the target tissue while the elongate tube is anchored to the target tissue. In some cases, the predetermined shape can comprise a square, a hexagon, a star shape, or a circle.

In some cases, the elongate tube applicator can comprise a proximal handle, a shaft extending distally from the handle and an elongate tube engagement component coupled to a distal end of the shaft. The elongate tube engagement component can comprise a plurality of extensions, each of the plurality of extensions comprising a proximal portion extending perpendicularly from the shaft and a distal portion extending distally and perpendicularly from the proximal portion. The elongate tube engagement component can comprise a recess on a surface of each distal portion of the plurality of extensions, the recess being configured to receive a corresponding portion of the elongate tube, and where the surface is oriented toward a longitudinal axis of the shaft.

In some cases, the elongate tube engagement component can comprise four extensions and the elongate tube engagement component is configured to engage four corresponding portions of the elongate tube to maintain the elongate tube in a square shape.

In some cases, the shaft of the applicator can comprise a locking swivel joint configure to allow a distal portion and a proximal portion of the shaft to both rotate 360 degrees around a longitudinal axis and bend to form an angle of between 90 degrees and 180 degrees.

In some cases, the opening in the target tissue can be formed in an apex region of a heart ventricular wall, and where each of the plurality of anchors can comprise a length configured to partially penetrate the myocardium of the heart ventricular wall.

In some cases, the plurality of anchors can comprise a plurality of discrete sutures. In some cases, the plurality of anchors can comprise a plurality of staples.

In an implementation, a method of suturing a tissue opening can comprise positioning a cord over a target tissue to at least partially surround an opening in the target tissue, partially embedding a plurality of anchors in the target tissue and coupling each of the plurality of anchors to the cord at predetermined intervals to anchor the cord to the target tissue, and tensioning the cord to reduce a size of the opening.

In some cases, the method can comprise providing an elongate tube comprising a lumen extending therethrough and at least a portion of the cord slidably received within the lumen, and positioning the elongate tube over the target tissue to at least partially surround the opening in the target tissue, Coupling each of the plurality of anchors to the cord at predetermined intervals can comprise coupling each of the plurality of anchors at predetermined interval to the elongate tube to anchor the elongate tube to the target tissue.

In some cases, the method can comprise positioning an elongate tube applicator over the target tissue and engaging the elongate tube using the elongate tube applicator to maintain the elongate tube in a predetermined shape while the elongate tube is anchored to the target tissue.

In some cases, the elongate tube applicator can comprise a shaft extending distally from a proximal handle, and an elongate tube engagement component coupled to a distal end of the shaft, where engaging the elongate tube can comprise positioning corresponding portions of the elongate tube in respective recesses on surfaces of the elongate tube engagement component which are oriented toward a longitudinal axis of the shaft.

In some cases, the method can comprise providing a fastener coupled to corresponding portions of one of the cord or the elongate tube to maintain the corresponding portions of the cord or the elongate tube at predetermined positions relative to one another such that the cord or the elongate tube at least partially surrounds the opening in the target tissue. In some cases, the method can comprise inserting the corresponding portions of the cord or the elongate tube through two openings in the fastener to maintain the corresponding portions of the cord or the elongate tube at predetermined positions relative to one another. In some cases, the method can comprise coupling a plurality of anchors to the fastener and partially embedding the plurality of anchors into the target tissue to anchor the fastener to the target tissue. In some cases, the method can comprise inserting portions of the elongate tube proximal of the fastener into a lumen of a tourniquet. In some cases, the method can comprise threading portions of the cord proximal of the fastener into a lumen of a tourniquet. In some cases, tensioning the cord to reduce the size of the opening can comprise fixating a portion of the cord around a cord engagement feature on a proximal portion of the tourniquet.

In some cases, partially embedding a plurality of anchors in the target tissue and coupling each of the plurality of anchors can comprise deploying a plurality of sutures. In some cases, partially embedding a plurality of anchors in the target tissue and coupling each of the plurality of anchors can comprise deploying a plurality of staples.

In an implementation, a system can comprise a flexible elongate tube configured to be inserted into an opening in a target tissue and be collapsible around a longitudinal axis, the flexible elongate tube comprising a lumen extending therethrough, where, when the flexible elongate tube is inserted into the opening, is configured to receive at least one tether extending through the opening. The system can include a deployment applicator configured to deploy the flexible elongate tube into the opening in the target tissue, the deployment applicator comprising an elongate tube engagement component associate with a distal portion, where the engagement component is configured to be received within the lumen of the flexible elongate tube.

In some cases, the deployment applicator can comprise a handle associated with a proximal portion of the deployment applicator, a shaft extending between the handle and the elongate tube engagement component, and a lumen extending therethrough, where, while the elongate tube engagement component is inserted into the opening in the target tissue, the lumen is configured to receive the at least one tether extending through the opening.

In some cases, a proximal portion of the elongate tube engagement component can comprise a ridge around a circumference thereof.

In some cases, the deployment applicator can comprise an inner member, where the elongate tube engagement component is associated with a distal portion of the inner member. The inner member can include a proximal handle, a shaft extending between the proximal handle and the elongate tube engagement component, and an inner member lumen extending therethrough and wherein, while the elongate tube engagement component is inserted into the opening in the target tissue, the inner member lumen is configured to receive the at least one tether. The deployment applicator can comprise an outer sheath member. The outer sheath member can comprise a handle engagement portion associated with a proximal portion of the outer sheath member, the handle engagement portion configured to engage with the proximal handle of the inner member to prevent over-insertion of the inner member. The outer sheath member can comprise a ridge associated with a distal portion of the outer sheath member, the ridge being configured to contact a proximal end of the flexible elongate tube engaged by the elongate tube engagement component. The outer sheath member can comprise a shaft extending between the handle engagement portion and the ridge, and an outer sheath lumen extending therethrough, where, while the elongate tube engagement component is inserted into the opening in the target tissue, a portion of the inner member is configured to be slidably received within outer sheath lumen with the elongate tube engagement component extending distally of a distal end of the outer sheath member and the proximal handle extending proximally of the handle engagement portion.

In some cases, the inner member is configured to be proximally displaced relative to the outer sheath member, as the ridge of the outer sheath member is configured to maintain contact with a portion of the flexible elongate tube extending externally of the opening to deploy the flexible elongate tube from the elongate tube engagement component into the opening in the target tissue.

In some cases, the ridge of the outer sheath member can extend circumferentially around a distal end of the shaft. In some cases, the flexible elongate tube can comprise a flange at a proximal end and wherein a distal surface of the ridge is configured to be positioned against a proximal surface of the flange. In some cases, the flexible elongate tube can be configured to be inserted into an opening formed in a target tissue, and where the flange is configured to be positioned over an external surface of the target tissue and a distal portion of the flexible elongate tube is configured to be positioned within the opening. In some cases, the flange can comprise a reinforced portion extending circumferentially around an outer edge portion of the flange.

In some cases, the target tissue is a heart wall, where the flange is configured to be positioned over an external portion of the heart wall and a distal portion of the flexible elongate tube is configured to be positioned within the opening in the heart wall.

In an implementation, a method can comprise providing a flexible elongate tube engaged with a deployment applicator, where the flexible elongate tube comprises a lumen extending therethrough, and where the deployment applicator comprises an elongate tube engagement component associate with a distal portion, the engagement component being configured to be received within the lumen of the flexible elongate tube. The method can include threading a tether through a lumen of the deployment applicator, the tether extending from an opening in a target tissue, and positioning an elongate portion of the flexible elongate tube received around the elongate tube engagement component into the opening while the tether extends through the lumen of the deployment applicator. The method can include removing the deployment applicator from the opening to leave the elongate portion of the flexible elongate tube within the opening and around the tether, and collapsing the flexible elongate tube within the opening around a longitudinal axis of the flexible elongate tube and around the tether.

In some cases, the flexible elongate tube can comprise a flange around a proximal end, and where positioning the elongate portion of the flexible elongate tube received around the engagement component into the opening can comprise positioning the flange of the flexible elongate tube against the target tissue.

In some cases, the method can comprise positioning the flexible elongate tube over the elongate tube engagement component of the deployment applicator.

In some cases, a proximal portion of the elongate tube engagement component can comprise a ridge around a circumference thereof, and where positioning the flexible elongate tube over the elongate tube engagement component can comprise positioning a proximal surface of a flange around a proximal end of the flexible elongate tube against a distal surface of the ridge.

In some cases, the deployment applicator can comprise an inner member and the elongate tube engagement component being associated with a distal portion of the inner member, and an outer sheath member comprising an outer sheath lumen extending therethrough and a portion of the inner member slidably received within the outer sheath lumen, such that the method can include advancing the distal portion of the inner member comprising the elongate tube engagement component associated therewith into the opening for positioning the flexible elongate tube into the opening, and proximally displacing the inner member relative to the outer sheath member to remove the flexible elongate tube from around the elongate tube engagement component while contacting the outer sheath member and a portion of the flexible elongate tube extending externally of the opening to maintain the flexible elongate tube in the opening.

In some cases, the outer sheath member can comprise a ridge associated with a distal portion, and where the method can include contacting the ridge of the outer sheath member and the portion of the flexible elongate tube extending externally of the opening to maintain the flexible elongate tube in the opening.

In some cases, the flexible elongate tube can comprise a flange around a proximal end, and contacting the ridge of the outer sheath member and the portion of the flexible elongate tube extending externally of the opening can comprise contacting the ridge of the outer sheath member and the flange.

Each method disclosed herein also encompass one or more simulations of the method, which are useful, for example, for teaching, demonstration, testing, device development, and procedure development. For example, methods for treating or diagnosing a patient include corresponding simulated methods performed on a simulated patient. Suitable simulated patients or anthropogenic ghosts can include any combination of physical and virtual elements. Examples of physical elements include whole human or animal cadavers, or any portion thereof, including, organ systems, individual organs, or tissue; and manufactured cadaver, organ system, organ, or tissue simulations. Examples of virtual elements include visual simulations, which can be displayed on a screen; projected on a screen, surface, space, or volume; and holographic images. The simulation can also include one or more of another type of sensory input, for example, auditory, tactile, and olfactory stimuli.

For purposes of summarizing the disclosure, certain aspects, advantages and novel features have been described herein. It is to be understood that not necessarily all such advantages may be achieved in accordance with any particular embodiment. Thus, the disclosed cases may be carried out in a manner that achieves or optimizes one advantage or group of advantages as taught herein without necessarily achieving other advantages as may be taught or suggested herein.

BRIEF DESCRIPTION OF THE DRAWINGS

Various cases are depicted in the accompanying drawings for illustrative purposes and should in no way be interpreted as limiting the scope of the inventions. In addition, various features of different disclosed cases can be combined to form additional cases, which are part of this disclosure. Throughout the drawings, reference numbers may be reused to indicate correspondence between reference elements. However, it should be understood that the use of similar reference numbers in connection with multiple drawings does not necessarily imply similarity between respective cases associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some cases or configurations.

FIG. 2 is a schematic diagram of an example of a suture pattern comprising a first stitch and a second stitch formed on a first and second side of an opening in a target tissue, respectively, where the first and second stitches have opposing orientations.

FIG. 3 is a schematic diagram of an example of a suture pattern comprising a first stitch and a second stitch formed on a first and second side of an opening in a target tissue, respectively, where the first stitch and the second stitch can have the same or similar orientation.

FIG. 6A is a perspective view of an example of a surgical clamp and FIG. 6B is a more detailed view of a distal portion of the surgical clamp.

FIGS. 11A, 11B, 11C and 11D show various views of another example of a needle holder.

FIGS. 14A, 14B and 14C show various steps of using the needle holder of FIG. 11 to form a suture in a target tissue adjacent to an opening.

FIG. 15 is process flow diagram of an example of a suturing process for closing an opening in a target tissue.

FIGS. 19A, 19B and 19C show examples of pre-assembled configurations of various components of the suture system of FIG. 16.

FIGS. 31A, 31B, 31C are a perspective view, cross-sectional view and distal plan view, of an example of a flexible elongate tube comprising a reinforced portion on a flange of the flexible elongate tube.

FIGS. 32A, 32B, 32C are a perspective view, cross-sectional view and distal plan view, of another example of a flexible elongate tube comprising a reinforced portion on a flange of the flexible elongate tube.

DETAILED DESCRIPTION

Figure 1:
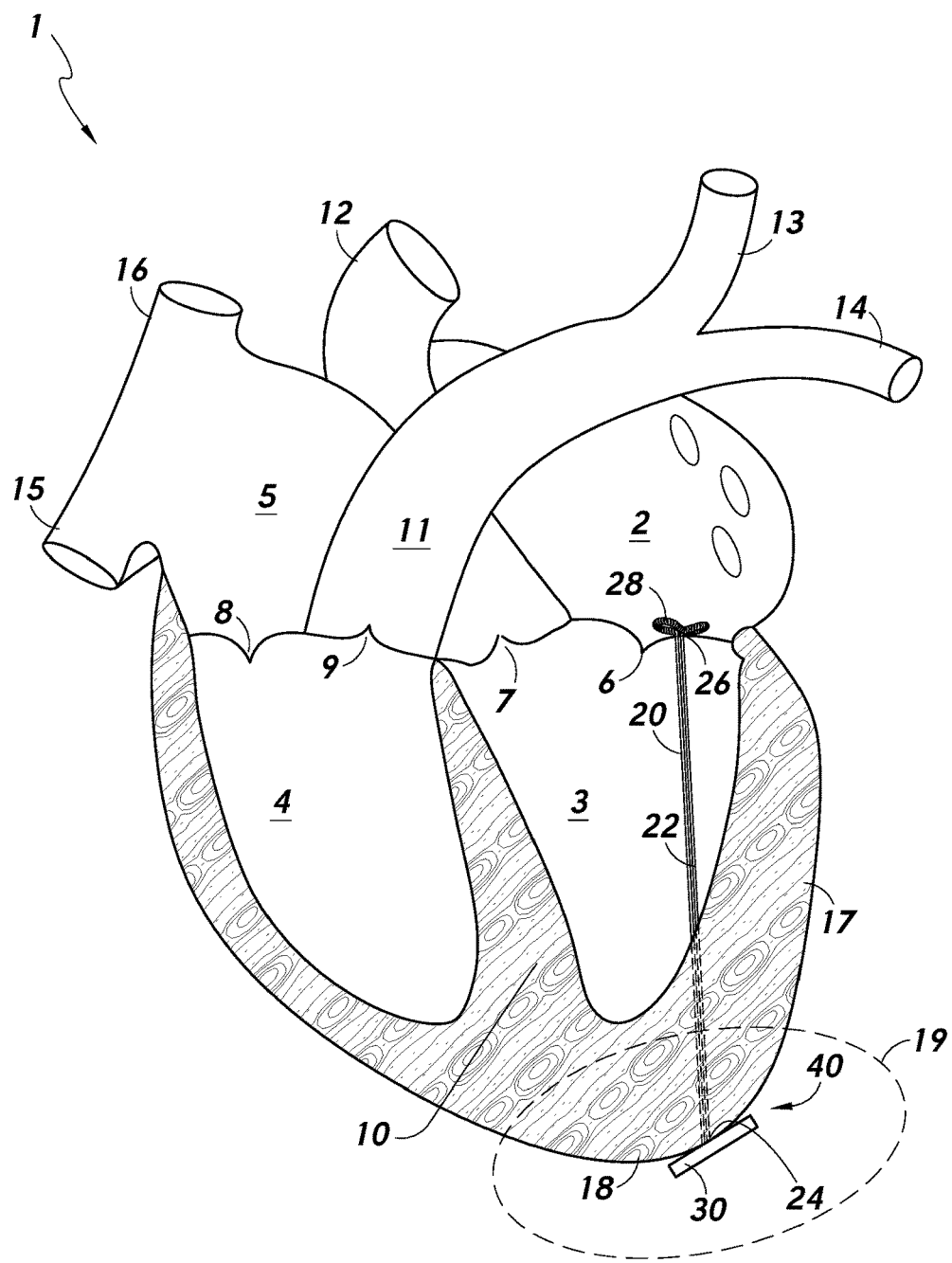
FIG. 1 is a cross-sectional view of a human heart.

The headings provided herein are for convenience only and do not necessarily affect the scope or meaning of the claimed invention.

In some cases, described herein are systems, devices and methods relating to forming suture patterns around an opening for closing the opening, where the suture patterns can reduce or eliminate damage to any tethers extending through the opening. In some cases, described herein are systems, devices and methods relating to a protective sleeve configured to be positioned within the opening in the target tissue. Tethers extending through the opening can be threaded through the protective sleeve so as to prevent or reduce damage to the tethers.

Although certain preferred cases and examples are disclosed below, inventive subject matter extends beyond the specifically disclosed cases to other alternative cases and/or uses and to modifications and equivalents thereof. Thus, the scope of the claims that may arise herefrom is not limited by any of the particular cases described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain cases; however, the order of description should not be construed to imply that these operations are order dependent. Additionally, the structures, systems, and/or devices described herein may be embodied as integrated components or as separate components. For purposes of comparing various cases, certain aspects and advantages of these cases are described. Not necessarily all such aspects or advantages are achieved by any particular embodiment. Thus, for example, various cases may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred cases. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element (s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Openings can be formed at various target tissue sites, for example to access a lumen and/or chamber through the tissue. In some cases, openings can be formed in the heart wall. For example, the openings can be formed in the heart wall to provide access to one or more heart chambers so as to treat various heart conditions, including any number of heart valve abnormalities. An opening can be formed in the ventricular heart wall, including the left ventricular heart wall, to perform heart valve repair and/or replacement.

FIG. 1 shows various features of a human heart 1. The heart 1 includes four chambers, namely the left atrium 2, the left ventricle 3, the right ventricle 4, and the right atrium 5. A wall of muscle, referred to as the septum 10, separates the left atrium 2 and right atrium 5, and the left ventricle 3 and right ventricle 4. Blood flow through the heart 1 is at least partially controlled by four valves, the mitral valve 6, aortic valve 7, tricuspid valve 8, and pulmonary valve 9. The mitral valve 6 separates the left atrium 2 and the left ventricle 3 and controls blood flow therebetween. The aortic valve 7 separates and controls blood flow between the left ventricle 3 and the aorta 12. The tricuspid valve 8 separates the right atrium 5 and the right ventricle 4 and controls blood flow therebetween. The pulmonary valve 9 separates the right ventricle 4 and the pulmonary artery 11, controlling blood flow therebetween.

In a healthy heart, the heart valves can properly open and close in response to a pressure gradient present during various stages of the cardiac cycle (e.g., relaxation and contraction) to at least partially control the flow of blood to a respective region of the heart and/or to blood vessels. Deoxygenated blood arriving from the rest of the body generally flows into the right side of the heart for transport to the lungs, and oxygenated blood from the lungs generally flows into the left side of the heart for transport to the rest of the body. During ventricular diastole, deoxygenated blood arrive in the right atrium 5 from the inferior vena cava 15 and superior vena cava 16 to flow into the right ventricle 4, and oxygenated blood arrive in the left atrium 2 from the pulmonary veins to flow into the left ventricle 3. During ventricular systole, deoxygenated blood from the right ventricle 4 can flow into the pulmonary artery 11 for transport to the lungs (e.g., via the left 14 and right 13 pulmonary arteries), and oxygenated blood can flow from the left ventricle 3 to the aorta 12 for transport to the rest of the body.

A number of conditions can contribute to a higher than normal pressure in the left atrium. Dysfunction of the mitral valve can contribute to elevated left atrial pressure. Conditions such as mitral valve regurgitation and/or stenosis may result in difficulty in pumping blood from the left atrium to the left ventricle, contributing to elevated pressure in the left atrium. Valve stenosis can cause a valve to become narrowed or obstructed. Mitral valve stenosis can restrict blood flow from the left atrium to the left ventricle. Valve regurgitation occurs when a valve does not close properly. For example, regurgitation can occur due to improper coaptation of the valve leaflets, such as due to prolapse of one or more of the valve leaflets. Mitral valve regurgitation can result in blood flow leakage back into the left atrium 2 from the left ventricle 3 when the left ventricle 3 contracts. Restricted flow of blood from the left atrium 2 into the left ventricle 3, and blood flow leakage from the left ventricle 3 back into the left atrium 2 can both contribute to elevated atrial pressure. Dysfunction in the left ventricle 3 can also contribute to elevated left atrial pressure. Elevated left atrial pressure may lead to left atrial enlargement, producing symptoms such as shortness of breath during exertion, fatigue, chest pain, fainting, abnormal heartbeat, and swelling of the legs and feet.

Forming an opening 40 through the heart wall 17 can be used to access a heart valve for treating various heart valve irregularities. Heart valve repair and/or replacement procedures can be performed to improve or restore valve function. For example, mitral valve repair procedures can be performed to alleviate mitral valve dysfunction, including mitral valve prolapse. In some cases, a transapical approach can be used to gain access into the heart 1. For example, mitral valve repair procedures can include accessing the mitral valve 6 from within the left ventricle 3, where entry into the left ventricle 3 can be achieved through the apex region 19 of the heart 1. The heart wall 17 can be punctured in the apex region 19 to form the opening 40 so as to allow delivery of medical devices and/or therapy to the mitral valve 6. The apex region 19 is schematically shown in FIG. 1 as the area within the dashed circle. As used herein, the "apex region" can include the true apex 18 of the heart 1 and an area of the heart wall 17 covering up to about 5 centimeters (cm) around the true apex 18. For example, the opening in the left ventricular portion of the heart wall 17 about 2 centimeters (cm) to about 4 centimeters (cm) from the true apex 18.

Mitral valve repair and/or replacement procedures can be performed to improve or restore mitral valve function. FIG. 1 shows a tether 20 coupling a leaflet of the mitral valve 6 to the heart wall 17. Mitral valve repair surgeries can comprise deploying one or more tethers onto a mitral valve leaflet for tethering the leaflet to the heart wall 17. Coupling the leaflet to the heart wall 17 can facilitate reshaping of the mitral valve 6, such as to reduce or eliminate leaflet prolapse. The tether 20 can serve to improve coaptation of the leaflet. In some cases, the tether 20 can be configured to couple the leaflet to a left ventricular portion of the heart wall 17. In some cases, more than one tether can be used to couple the leaflet to the heart wall 17. These tethers can be made from a variety of materials. One or more of these tethers can comprise for example expanded polytetrafluoroethylene (ePTFE). For example, the tether 20 can be an ePTFE suture.

The tether 20 can comprise an elongate portion 22 which extends between a proximal end 24 and a distal end 26. The proximal end 24 of the tether 20 can be coupled to the heart wall 17. The distal end 26 of the tether 20 can be coupled to the leaflet of the mitral valve 6. In some cases, the distal end 26 can be coupled to a suture knot 28 to facilitate securing the tether 20 to the leaflet. The suture knot 28 can be positioned at least partially over an upper surface of the leaflet. For example, the suture knot 28 can be positioned over an atrial facing surface of the mitral valve leaflet. The proximal end 24 can be anchored to a portion of the heart wall 17 at or proximate to the apex 18 of the heart 1, such as in the apex region 19. In some cases, a portion of the elongate portion 22 can extend at least partially through the heart wall 17. FIG. 1 shows the tether 20 extending through an entire thickness of the heart wall 17. In some cases, the proximal end 24 can be anchored at a position adjacent to an externally facing surface of the pericardium. In some cases, the proximal end 24 can be anchored at a position external to the heart 1. In some cases, the tether 20 can extend partially through the heart wall 17 such that the proximal end 24 is anchored within or adjacent to a layer of the heart wall 17, including for example the epicardium or the myocardium.

The proximal end 24 can be coupled to a pad 30. The tether 20 can couple the mitral valve leaflet to the pad 30, extending from the leaflet through the left ventricle 3 and opening 40 in the heart wall 17 to the pad 30. In some cases, the pad 30 can be positioned over and/or adjacent to an exterior surface of the heart 1. In some cases, the pad 30 can be positioned over and/or adjacent to the pericardium. For example, the proximal end 24 can be coupled to a pad 30 on and in contact with the pericardium to facilitate anchoring the proximal end 24 to the target location within the apex region 19 and maintain desired tension in the tether 20. In some cases, the pad 30 can be positioned within, over and/or adjacent to a layer of the heart wall 17, such as the myocardium or epicardium.

The pad 30 can be positioned over the opening 40 formed in the heart wall 17. For example, the tether 20 can extend through the opening 40 and coupled to the pad 30. The opening 40 can be closed and/or sealed and the pad 30 can be positioned at least partially over the closed and/or sealed opening 40 to anchor the proximal end 24 of the tether 20. Surgical instrumentation can be advanced and/or retracted through, and/or positioned within the opening 40 for a surgical procedure. For example, an introducer instrument can be positioned through the opening 40 formed in the heart wall 17 during a mitral valve repair procedure to facilitate deployment of the tether 20 to the mitral valve leaflet.

Traditionally, one or more purse-string sutures can be stitched around an opening, such as an opening formed in the heart wall, to close the opening. A purse-string suture can be formed in the target tissue to surround the opening such that the purse-string suture can be tensioned to reduce the size of the opening. The size of the opening can be reduced to close the opening around any surgical instruments extending through the opening during a procedure to provide hemostasis. As described herein, more than one tether can be deployed to the mitral valve leaflet. The purse-string suture can be tensioned to close the opening around any surgical instrumentation and one or more deployed tethers during a procedure, such as while one or more additional tethers are deployed. After completion of the procedure, the purse-string suture can be tensioned to seal the opening. In some cases, the purse-string suture can be used to close the opening around the one or more tethers extending therethrough. In some cases, two concentric purse-string sutures can be formed around a transapical access opening in the ventricular heart wall to facilitate closure of the opening.

Tensioning of traditional purse-string sutures to close an opening can result in damage to portions of tethers extending through the opening, resulting in abrasive damage to and/or breakage of the tethers. Tensioning of traditional purse-string sutures can cause undesired folding of the tissue proximate and/or adjacent to the opening. The undesired folding of the tissue can in turn result in concentrated loading on portions of the tethers proximate to and/or extending through the opening, leading to damage and/or breakage of the tethers. Tensioning of traditional purse-string sutures may result in the purse-string sutures cutting through the tissue. Movement of the purse-string sutures through the tissue can result in contact between the tethers and the purse-string sutures, thereby leading to damage and/or breakage of the tethers.

Described herein are systems, devices and methods relating to providing improved suture patterns which can reduce or eliminate damage to the plurality of tethers extending through the opening in the target tissue. In some cases, a suture system can comprise a needle manipulating instrument configured to engage a first curved double arm needle and a second curved double arm needle. A distal portion of the needle manipulating instrument can be configured to engage the first and the second curved double arm needles, and to maintain the needles in alignment with and parallel to one another and at a predetermined orientation relative to the needle manipulating instrument. The needle manipulating instrument can be used to hold onto the needles while using the needles to form a suture around the opening in the target tissue. The needle manipulating instrument can be used to maintain the first and second curved double arm needles in the predetermined orientation while forming the suture in the target tissue. For example, the needle manipulating instrument can be used to form one or more suture patterns described herein.

In some cases, the needle manipulating instrument can comprise a surgical clamp. The surgical clamp can comprise a first arm and a second arm. The first arm can a first distal portion and the second arm can comprise a second distal portion. A pair of curved double arm needles can be sandwiched between the first and second distal portions as the first and second distal portions are pivoted toward one another. The first distal portion and the second distal portion can comprise a first curvature and a second curvature, respectively. The first distal portion can comprise a first distal perpendicular portion distal of, and a first proximal perpendicular portion proximal of, the first curvature, where the first distal and proximal perpendicular portions are perpendicular or substantially perpendicular to one another. The second distal portion can comprise a second distal perpendicular portion distal of, and a second proximal perpendicular portion proximal of, the second curvature, where the second distal and proximal perpendicular portions are perpendicular or substantially perpendicular to one another. Corresponding portions of the pair of curved double arm needles can be received within respective recesses on one or both of the first and second distal perpendicular portions. For example, both the first and second distal perpendicular portions can comprise a first and a second recess on a surface oriented toward the other distal perpendicular portion. Corresponding portions of the pair of curved double arm needles can be securely received within the recesses on both the first and second distal perpendicular portions of the surgical clamp and be maintained in predetermined orientations by the surgical clamp.

In some cases, the needle manipulating instrument can comprise a needle holder which can have a first shaft and a second shaft, where a portion of a first and a second curved double arm needle can be inserted into a distal end of the first shaft and second shaft for engagement with respective needle engagement features therein. For example, each of the first shaft and second shaft can comprise a lumen extending at least through respective distal portions to the distal end thereof. Respective needle engagement features configured to engage the first and second curved double arm needles can be positioned within the first lumen of the first shaft and the second lumen of the second shaft. Proximal portions of the first and second curved double arm needles can be inserted into the distal ends of the first and second shafts and into the first and second lumens, respectively, such that the first and second curved double arm needles can be securely engaged in predetermined orientations by the needle holder.

The suture system can comprise a needle docking device configured to maintain the first and the second curved double arm needles in predetermined orientations relative to one another and the docking device. The needle docking device can be configured to maintain the first and second curved double arm needles in alignment with and parallel to one another and at a predetermined distance from one another. The distal portion of the needle manipulating instrument can be configured to engage the first and the second curved double arm needles while the first and second curved double arm needles are held by the needle docking device.

In some cases, provided herein are systems, devices and methods relating to forming an improved suture structure for closing an opening in a target tissue. The suture structure can comprise maintaining a portion of a cord and/or elongate tube in a loop configuration over the target tissue and at least partially surrounding the opening in the target tissue. A plurality of anchors can be positioned along the portion of the cord and/or elongate tube in the loop configuration to anchor the cord and/or elongate tube to the target tissue. Maintaining the elongate tube and cord above the target tissue can advantageously prevent interference of the elongate tube and cord with any tethers extending through the opening. Portions of the anchors embedded within the target tissue can have an orientation so as to avoid interaction with any tethers. In some cases, using a plurality of discrete anchors can simplify the deployment of the suture structure, and/or provide anchors having more uniform depth and/or spacing.

In some cases, tethers extending through openings sutured using traditional purse-string sutures can be inserted through a protective sleeve to protect the tethers from damage due to interaction with the purse-string suture. For example, a plurality of tethers extending through an opening in a target tissue can be threaded through an inner lumen of a protective sleeve. The protective sleeve can prevent or reduce abrasion of the tethers to reduce and/or eliminate damage to the tethers, avoiding any breakage. The protective sleeve can be used in combination with one or more purse-string suture patterns traditionally used to close tissue openings. In some cases, the protective sleeve can be used in combination with one or more suture patterns described herein.

The protective sleeve can comprise a flexible elongate tube comprising an elongate portion and a flange associated with a proximal end of the elongate portion. The flexible elongate tube can comprise a lumen extending therethrough. The plurality of tethers can extend through the lumen such that the tethers are protected by the flexible elongate tube. While positioned within the opening in the target tissue, the flexible elongate tube can be configured to collapse around the tethers, such as due to forces exerted thereupon by the target tissue adjacent to the opening. For example, tensioning one or more sutures formed in the target tissue can result in the tissue pressing against the flexible elongate tube. The flexible elongate tube can collapse around a longitudinal axis around the plurality of tethers extending therethrough, facilitating sealing of the opening to maintain hemostasis. In some cases, the flexible elongate tube can be deployed into the opening in the target tissue using a deployment applicator.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Although the target tissue is described primarily herein as comprising heart ventricular wall tissue, it will be understood that the target tissue can comprise any number of different types of tissues in the heart and/or in other organs.

In some cases, systems, devices and methods for deploying one or more tethers, as described herein, can comprise one or more features as described in PCT Patent Application No. PCT/US2021/023392, filed Mar. 22, 2021, and entitled "Controlled Suture Tensioning", which is incorporated herein by reference in its entirety for all purposes.

The methods, operations, steps, etc. described herein can be performed on a living animal or on a non-living cadaver, cadaver heart, simulator (e.g., with the body parts, tissue, etc. being simulated), etc. For example, methods for treating a patient include methods for simulating the treatment on a simulated patient or anthropogenic ghost, which can include any combination of physical and virtual elements. Examples of physical elements include human or animal cadavers; any portions thereof, including organ systems, whole organs, or tissue; and manufactured elements, which can simulate the appearance, texture, resistance, or other characteristic. Virtual elements can include visual elements provided on a screen, or projected on a surface or volume, including virtual reality and augmented reality implementations. Virtual elements can also simulate other sensory stimuli, including sound, feel, and/or odor.

FIGS. 2 through 5 are schematic diagrams showing examples of different patterns of suturing to close openings in target tissues. The suture patterns described with reference to FIGS. 2 through 5 can prevent or reduce interactions between tethers extending through the openings in the target tissue and the sutures. In some cases, a first and second curved double arm needle can be engaged by a needle manipulating instrument described herein while the needles are used to form one or more of the suture patterns described with reference to FIGS. 2 through 5. The needle manipulating instrument can provide increased control in the suturing process. In some cases, use of the needle manipulating instrument can improve the speed at which the suture patterns are formed, while providing suture patterns having more uniform spacing and/or depth.

Referring to FIG. 2, a suture pattern 200 comprising a first stitch 210 and a second stitch 240 formed on a first and second side of an opening in a target tissue, respectively, where the first and second stitches 210, 240 can have opposing orientations. The first stitch 210 and second stitch 240 can each be formed using a single suture. The first stitch 210 can comprise five suture portions, a first suture portion 212, a second suture portion 214, a third suture portion 216, a fourth suture portion 218, and a fifth suture portion 220. The first suture portion 212 and the fifth suture portion 220 can extend externally of the target tissue and be threaded through a first pad 230. The second and fourth suture portions 214, 218 can be embedded within the target tissue. In some cases, the second and fourth suture portions 214, 218 can be parallel or substantially parallel to one another. The third suture portion 216 can be positioned over the second pad 232. In some cases, the first stitch 210 and the second stitch 240 can be on opposing sides of the opening. In some cases, the first stitch 210 and the second stitch 240 can be parallel or substantially parallel to one another.

The second stitch 240 can comprise five suture portions, a first suture portion 242, a second suture portion 244, a third suture portion 246, a fourth suture portion 248, and a fifth suture portion 250. In some cases, the first and second stitches 210, 240 can have opposing orientations. For example, the first suture portion 242 and the fifth suture portion 250 can be at, such as extending from the target tissue at, an opposing position around the opening relative to the first suture portion 212 and the fifth suture portion 220 of the first stitch 210. The first suture portion 242 and the fifth suture portion 250 can extend externally of the target tissue and be threaded through a third pad 260. The second and fourth suture portions 244, 248 can be embedded within the target tissue, and the third suture portion 246 can be positioned over a fourth pad 262. In some cases, the second and fourth suture portions 244, 248 can be parallel or substantially parallel to one another.

The first pad 230 and the fourth pad 262 can comprise the same or similar orientations relative to the opening in the target tissue. The second pad 232 and the third pad 260 can comprise the same or similar orientations relative to the opening in the target tissue. For example, the first pad 230 and the fourth pad 262 can be on a first side of the opening while the second pad 232 and the third pad 260 can be on a second opposing side of the opening. In some cases, the first pad 230 and the fourth pad 262 can each comprise a rectangular shape. The first and fourth pads 230, 262 can be positioned such that a pair of edges of one pad extend along dimensions that are collinear with corresponding edges of the other pad. In some cases, the second pad 232 and the third pad 260 can each comprise a rectangular shape such that a pair of edges of one pad extend along dimensions that are collinear with corresponding edges of the other pad.

FIG. 3 shows a suture pattern 300 comprising a first stitch 310 and a second stitch 340 formed on a first side and a second side of an opening in a target tissue, respectively, where the first stitch 310 and the second stitch 340 can have the same or similar orientation. The first stitch 310 and second stitch 340 can each be formed using a single suture. For example, each of the first stitch 310 and second stitch 340 can each comprise five suture portions, first suture portions 312, 342, second suture portions 314, 344, third suture portion 316, 346, fourth suture portions 318, 348 and fifth suture portions 320, 350. The first suture portions 312, 342 and the fifth suture portions 320, 350 can be on the same side of the opening in the target tissue. For example, the first suture portions 312, 342 and the fifth suture portions 320, 350 can extend externally of the target tissue on the same side of the opening. The first suture portions 312, 342 and the fifth suture portions 320, 350 can be threaded through a first pad 330 and a third pad 360, respectively, where the first pad 330 and the third pad 360 can be positioned on the same side of the opening. The second suture portions 314, 344 and fourth suture portions 318, 348 can be embedded within the target tissue. The third suture portions 316, 346 can be positioned over a second pad 332 and a four pad 362, respectively. The second pad 332 and the fourth pad 362 can be positioned on the same side of the opening in the target tissue.

In some cases, the second and fourth suture portions 314, 318 of the first stitch 310 can be parallel or substantially parallel to one another. In some cases, the second and fourth suture portions 344, 348 of the second stitch 340 can be parallel or substantially parallel to one another. In some cases, the first stitch 310 and the second stitch 340 can be on opposing sides of the opening. In some cases, the first stitch 310 and the second stitch 340 can be parallel or substantially parallel to one another.

The first pad 330 and the third pad 360 can comprise the same or similar orientations relative to the opening in the target tissue. The second pad 332 and the fourth pad 362 can comprise the same or similar orientations relative to the opening in the target tissue. For example, the first pad 330 and the third pad 360 can be on a first side of the opening while the second pad 332 and the fourth pad 362 can be on a second opposing side of the opening. In some cases, each of the pads 330, 332, 360, 362 can comprise a rectangular shape. The first and third pads 330, 360 can be positioned such that a pair of edges of one pad extend along dimensions that are collinear with corresponding edges of the other pad. In some cases, the second pad 332 and the fourth pad 362 can each comprise a rectangular shape such that a pair of edges of one pad extend along dimensions that are collinear with corresponding edges of the other pad.

Figure 4:
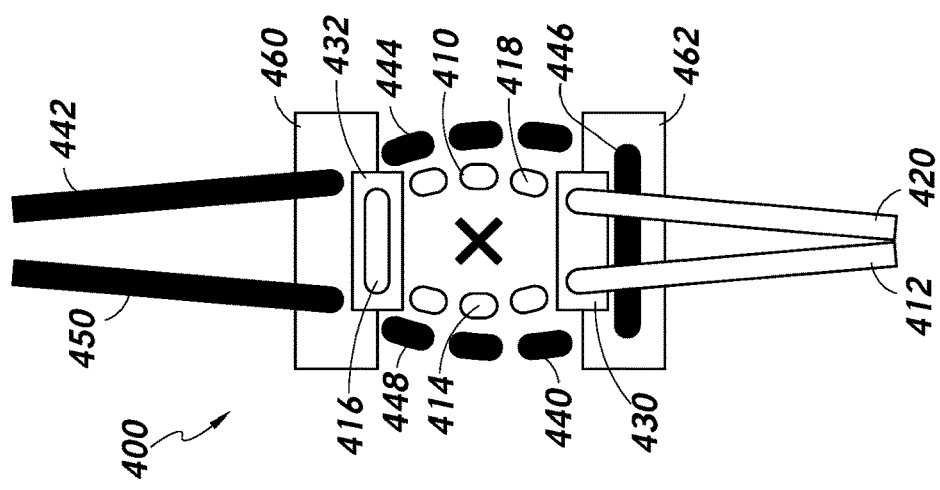
FIG. 4 is a schematic diagram of an example of a suture pattern comprising a first stitch and a second stitch both positioned around an opening in the target tissue, where the first stitch and the second stitch can have opposing orientations.

FIG. 4 shows a suture pattern 400 comprising a first stitch 410 and a second stitch 440 both positioned around an opening in the target tissue, where the first stitch 410 and the second stitch 440 can have opposing orientations. The first stitch 410 and second stitch 440 can each be formed using a single suture. The first stitch 410 and the second stitch 440 can each comprise first suture portions 412, 442, second suture portions 414, 444, third suture portion 416, 446, fourth suture portions 418, 448 and fifth suture portions 420, 450. The first suture portion 412 and fifth suture portion 420 of the first stitch 410 can both extend from the target tissue and through a first pad 430 positioned on a first side of the opening in the target tissue. The second suture portion 414 and fourth suture portion 418 can be embedded within the target tissue and extend along two opposing sides of the opening in the target tissue between the first pad 430 and a second pad 432. The second pad 432 can be at a second position around the opening opposite that of the first pad 430. The third suture portion 416 can be over the second pad 432.

The first suture portion 442 and fifth suture portion 450 of the second stitch 440 can both extend from the target tissue and through a third pad 460 positioned on the second side of the opening in the target tissue. The first suture portion 442 and fifth suture portion 450 of the second stitch 440 can extend from a position opposite that of the first suture portion 412 and fifth suture portion 420 of the first stitch 410. The third pad 460 can be positioned proximate or adjacent to the second pad 432. In some cases, the third pad 460 can have the same or similar orientation as the second pad 432. The second suture portion 444 and fourth suture portion 448 can be embedded within the target tissue and extend along two opposing sides of the opening in the target tissue between the third pad 460 and a fourth pad 462. The fourth pad 462 can be positioned on the first side of the opening. For example, the fourth pad 462 can be proximate or adjacent to the first pad 430. The third suture portion 446 can be over the fourth pad 462. In some cases, the third pad 460 can have the same or similar orientation as the second pad 432.

In some cases, the second stitch 440 can have a width and/or length longer than that of the first stitch 410 to thereby reduce or prevent undesired interaction between the two stitches. For example, a distance between portions of the first stitch 410 at opposite positions about the opening in the target tissue can be smaller than that of the portions of the second stitch 440.

Figure 5:
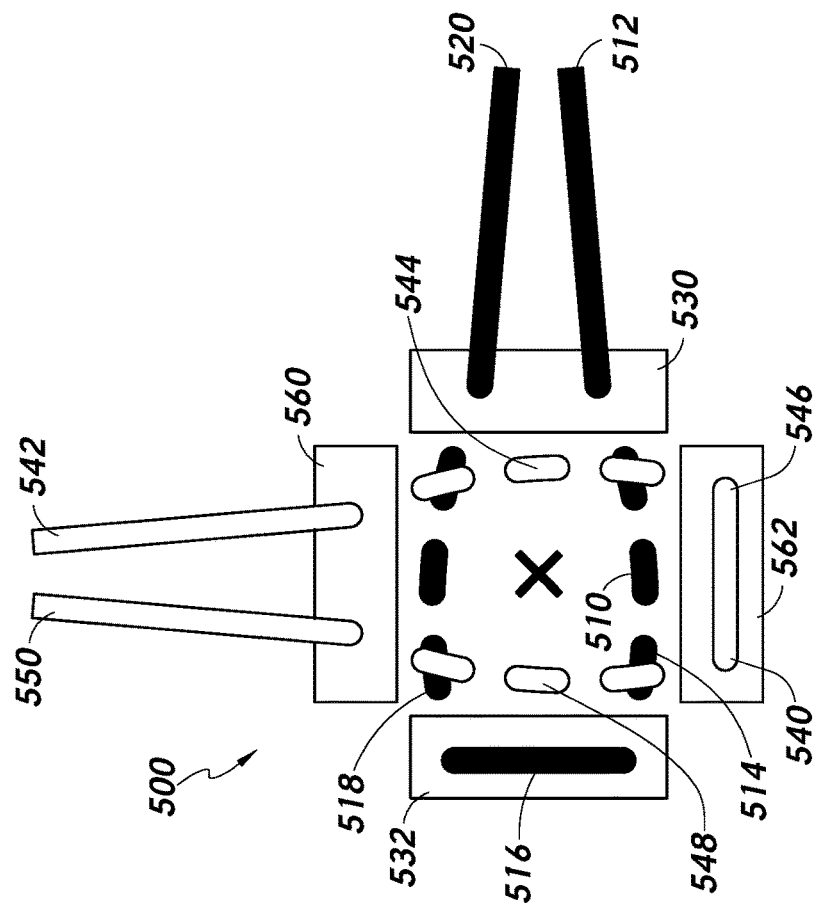
FIG. 5 is a schematic diagram of an example of a suture pattern comprising a first stitch and a second stitch both positioned around an opening in the target tissue, where the first stitch and the second stitch can have perpendicular or substantially perpendicular orientations.

FIG. 5 shows a suture pattern 500 comprising a first stitch 510 and a second stitch 540 both positioned around an opening in the target tissue, where the first stitch 510 and the second stitch 540 can have perpendicular or substantially perpendicular orientations. The first stitch 510 and second stitch 540 can each be formed using a single suture. The first stitch 510 and the second stitch 540 can each comprise first suture portions 512, 542, second suture portions 514, 544, third suture portion 516, 546, fourth suture portions 518, 548 and fifth suture portions 520, 550. The first suture portion 512 and fifth suture portion 520 of the first stitch 510 can both extend from the target tissue and through a first pad 530 positioned on a first side of the opening in the target tissue. The second suture portion 514 and fourth suture portion 518 can be embedded within the target tissue and extend along two opposing sides of the opening in the target tissue between the first pad 530 and a second pad 532. The second pad 532 can be at a second position around the opening opposite that of the first pad 530. The third suture portion 516 can be over the second pad 532.

The first suture portion 542 and fifth suture portion 550 of the second stitch 540 can both extend from the target tissue and through a third pad 560 positioned on a third side of the opening in the target tissue. The third pad 560 can have an orientation perpendicular or substantially perpendicular to that of the first pad 530 and second pad 532. For example, the first suture portion 542 and fifth suture portion 550 of the second stitch 540 can extend from a position perpendicular or substantially perpendicular to that of the first suture portion 512 and fifth suture portion 520 of the first stitch 510. The second suture portion 544 and fourth suture portion 548 can be embedded within the target tissue and extend along two opposing sides of the opening in the target tissue between the third pad 560 and a fourth pad 562. The fourth pad 562 can be positioned on a fourth side of the opening. The fourth pad 562 can be opposite that of the third pad 560. The fourth pad 562 can have an orientation perpendicular or substantially perpendicular to that of the first pad 530 and second pad 532.

Reducing or closing the opening in the target tissue using the suture patterns 200, 300, 400, 500 as described with reference to FIGS. 2 through 5 can comprise tensioning the respective first stitches 210, 310, 410, 510 and the respective second stitches 240, 340, 440, 540. For example, an operator, such as a surgeon, can pull on each of the first suture portions 212, 242, 312, 342, 412, 442, 512, 542 and fifth suture portions 220, 250, 320, 350, 420, 450, 520, 550, including pulling on the portions simultaneously. In some cases, closing the opening in the target tissue can comprise securing the stitches in the tensioned state. For example, closing the opening can comprise forming one or more knots using the first suture portions 212, 242, 312, 342, 412, 442, 512, 542 and fifth suture portions 220, 250, 320, 350, 420, 450, 520, 550, including tying the portions to one another to form the knots.

The suture patterns 200, 300, 400, 500 described with reference to FIGS. 2 through 5 can be formed using one or more suture systems described herein. A suture system can comprise a needle manipulating instrument configured to maintain a pair of curved double arm needles in a predetermined orientation relative to one another and the needle manipulating instrument. An operator, such as a surgeon, can use the pair of curved double arm needles to form the one or more suture patterns while holding the pair of curved double arm needles using the needle manipulating instrument. Controlled orientation and/or spacing of the pair of curved double arm needles can facilitate formation of uniform sutures, including improved uniformity in spacing and/or depth. Use of a needle manipulating instrument can reduce time needed to form one or more sutures for closing a target opening. For example, use of the needle manipulating instrument can enable forming one or more suture patterns as described herein (e.g., suture patterns 200, 300, 400, 500 described with reference to FIGS. 2 through 5) in about 3 to about 5 minutes. In some cases, the needle manipulating instrument can be used in combination with a needle docking device. Use of the needle manipulating instrument in combination with the needle docking can facilitate an ergonomic, safe, and efficient procedure which can require less muscular fatigue and/or strain.

In some cases, a needle manipulating instrument can comprise a surgical clamp. FIG. 6A is a perspective view of an example of a surgical clamp 600 and FIG. 6B is a more detailed view of a distal portion of the surgical clamp 600. The surgical clamp 600 can be configured to securely engage with two curved double arm needles, including while the two curved double arm needles are used to form one or more suture patterns for closing an opening in a target tissue. The surgical clamp 600 can comprise a first arm 610 and a second arm 650. A first handle 620 can be associated with a proximal portion 612 of the first arm 610 and a second handle 660 can be associated with a proximal portion 652 of the second arm 650. The first arm 610 can comprise a first distal portion 614 and the second arm 650 can comprise a second distal portion 654. An operator, such as a surgeon, can manipulate the first handle 620 and the second handle 660 to move the first distal portion 614 and the second distal portion 654 toward one another so as to engage a pair of needles. For example, a pair of curved double arm needles can be positioned between the first and second distal portions 614, 654 and the first and second distal portions 614, 654 can be moved toward one another so as to engage the pair of curved double arm needles. In some cases, the first arm 610 and the second arm 650 can be pivotally coupled to one another, such as at a pivot joint 680. For example, the operator can move the first handle 620 and the second handle 660 toward one another to pivot the first and second distal portions 614, 654 toward one another to engage the pair of needles between the first and second distal portions 614, 654. The pivot joint 680 can have any number of configurations, such as a joint which allows the first arm 610 to rotate around the joint in a first plane and the second arm 650 to rotate around the hinge in a second plane. In some cases, the pivot joint 680 can comprise a hinge.

In some cases, the first arm 610 and the second arm 650 can have a fixed predetermined length. In some cases, a length of each of the first arm 610 and the second arm 650 can be adjustable. For example, the first arm 610 and the second arm 650 can be configured to allow extension and/or shortening to a desired length to facilitate manipulation by the operator. In some cases, the length of each of the first arm 610 and the second arm 650 can be adjusted based on patient anatomy to facilitate manipulation of the pair of curved double arm needles.

Referring to FIG. 6B, the first distal portion 614 can comprise a first curvature 630 and the second distal portion 654 can comprise and a second curvature 670. The first distal portion 614 can comprise a first distal perpendicular portion 634 distal of, and a first proximal perpendicular portion 632 proximal of, the first curvature 630. The second distal portion 654 can comprise a second distal perpendicular portion 674 distal of, and a second proximal perpendicular portion 672 proximal of, the second curvature 670. The first distal perpendicular portion 634 can be perpendicular or substantially perpendicular to the first proximal perpendicular portion 632. The first distal perpendicular portion 634 can extend along an axis which is perpendicular or substantially perpendicular to that along which the first proximal perpendicular portion 632 extends. The second distal perpendicular portion 674 can be perpendicular or substantially perpendicular to the second proximal perpendicular portion 672. The second distal perpendicular portion 674 can extend along an axis which is perpendicular or substantially perpendicular to that along which the second proximal perpendicular portion 672 extends.

One or both of the first distal portion 614 and the second distal portion 654 can have, on a surface facing the other arm, two recesses each configured to receive a corresponding portion of a curved double arm needle. The first distal portion 614 can comprise a first surface 636 oriented toward the second distal portion 654. The first surface 636 can comprise thereon a first recess 640 and a second recess 642, each of the recesses being configured to receive a portion of a corresponding curved double arm needle. The first recess 640 and the second recess 642 can be on the first distal perpendicular portion 634. In some cases, the first and second recesses 640, 642 can extend along a width dimension of the first distal perpendicular portion 634. For example, the first and second recesses 640, 642 can extend along an entire width of the first distal perpendicular portion 634. In some cases, the first and second recesses 640, 642 can extend along a dimension of the first distal perpendicular portion 634 perpendicular or substantially perpendicular to an axis along which the first distal perpendicular portion 634 extends.

The first and second recesses 640, 642 can be a predetermined distance apart based on a desired separation distance between the curved double arm needles when the needles are used to suture the opening in the target tissue. A distance between suture portions forming a suture pattern can depend on the separation distance between the curved double arm needles. For example, a distance between suture portions forming a stitch can depend on the separation distance between the curved double arm needles (e.g., a distance between respective second suture portions 214, 244, 314, 344, 414, 444, 514, 544 and fourth suture portions 218, 248, 318, 348, 418, 448, 518, 548, of the suture patterns 200, 300, 400, 500 described with reference to FIGS. 2, 3, 4 and 5). Using FIG. 2, as an example, the separation distance between the curved double arm needles can depend on a desired distance between the second suture portion 214 and the fourth suture portion 218 of the first stitch 210, and/or between the second suture portion 244 and the fourth suture portion 248 of the second stitch 240.

As described in further detail herein, a shape and/or size of each of the first and second recesses 640, 642 can be configured to receive a predetermined portion of the respective curved double arm needles so as to form sutures of a predetermined size and/or depth. For example, a width and/or a depth of each of the recesses can be selected such that each of the recesses are configured to receive a predetermined portion of a curved double arm needle such that the curved double arm needle can be positioned to form a suture having a desired depth within the target tissue.

The second distal portion 654 can comprise a second surface (not shown) oriented toward the first distal portion 614. In some cases, the second surface can comprise thereon a first recess and a second recess, each of the recesses being configured to receive a portion of a corresponding curved double arm needle. The first and second recesses of the second distal portion 654 can be on the second distal perpendicular portion 674. Recesses on the second distal perpendicular portion 674 can have one or more features of the recesses 640, 642 on the first distal perpendicular portion 634. For example, the recesses can extend along a dimension of the second distal perpendicular portion 674 perpendicular or substantially perpendicular to an axis along which the second distal perpendicular portion 674 extends, including a width dimension of the second distal perpendicular portion 674. A distance between the first and second recesses can be a predetermined based on a desired separation distance between the curved double arm needles received therein. In some cases, a shape and/or size of each of the first and second recesses can be configured to receive a predetermined portion of the respective curved double arm needles so as to form sutures of a predetermined depth.

One or both of the first and second distal portions 614, 654 can comprise thereon two recesses for receive corresponding portions of a first and second curved double arm needle. In some cases, both the first and second distal portions 614, 654 can comprise two recesses thereon. Each of the first and second distal perpendicular portions 634, 674 can comprise thereon two recesses configured to receive the needles. For example, the first distal perpendicular portion 634 can comprise the first and second recesses 640, 642 and the second distal perpendicular portion 674 can comprise a third and fourth recesses. The first recess 640 and the third recess can be at a same or similar position on the respective distal perpendicular portion, and the second recess 642 and the fourth recess can be a same or similar position on the respective distal perpendicular portion. Respective portions of the curved double arm needles can be received within the space formed by the recesses. A portion of a first curved double arm needle can received within the first recess 640 and third recess. A portion of a second curved double arm needle can be received with the second recess 642 and fourth recess. The first and second distal portions 614, 654 can be pivoted toward one another such that corresponding portions of the first and second curved double arm needles can be received and sandwiched between the first and second distal perpendicular portions 634, 674 while positioned in the recesses. The recesses can be sized and shaped such that the first and second double arm needles do not rotate and/or slide relative to the surgical clamp 600 such that the needles can be maintained in predetermined orientations relative to one another and to the surgical clamp 600. The curved double arm needles can be securely pinched by the first and second distal perpendicular portions 634, 674. In some cases, positioning corresponding portions of the double arm needles in the spaces provided by the recesses can prevent or reduce damage to the double arm needles, such as by reducing or eliminating abrasion of the needles by the surgical clamp 600. Reducing or eliminating damage to the needles can reduce or prevent damage to the target tissue through which the needles are advanced.

As described herein, in some cases, the target tissue can comprise heart wall tissue, including left ventricular wall tissue. In some cases, the target tissue can be tissue of another type of organ. In some cases, the size and/or shape of the recesses of the surgical clamp 600 can be predetermined based on the size and/or shape of the portions of the needles configured to be received within the recesses. The size and/or shape of the needles can be predetermined based on the type of target tissue.

In some cases, the first surface 636 can comprise a first plurality of grooves 638. The first plurality of grooves 638 can extend along at least a portion of a length of the first distal portion 614. In some cases, the second distal portion 654 can comprise a second plurality of groves on the second surface oriented toward the first surface 636. The first plurality of grooves 638 and second plurality of grooves can facilitate stable positioning of the first distal portion 614 and the second distal portion 654 relative to one another when the first and second distal portions 614, 654 are brought together to hold the curved double arm needles.

Figure 7:
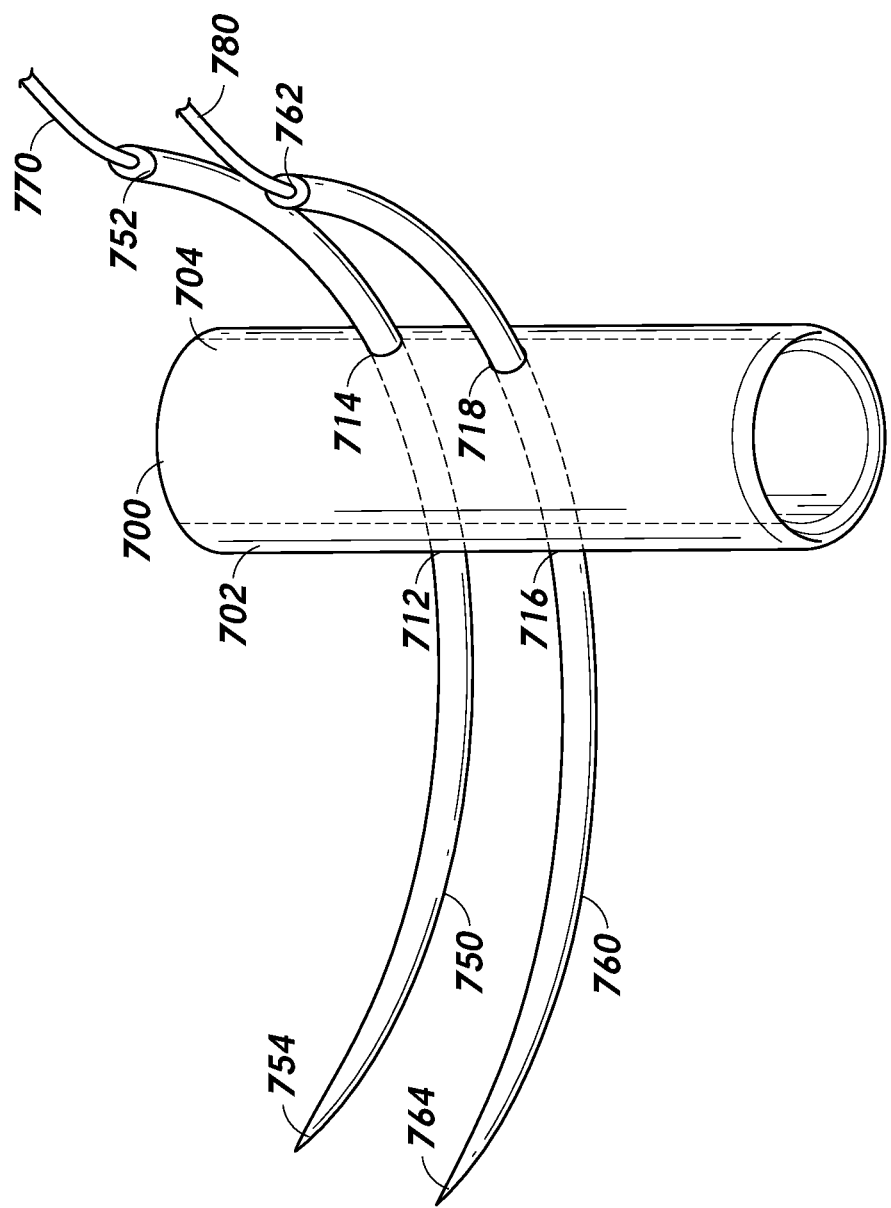
FIG. 7 is a perspective view of an example of a needle docking device, and a first curved double arm needle and a second curved double arm needle extending through the needle docking device.

As described herein, a needle docking device can be configured to maintain first and second curved double arm needles in predetermined orientations relative to one another and the needle docking device. A needle manipulating instrument can be configured to engage the first and the second curved double arm needles while the first and second curved double arm needles are held by the needle docking device. In some cases, the needle docking device can be configured to facilitate ergonomic retrieval of a pair of curved double arm needles by the needle manipulating instrument. FIG. 7 is a perspective view of an example of a needle docking device 700 and a first curved double arm needle 750 and a second curved double arm needle 760 extending through the needle docking device 700. The needle docking device 700 can be configured to maintain the first and the second curved double arm needles 750, 760 at predetermined orientations relative to one another and to the needle docking device 700. For example, the needle docking device 700 can be configured to allow a predetermined portion of the first and the second curved double arm needles 750, 760 to extend therethrough. The first and the second curved double arm needles 750, 760 can be maintained by the needle docking device 700 at a predetermined distance from, in alignment with, and parallel to one another.

The needle docking device 700 can comprise a first wall portion 702 and a second wall portion 704. The first wall portion 702 can be spaced from the second wall portion 704. The first wall portion 702 and second wall portion 704 can each comprise a pair of openings thereon through which corresponding portions of the first curved double arm needle 750 and the second curved double arm needle 760 can extend through. For example, the first wall portion 702 can have a first opening 712 and a second opening 716, and the second wall portion 704 can have a first opening 714 and a second opening 718. The first curved double arm needle 750 can extend through the first opening 712 on the first wall portion 702 and the first opening 714 on the second wall portion 704. In some cases, the first curved double arm needle 750 can have a proximal end 752 and a distal end 754. The distal end 754 can be a sharp end. The distal end 754 can be advanced through the first opening first opening 714 on the second wall portion 704 and the first opening 712 on the first wall portion 702 such that a predetermined portion of the first curved double arm needle 750 can be positioned through the needle docking device 700. The second curved double arm needle 760 can extend through the second opening 718 on the second wall portion 704 and the second opening 716 on the first wall portion 704. The second curved double arm needle 760 can comprise a proximal end 762 and a distal end 764 (e.g., a sharp end), where the distal end 764 can be advanced through the second opening 718 on the second wall portion 704 and the second opening 716 on the first wall portion 702 to position a predetermined portion of the second curved double arm needle 760 through the needle docking device 700. Respective portions of the first and second curved double arm needles 750, 760 can be disposed within the needle docking device 700. The proximal end 752 of the first curved double arm needle 750 can be coupled to a first suture portion 770 and the proximal end 762 of the second curved double arm needle 760 can be coupled to a second suture portion 780. As described in further detail herein, the first and second suture portions 770, 780 can be a part of a single suture used to form a suture stitch. The first and second suture portions 770, 780 can comprise any number of biocompatible materials. In some cases, the first and second suture portions 770, 780 can be propylene suture portions, for example, PROLENE® polypropylene suture (Ethicon, Bridgewater, New Jersey). In some cases, the first and second suture portions 770, 780 can be polytetrafluoroethylene (PTFE) suture portions.

A distance between the first and second openings 712, 716 on the first wall portion 702 and a distance between the first and second openings 714, 718 on the second wall portion 704 can be predetermined based on the desired distance between the first and second curved double arm needles 750, 760 while held by one or more needle manipulating instruments as described herein. As described in further detail herein, a needle manipulating instrument can be configured to retrieve the first and second curved double arm needles 750, 760 from the needle docking device 700. The distance between the first and second curved double arm needles 750, 760 maintained by the needle docking device 700 can be the same as the distance maintained by the needle manipulating instrument (e.g., the surgical clamps and/or needle holders as described herein) such that the needle manipulating instrument can be used to remove the first and second curved double arm needles 750, 760 from the needle docking device 700. As described herein, in some cases, the docking device can be configured to maintain the first and second double arm needles 750, 760 parallel or substantially parallel to one another. For example, the distance between the first and second openings 712, 716 on the first wall portion 702 can be the same or similar as the distance between the first and second openings 714, 718 on the second wall portion 704.

In some cases, the openings 712, 714, 716, 718 on the needle docking device 700 can be sized to receive corresponding portions of the first curved double arm needle 750 and the second curved double arm needle 760. The size of the openings 712, 714, 716, 718 can be configured such that the first and second double arm needles 750, 760 can be stably and/or securely maintained in a predetermined orientation. The openings 712, 714, 716, 718 can be sized to snuggly fit the corresponding portions of the first and second double arm needles 750, 760. For example, the first and second double arm needles 750, 760 can be securely held by the needle docking device 700 such that the first and second double arm needles 750, 760 do not undesirably rotate and/or slide relative to the needle docking device 700. In some cases, a cross-sectional size of each of the first and second curved double arm needles 750, 760 can vary along a length of the respective needles. The size of the openings 712, 714, 716, 718 can be configured to allow a predetermined portion of the first and second double arm needles 750, 760 to extend through the needle docking device 700. For example, the first and/or second double arm needle 750, 760 can comprise at least a portion which has a cross-sectional size (e.g., a diameter) which increases along a direction from the respective distal ends 754, 764 toward the respective proximal ends 752, 762. The openings 712, 714, 716, 718 on the needle docking device 700 can be sized such that the first and second curved double arm needles 750, 760 can be advanced up to a predetermined point such that a predetermined portion of the needles 750, 760 are positioned within the needle docking device 700. For example, the first opening 712 and second opening 716 on the first wall portion 702 can be smaller than the first opening 714 and second opening 718 on the second call portion 704, respectively. The distal ends 754, 764 of the first and second curved double arm needles 750, 760 can be advanced through the needle docking device 700 such that smaller first and second openings 712, 716 on the first wall portion 702 can prevent the first and second curved double arm needles 750, 760 from being advanced further through the needle docking device 700.

In some cases, the needle docking device 700 can be hollow. For example, the needle docking device 700 can have a hollow tube configuration, such as a hollow cylindrical tube. The first and second openings 712, 716, and the first and second openings 714, 718 can be on first and second wall portions 702, 704 of the hollow cylindrical tube. Although FIG. 7 shows that the needle docking device 700 can have a hollow cylindrical tube configuration, it will be understood that a needle docking device can be solid. For example, a needle docking device can have a solid cylindrical configuration. In some cases, a solid needle docking device can provide a heavier device, facilitating improved stability. The needle docking device 700 can comprise one or more of a number of materials, including polymeric and/or metallic materials. In some cases, the needle docking device 700 can comprise polypropylene. For example, the needle docking device 700 can comprise a polypropylene tubular structure.

Figure 8:
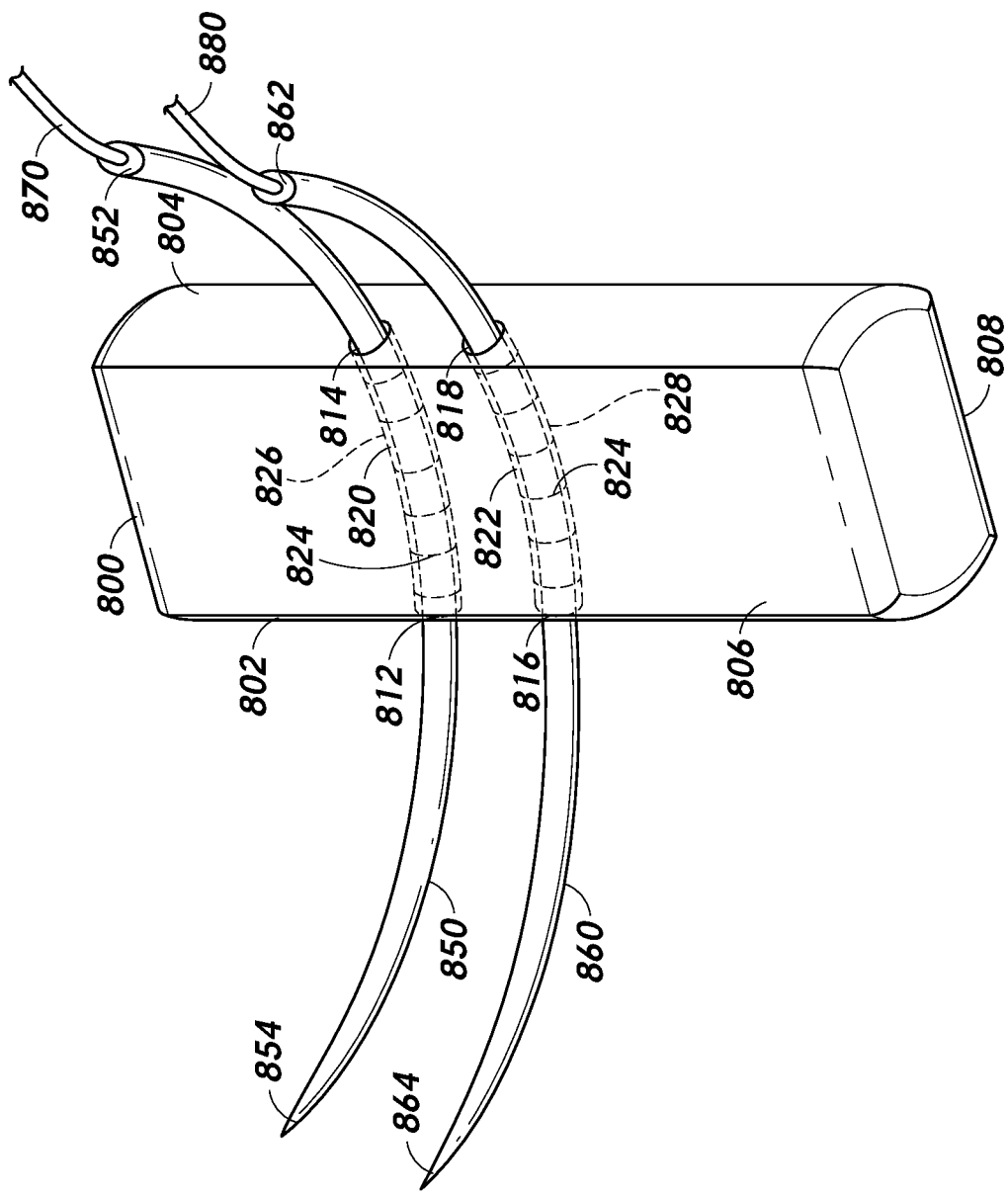
FIG. 8 is a perspective view of another example of a needle docking device, and a first and second curved double arm needles extending therethrough.

FIG. 8 is a perspective view of another example of a needle docking device 800, and first and second curved double arm needles 850, 860 extending therethrough. The needle docking device 800 can comprise a first wall portion 802 spaced from the second wall portion 804, where the first wall portion 802 can comprise a first opening 812 and a second opening 816 and the second wall portion 804 can comprise a first opening 814 and a second opening 818 through which corresponding portions of the first and second curved double arm needles 850, 860 can extend through. The first and second wall portions 802, 804 are shown as comprising a curvature, for example comprising an arcuate shape. The needle docking device 800 can comprise a first flat wall portion 806 and a second flat wall portion 808 extending between the first wall portion 802 and the second wall portion 804. For example, the first flat wall portion 806 can extend between respective first edges of the first and second wall portions 802, 804, and the second flat wall portion 808 can extending respective second edges of the first and second wall portions 802, 804. The flat wall portions 806, 808 can be facilitate stable placement of the needle docking device 800 on a flat surface.

In some cases, the needle docking device 800 can have a solid configuration. The needle docking device 800 can comprise a first lumen 820, which extends between the first opening 812 on the first wall portion 802 and the first opening 814 on the second wall portion 804, configured to allow extension therethrough of the first curved double arm needle 850. A second lumen 822 can extend between the second opening 816 on the first wall portion 802 and the second opening 818 on the second wall portion 804 to allow extension therethrough of the second curved double arm needle 860. For example, the distal end 854 of the first curved double arm needle 850 can be advanced through the first opening 814 on the second wall portion 804, the first lumen 820 and then through the first opening 812 on the first wall portion 802. The distal end 864 of the second curved double arm needle 860 can be advanced through the second opening 818 on the second wall portion 804, the second lumen 822 and then through the second opening 816 on the first wall portion 802. Proximal ends 852, 862 of the first and second curved double arm needles 850, 860 can be coupled to a first suture portion 870 and a second suture portion 880, respectively.

In some cases, respective wall portions defining the first and second lumens 820, 822 can comprise thereon features to improve contact with the first and second curved double arm needles 850, 860. The features can extend around one or more circumferential portions of the wall portions defining the lumens 820, 822. For example, the needle docking device 800 can comprise a first inner lumen surface 826 that defines the first lumen 820 and a second inner lumen surface 828 that defines the second lumen 822. The first and second inner lumen surfaces 826, 828 can each comprise engagement features 824 configured to engage with the first and second curved double arm needles 750, 760 to maintain the needles 850, 860 in a predetermined orientation. In some cases, the engagement features 824 can comprise a plurality of grooves. FIG. 8 shows the plurality of grooves extending around corresponding circumferential portions of the inner lumen surfaces 826, 828 defining the lumens 820, 822. In some cases, the engagement features 824 can comprise a plurality of grooves spaced from one another along a length of the wall portions defining the first and second lumens 820, 822.

The needle docking device 800 can have one or more of the other features of the needle docking device 700 described with reference to FIG. 7. For example, a distance between the first and second openings 812, 816 on the first wall portion 802 and a distance between the first and second openings 814, 818 on the second wall portion 804 can be predetermined based on the desired distance between the first and second curved double arm needles 850, 860 while held by one or more needle manipulating instruments as described herein. In some cases, the openings 812, 814, 816, 818 on the needle docking device 800 can be sized to receive corresponding portions of the first curved double arm needle 850 and the second curved double arm needle 860. In some cases, a cross-sectional size of each of the first and second curved double arm needles 850, 860 can vary along a length of the respective needles. The size of the openings 812, 814, 816, 818 can be configured to allow a predetermined portion of the first and second double arm needles 850, 860 to extend through the needle docking device 800. The openings 812, 814, 816, 818 on the needle docking device 800 can be sized such that the first and second curved double arm needles 850, 860 can be advanced up to a predetermined point such that a predetermined portions of the respective needles 750, 760 are positioned within the lumens 820, 822 of the needle docking device 800.

Although the needle docking devices 700, 800 described with reference to FIGS. 7 and 8 comprise one or more curved wall portions, it will be understood that a needle docking device is not so limited. In some cases, the needle docking device can comprise more or fewer curved wall portions than as shown in FIGS. 7 and 8. In some cases, the needle docking device may not comprise a curved wall portion. In some cases, the needle docking device may comprise a prismatic shape, including a rectangular prism.

Figure 9A:
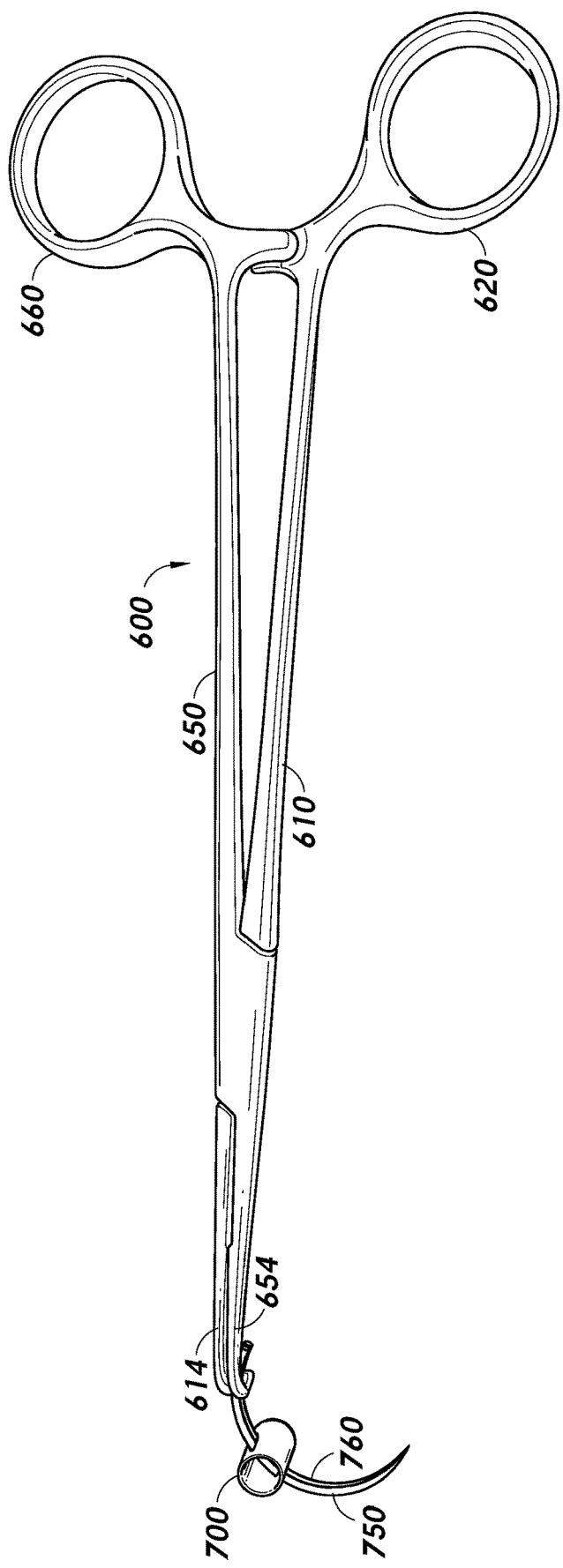
FIGS. 9A, 9B and 9C show various views of a first and second curved double arm needle engaged by the surgical clamp of FIG. 6, while the first and second curved double arm needles are received by the needle docking device of FIG. 7.
Figure 9C:
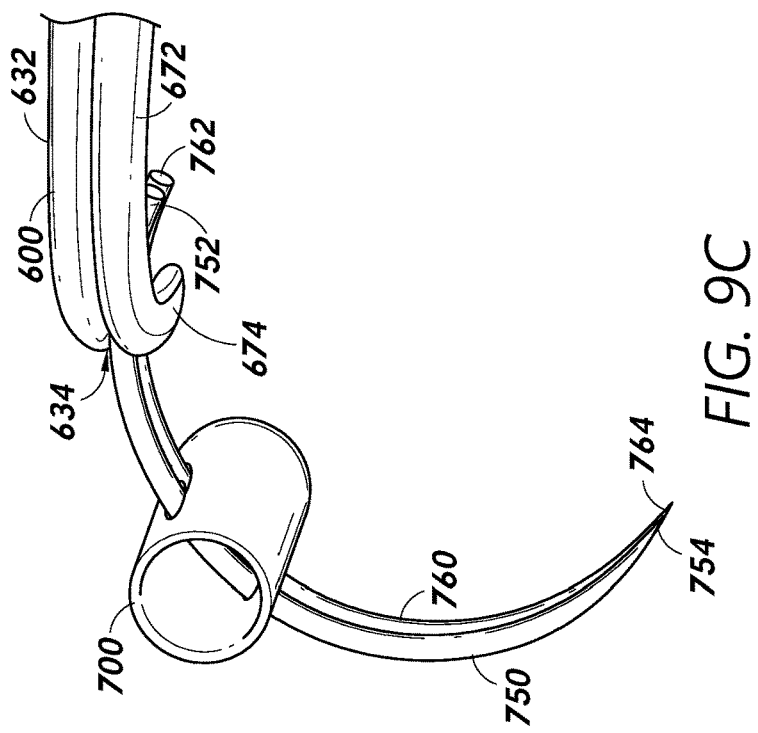
Figure 9B:
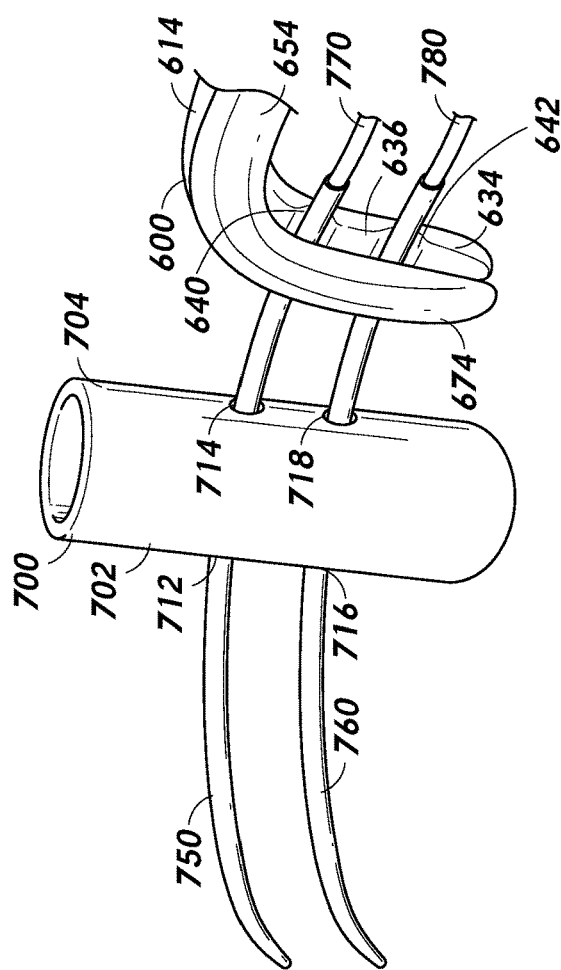

FIGS. 9A through 9C show various views of the first and second curved double arm needles 750, 760 engaged by the surgical clamp 600 described with reference to FIG. 6, while the first and second curved double arm needles 750, 760 are received by the needle docking device 700 described with reference to FIG. 7. FIG. 9A shows a perspective view which includes the entirety of the surgical clamp 600. FIG. 9B is a side perspective view, and FIG. 9C is a top perspective view, showing in further detail the engagement between the surgical clamp 600 and the first and second curved double arm needles 750, 760.

Referring to FIG. 9A, the first and second curved double arm needles 750, 760 are held by the needle docking device 700 while corresponding portions of the first and second curved double arm needles 750, 760 are engaged by the surgical clamp 600. The surgical clamp 600 can be configured to maintain the needles 750, 760 in alignment with and parallel to one another and at a predetermined orientation relative to the surgical clamp 600 while the needles 750, 760 are removed from the needle docking device 700. The first and second curved double arm needles 750, 760 can be pinched between the distal portions 614, 654 of the first arm 610 and the second arm 650 of the surgical clamp 600. An operator, such as a surgeon, can swing the first handle 620 and the second handle 660 toward one another to position the first and second curved double arm needles 750, 760 between the distal portions 614, 654.

FIG. 9B shows in more detail the engagement between the surgical clamp 600 and the first and second curved double arm needles 750, 760 positioned in the needle docking device 700. The surgical clamp 600 can be used to grip the first and second curved double arm needles 750, 760 so as to retrieve the first and second curved double arm needles 750, 760 from the needle docking device 700. As shown in FIG. 9B, the first and second curved double arm needles 750, 760 can be coupled to the first suture portion 770 and second suture portion 780, respectively, such that the first and second curved double arm needles 750, 760 can be used to form a suture in a target tissue adjacent to an opening in the target tissue.

The first and second curved double arm needles 750, 760 can be maintained between the first distal perpendicular portion 634 of the first arm 610 and the second distal perpendicular portion 674 of the second arm 650. Corresponding portions of the first and second curved double arm needles 750, 760 can be received in the first recess 640 and the second recess 642, respectively, on the first surface 636. In some cases, the surgical clamp 600 can be configured to maintain the first and second curved double arm needles 750, 760 in the same or similar orientations as that maintained by the needle docking device 700. For example, the distance between the first recess 640 and the second recess 642 can be the same or similar to the distance between the first opening 712 and the second opening 716 on the first wall portion 702, and/or between the first opening 714 and the second opening 718 on the second wall portion 704. A shape and/or size of each of the first and second recesses 640, 642 can be configured to receive a predetermined portion of the respective curved double arm needles 750, 760. As described herein, the second distal perpendicular portion 674 can comprise on a surface oriented toward the first distal perpendicular portion 634 two recesses to receive corresponding portions of the first and second curved double arm needles 750, 760. For example, the second distal perpendicular portion 674 can comprise a first recess at a similar or same position as the first recess 640 of the first distal perpendicular portion 634 such that the first recesses define a space configured to securely receive a corresponding portion of the first curved double arm needle 750. The second distal perpendicular portion 674 can comprise a second recess at a similar or same position as the second recess 642 of the first distal perpendicular portion 634 such that the second recesses define a space configured to securely receive a corresponding portion of the second curved double arm needle 760.

In some cases, a width and/or depth of the first recess 640 and the second recess 642 of the first distal perpendicular portion 634 and the first recess and the second recess of the second distal perpendicular portion 674 can be configured to allow a predetermined length of the first and the second curved double arm needles 750, 760, respectively, to be positioned therein. For example, a cross-sectional size of at least a portion of each of the first and second curved double arm needles 750, 760 can vary along a respective length of the needles. The width of each of the first recess 640 and the second recess 642 can be predetermined such that a desired portion of each of the first and second curved double arm needles 750, 760 can be received by the first and second recesses 640, 642, respectively. The portions of the respective curved double arm needles 750, 760 received within the recesses 640, 642 can be predetermined based on the lengths of the portions of the respective curved double arm needles 750, 760 extending distally beyond the surgical clamp 600. The extent to which the respective curved double arm needles 750, 760 extend beyond the surgical clamp 600 can based on, for example, a desired depth of suturing desired in the suture patterns formed.

Referring to FIG. 9C, a top perspective view is shown of the first and second curved double arm needles 750, 760 positioned in the needle docking device 700 while the first and second curved double arm needles 750, 760 are engaged by the surgical clamp 600. In some cases, while the first and second curved double arm 750, 760 are securely held by the surgical clamp 600, each of the first and second curved double arm needles 750, 760 can extend along planes parallel or substantially parallel to the planes along which the first and second proximal perpendicular portions 632, 672 extend. The distal ends 754, 764 of the first and second curved double arm needles 750, 760 can extend distally of the first and second distal perpendicular portions 634, 674. The proximal ends 752, 762 of the first and second curved double arm needles 750, 760 can extend proximally of the first and second distal perpendicular portions 634, 674. The first suture portion 770 and the second suture portion 780 are not shown in FIG. 9C for simplicity.

Figure 10A:
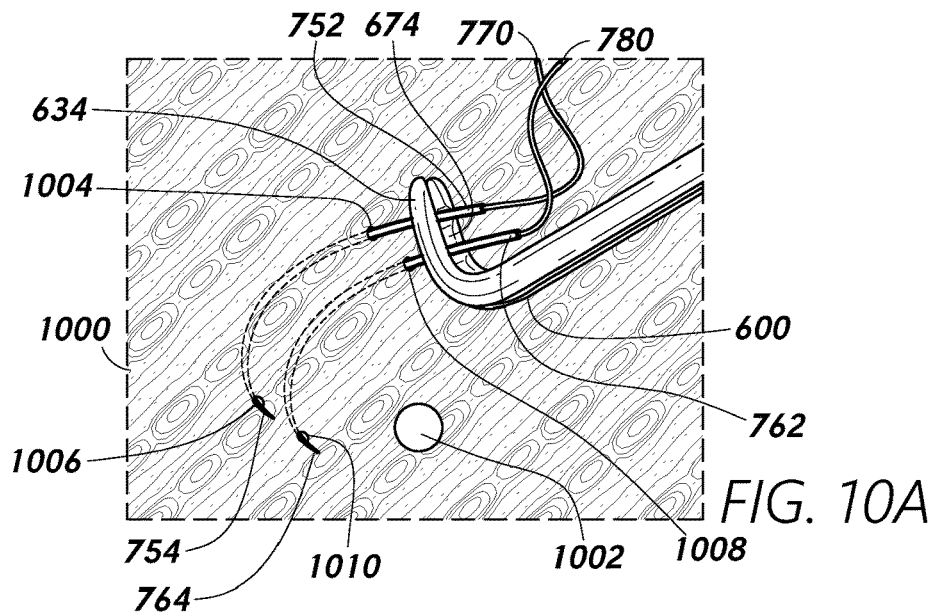
FIGS. 10A, 10B and 10C show an example of using the surgical clamp of FIG. 6 to hold a first and second curved double arm needle while forming a suture.
Figure 10B:
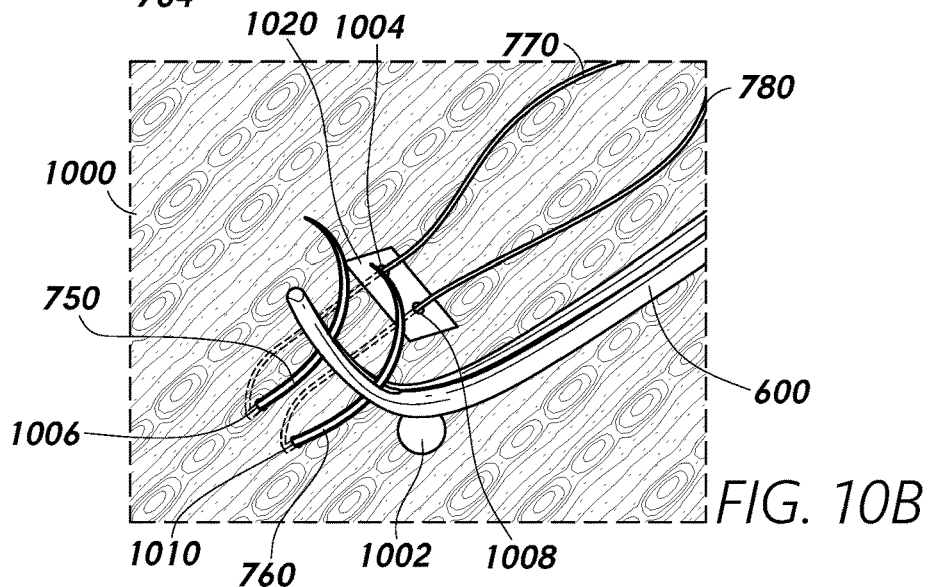
Figure 10C:
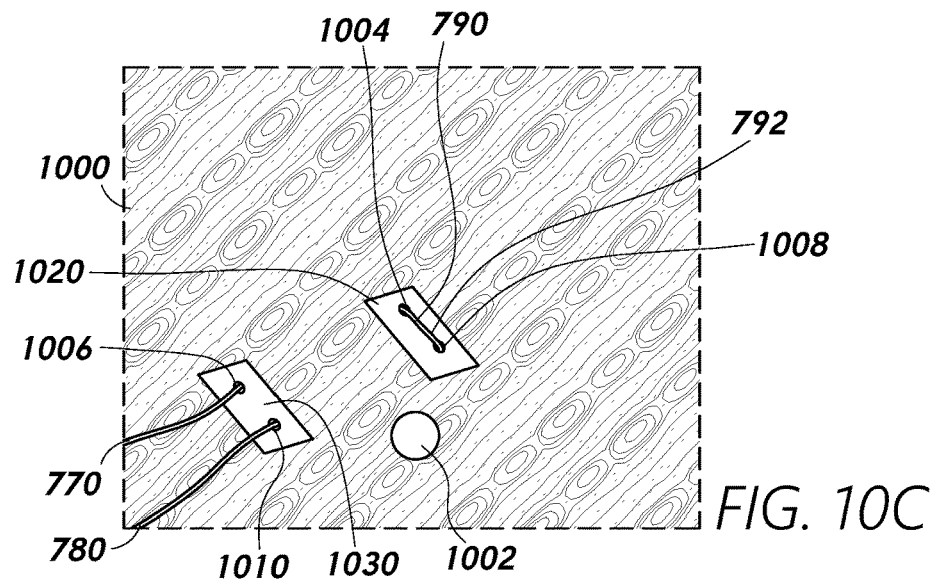

FIGS. 10A through 10C show an example of using the surgical clamp 600 to hold the first and second curved double arm needles 750, 760 while forming a suture. The first and second curved double arm needles 750, 760 can be used to form a first suture stitch to a side of an opening 1002 in a target tissue 1000. Referring to FIG. 10A, the first and second curved double arm needles 750, 760 can be positioned between the first and second distal perpendicular portions 634, 674 of the surgical clamp 600 while the needles 750, 760 are advanced through the target tissue 1000 on a first side of the opening 1002. As shown in FIG. 10A, the first suture portion 770 can be coupled to the proximal end 752 of the first curved double arm needle 750 and the second suture portion 780 can be coupled to the proximal end 762 of the second curved double arm needle 760. The first and second curved double arm needles 750, 760 can be inserted into the target tissue 1000 at respective first positions 1004, 1008 and pushed out of the target tissue 1000 at respective second positions 1006, 1010. The distal ends 754, 764 of the needles 750, 760 are shown as extending through the target tissue at the respective second positions 1006, 1010.

In FIG. 10B, the surgical clamp 600 is shown grasping corresponding portions of the first and second curved double arm needles 750, 760 which are protruding from the target tissue 1000 at the respective second positions 1006, 1010. Proximal ends 752, 762 of the needles 750, 760 coupled to the first suture portion 770 and second suture portion 780, respectively, are within the target tissue 1000. The first suture portion 770 and second suture portion 780 are shown extending from the first positions 1004, 1008, respectively. In some cases, the first and second curved double arm needles 750, 760 can be pulled through the target tissue 1000 using any number of surgical pickup tools, including forceps, clamps, and/or tweezers. For example, a surgical pickup tool can be used to engage portions of the first and second curved double arm needles 750, 760 protruding from extending from the second positions 1006, 1010 on the target tissue 1000.

FIG. 10C shows the first suture stitch 792 in the target tissue 1000 to the first side of the opening 1002. The first suture portion 770 and second suture portion 780 are shown extending from the first positions 1004, 1008, respectively. A third suture portion 790 can be positioned over the target tissue 1000 between the first positions 1004, 1008. The first, second and third suture portions 770, 780, 790 can be a part of one suture such that the first and second suture portions 770, 780 can be pulled through the target tissue 1000 to position the third suture portion 790 over the target tissue 1000.

In some cases, one or more pads can be used in forming the suture. For example, a first pad 1020 can be positioned over the first positions 1004, 1008 and target tissue 1000 adjacent to the first positions 1004, 1008. The third suture portion 790 can be positioned over the first pad 1020. The first pad 1020 can be coupled to the suture prior to insertion of the first and second curved double arm needles 750, 760 into the target tissue. In some cases, the first and second curved double arm needles 750, 760 can be threaded through the first pad 1020, and corresponding portions of the suture coupled to the suture can be threaded through the first pad 1020, such that the third suture portion 790 is positioned over a surface of the first pad 1020. In some cases, the first pad 1020 can comprise a pair of pre-formed openings, such as pre-punched holes, configured to allow threading therethrough of the needles 750, 760 and corresponding portions of the suture.

A second pad 1030 can be positioned over the second positions 1006, 1010 and target tissue 1000 adjacent to the second positions 1006, 1010. The first and second suture portions 770, 780 can extend through the second pad 1030. In some cases, the pads 1020, 1030 can reduce or prevent abrasion of the target tissue 1000 by the suture portions. The first and second suture portions 770, 780 can be tensioned to facilitate reducing the size of the opening 1002, such as to effect closure of the opening 1002. After desired closing of the opening 1002 is achieved, the positions of the first and second suture portions 770, 780 can be fixed to maintain the closure of the opening 1002. For example, the first and second suture portions 770, 780 can be tied to one another to maintain the closure of the opening 1002, such as to maintain hemostasis.

In some cases, a second suture stitch can be formed to a second side of the opening 1002. For example, a second suture stitch can be formed on an opposing side of the opening 1002. The second suture stitch can have the same or different orientation as the first suture stitch 792. In some cases, the second suture stitch can have the same orientation as the first suture stitch 792, for example forming the suture pattern 300 described with reference to FIG. 3. In some cases, the second suture stitch and the first suture stitch 792 can have opposing orientations, for example forming the suture pattern 200 described with reference to FIG. 2.

In some cases, the first and second curved double arm needles 750, 760 can be positioned one to each of two sides of an opening in a target tissue to form a first suture stitch. A second suture stitch can be formed using the first and second curved double arm needles 750, 760, where the first and second curved double arm needles 750, 760 can be positioned one to each of two sides of an opening in a target tissue to form a first suture stitch. In some cases, the first and second curved double arm needles 750, 760 can be inserted into the target tissue on the same two sides to form the two suture stitches, such as to form the suture pattern 400 as described with reference to FIG. 4. A distance between the first and second curved double arm needs 750, 760 can be changed between forming the first suture stitch and the second suture stitch such that the first and second suture stitches can have different widths. For example, clamps configured to hold the first and second curved double arm needles 750, 760 at different distances from one another can be used. In some cases, the first and second curved double arm needles 750, 760 can be inserted into the target tissue on a first side and a second side, respectively, to form the first suture stitch. The first and second curved double arm needles 750, 760 can be inserted into the target tissue on a third side and a fourth side, respectively, to form the second suture stitch. In some cases, the first and third sides, and second and fourth sides, can be perpendicular or substantially perpendicular to one another, such as the suture pattern 500 as described with reference to FIG. 5.

FIGS. 11A through 11D show various views of another example of a needle manipulating instrument, a needle holder 1100. The needle holder 1100 can comprise a proximal handle 1140 and a shaft portion 1110 extending distally from the proximal handle 1140. The shaft portion 1110 can comprise a first shaft 1120 and a second shaft 1130. The first shaft 1120 can comprise a first proximal portion 1122 and a first distal portion 1124. The second shaft 1130 can comprise a second proximal portion 1132 and a second distal portion 1134. A proximal end 1126 of the first shaft 1120 and a proximal end 1136 of the second shaft 1130 can be coupled to the proximal handle 1140. Each of the first shaft 1120 and second shaft 1130 can comprise a lumen extending through at least the respective first and second distal portions 1124, 1134. Each of the lumens can extend to respective distal ends 1128, 1138 of the first shaft 1120 and second shaft 1130. For example, a first lumen of the first shaft 1120 and a second lumen of the second shaft 1130 can comprise therein corresponding needle engagement features configured to engage the first and second curved double arm needles 750, 760, respectively. The first shaft 1120 and the second shaft 1130 can be linear or substantially linear. As described in further detail herein, in some cases, a needle holder can comprise a non-linear shaft portion, for example comprising a curvature in the shaft portion. In some cases, the first shaft 1120 and the second shaft 1130 can each have a cylindrical shape. It will be understood that the first shaft 1120 and the second shaft 1130 can have a shape other than cylindrical shape. In some cases, the first shaft 1120 and the second shaft 1130 can each have a prismatic shape.

Figure 11D:
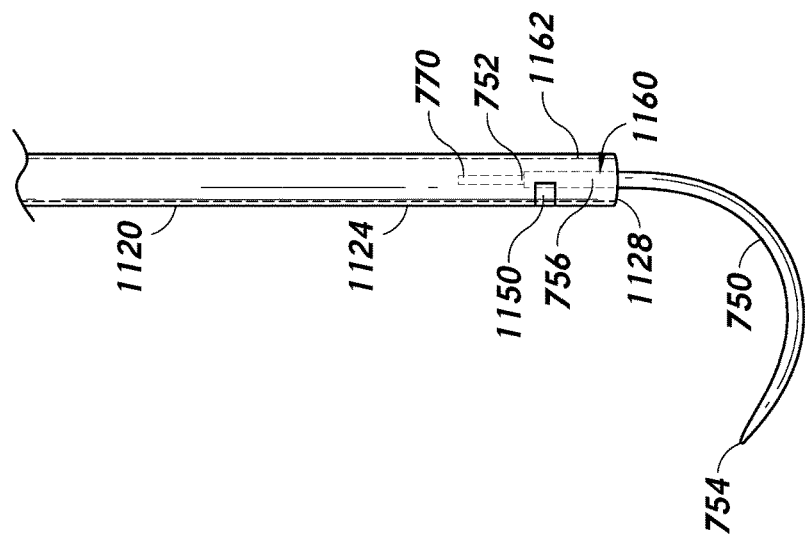
Figure 11C:
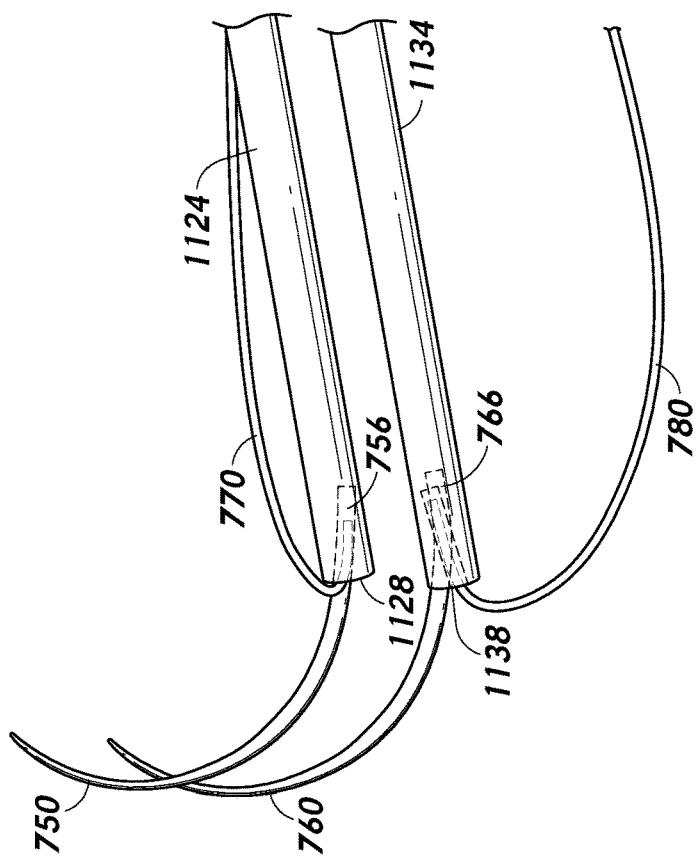

FIGS. 11B and 11C show the distal portion 1124 of the first shaft 1120 and the distal portion 1134 of the second shaft 1130 in further detail. FIG. 11B shows a portion of each of the first suture portion 770 extending from the distal end 1128 of the first distal portion 1124 and the second suture portion 780 extending from the distal end 1138 of the second distal portion 1134. A proximal portion 756, including the proximal end 752, of the first curved double arm needle 750 can be inserted into the distal end 1128 of the first shaft 1120 and into the first lumen. The first suture portion 770 can be coupled to the proximal end 752 of the first curved double arm needle 750 and the second suture 780 portion can be coupled to the proximal end 762 of the second curved double arm needle 760. A proximal portion 766, including the proximal end 762 of the second curved double arm needle 760 can be inserted into the distal end 1138 of the second shaft 1130 and into the second lumen. The proximal portions 756, 766 of the first and second curved double arm needles 750, 760, and portions of the first and second suture portion 770, 780, positioned within the first and second distal portions 1124, 1134 are shown in FIG. 11C.

FIG. 11D is a side view of the interior of the first distal portion 1124 of the first shaft 1120. The first lumen 1160 is shown. The first lumen 1160 can extend at least within a portion of the first distal portion 1124 and open to the distal end 1128. In some cases, the first lumen 1160 can extend along an entire or substantially an entire length of the first shaft 1120. A needle engagement feature 1150 configured to engage with the first curved double arm needle 750 can be within the first lumen 1160. In some cases, the needle engagement feature 1150 can be associated with, for example extending from, a wall portion 1162 defining the first lumen 1160. As shown in FIG. 11D, the first curved double arm needle 750 can comprise a portion positioned within the first lumen 1160. For example, at least a portion of the proximal portion 756, including the proximal end 752, of the needle 750 can be inserted within the first lumen 1160. The needle engagement feature 1150 can engage with a corresponding portion of the first curved double arm needle 750 within the first lumen 1160. For example, the needle engagement feature 1150 can be configured to engage with a portion of the proximal portion 756 of the needle 750 to maintain the needle 750 in a predetermined orientation relative to the needle holder 1100.

The first suture portion 770 can be coupled to the proximal end 752 of the first curved double arm needle 750. The first suture portion 770 can comprise at least a portion positioned within the first lumen 1160. For example, the first suture portion 770 can be bent within the first lumen 1160 such that the first suture portion 770 extends back out of the first lumen 1160 at the distal end 1128. Note that the bend in the first suture portion 770 is omitted in FIG. 11D for simplifying the figure.

As described herein, a predetermined portion of the first curved double arm needle 750 can be positioned within the first lumen 1160 based on a desired depth of a suture stitch formed using the needle 750. For example, a predetermined portion of the proximal portion 756 can be within the first lumen 1160 such that the distal end 754 of the first curved double arm needle 750 can be at a predetermined position distal of the distal end 1128 of the first shaft 1120. The position of the distal end 754 relative to the distal end 1128 of the first shaft 1120 can determine the trajectory of the first curved double arm needle 750 as it is inserted into the target tissue, for example thereby determining the depth of the suture stitch formed using the first curved double arm needle 750.

The second shaft 1130 can comprise one or more features of the first shaft 1120. In some cases, the second shaft 1130 can comprise the same features as the first shaft 1120. The second shaft 1130 can comprise a needle engagement feature extending from a wall portion of the second lumen and configured to engage with the second curved double arm needle 760. The needle engagement feature can be configured to engage with a portion of the proximal portion 766 of the needle 760 to maintain the needle 760 in a predetermined orientation relative to the needle holder 1100. In some cases, a predetermined portion of the proximal portion 766 can be within the second lumen such that the distal end 764 of the second curved double arm needle 760 can be at a predetermined position distal of the distal end 1138 of the second shaft 1130.

The needle engagement feature can have any number of configurations, including a clip which allows a corresponding portion of a curved double arm needle to be snapped into place. In some cases, the needle engagement feature can comprise one or more of a press-fit, snap-fit, and/or clamp engagement feature.

Figure 12:
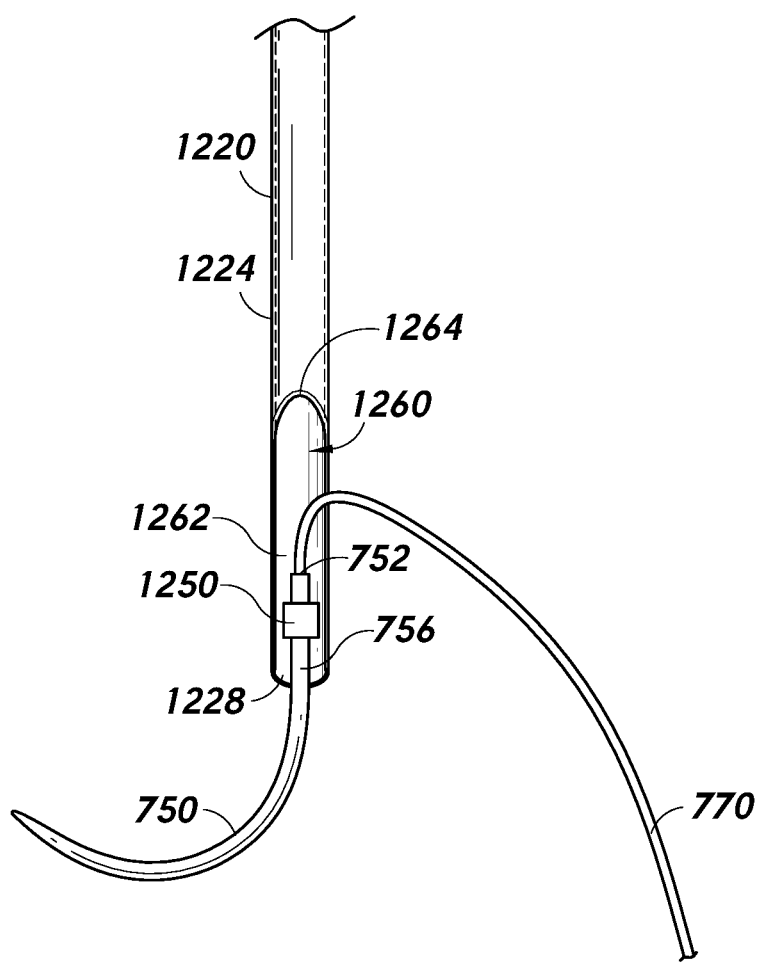
FIG. 12 is a side view of another example of a shaft of a needle holder, where the shaft can comprise a side opening on a distal portion.

FIG. 12 is a side view of another example of a shaft 1220 of a needle holder, where the shaft 1220 can comprise a side opening 1264 on a distal portion 1224 in communication with a lumen 1260 extending through at least a portion of the distal portion 1224. For example, the side opening 1264 can be on a portion of the wall 1262 defining the lumen 1260. In some cases, the lumen 1260 can extend along an entire or substantially an entire length of the first shaft 1220. The lumen 1260 can open to a distal end 1228 of the shaft 1220. A needle engagement feature 1250 can be associated with, for example extending from, a portion of the wall 1262 defining the lumen 1260. The first curved double arm needle 750 can comprise a portion positioned within the lumen 1260. For example, at least a portion of the proximal portion 756, including the proximal end 752, of the needle 750 can be inserted within the lumen 1260. The needle engagement feature 1250 can engage with a corresponding portion of the first curved double arm needle 750 within the lumen 1260 to maintain the needle 750 in a predetermined orientation. A predetermined portion of the first curved double arm needle 750 can be positioned within the lumen 1260 based on a desired depth of sutures formed using the needle 750 while engaged by the shaft 1220. As shown in FIG. 12, the first suture portion 770 can be coupled to the proximal end 752 of the first curved double arm needle 750. The first suture portion 770 can comprise at least a portion positioned within the lumen 1260 and the remaining portion of first suture portion 770 can extend through the side opening 1264. In some cases, the side opening 1264 can facilitate positioning of the first curved double arm needle 750 into engagement with the needle engagement features 1250, and/or reduce or prevent stress exerted upon the first suture portion 770 due to bending of the suture portion if loaded into a shaft without a side opening.

In some cases, a needle holder can comprise two shafts each comprising the features of the shaft 1220. For example, a needle holder can comprise a first shaft and a second shaft, each comprising a side opening along a portion of the wall defining a respective lumen of the shaft. The side opening can allow extension therethrough of a suture coupled to the respective proximal portions of the first and second curved double arm needles.

Figure 13A:
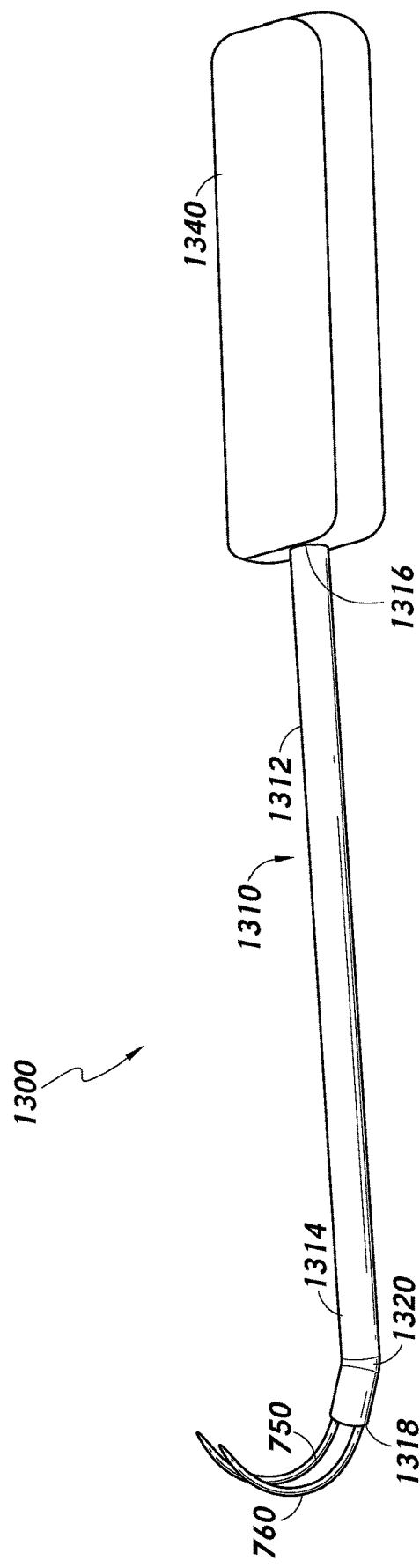
FIGS. 13A and 13B are perspective views of examples of needle holders, where a shaft portion of the needle holders can comprise a curvature.

FIG. 13A is a perspective view of an example of a needle holder 1300 comprising a curvature 1320 in a shaft portion 1310. The needle holder 1300 can comprise a proximal handle 1340. The shaft portion 1310 can extend distally from the proximal handle 1340. For example, a proximal end 1316 of the shaft portion 1310 can be coupled to the proximal handle 1340. In alternative cases, the needle holder 1300 can comprise two distinct shafts, each shaft comprising a curvature thereon. The needle holder 1300 can include one shaft portion 1310, rather than two distinct shafts. The shaft portion 1310 can comprise a curvature 1320 thereon, such as for ergonomic purposes, to facilitate access to the target site. Although FIG. 13 shows the curvature 1320 on a distal portion 1314 of the shaft portion 1310, it will be understood that the curvature 1320 can be on a proximal portion 1312 of the shaft portion 1310.

Figure 13B:
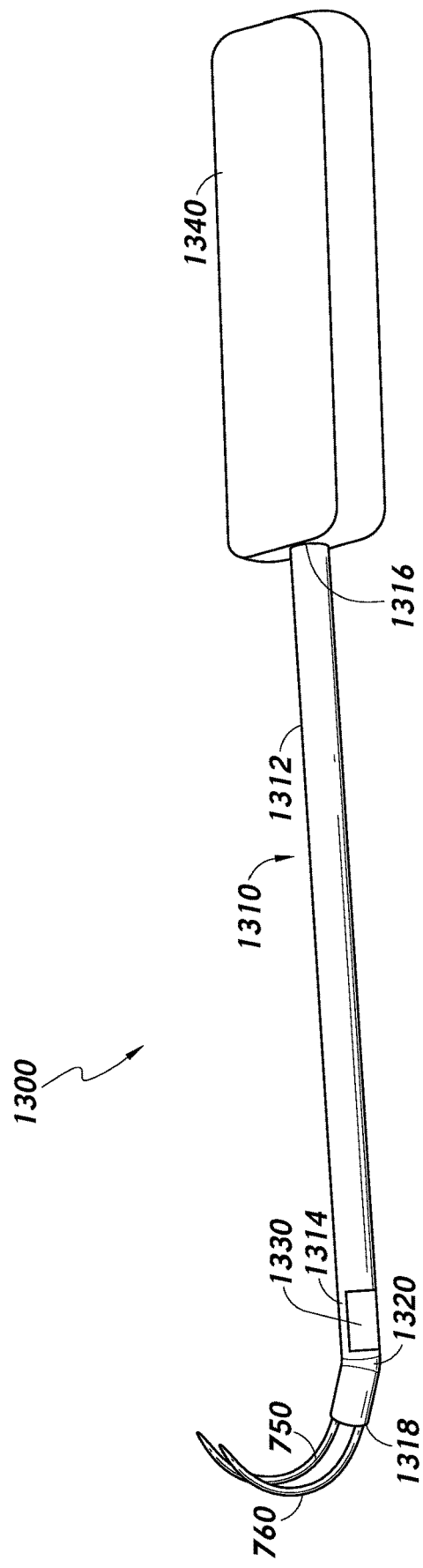

FIG. 13B is a perspective view of another embodiment of the needle holder 1300 comprising the curvature 1320 in the shaft portion 1310, where the curvature 1320 can be adjustable. For example, the needle holder 1300 can comprise a curvature adjustment component 1330 configured to adjust the position of a portion of the shaft portion 1310 distal of the curvature 1320 relative to a portion of the shaft portion 1310 proximal of the curvature 1320. The curvature adjustment component 1330 can be configured to allow the portion of the shaft portion 1310 distal of the curvature 1320 to rotate relative to the portion of the shaft portion 1310 proximal of the curvature 1320 so as to adjust the angle formed by the two portions. For example, the curvature adjustment component 1330 can be configured to allow rotation of the portion distal of the curvature 1320 within one or more predetermined plane relative to the portion proximal of the curvature 1320. The curvature adjustment component 1330 can be configured to maintain the curvature 1320 in a desired configuration, such as after adjustment has been made. In some cases, an operator, such as a surgeon, can manipulate the curvature adjustment component 1330 to a desired angle, such as based on patient anatomy. The curvature adjustment component 1330 can comprise any number of mechanisms, including a ratchet. In some cases, the portion distal of the curvature 1320 can be rotated about an axis perpendicular or substantially perpendicular to a longitudinal axis of the shaft 1310 such that the distal end 1318 of the shaft 1310 be closer or further away from the proximal end 1316 of the shaft 1310 (e.g., side-to-side or up-and-down). In some cases, the portion distal of the curvature 1320 can be rotated about the longitudinal axis of the shaft 1310.

The needle holder 1300 can be configured to engage corresponding portions of the first and second curved double arm needles 750, 760. Both a first lumen and a second lumen can extend at least within a portion of the distal portion 1314 and can open to a distal end 1318 of the shaft portion 1310. Each of the first lumen and second lumen can comprise therein a respective needle engagement feature configured to receive a corresponding curved double arm needle, such as the first curved double arm needle 750 and second curved double arm needle 760.

The needle holder 1300 can comprise one or more other features of the needle holder 1100 described with reference to FIG. 11. For example, the needle engagement feature can comprise one or more characteristics of the needle engagement feature 1150. In alternative cases, the needle holder 1300 can comprise a side opening along a portion of the wall defining a respective lumen of the shaft. The side opening can allow extension therethrough of a suture coupled to the respective proximal portions of the first and second curved double arm needles.

Figure 14C:
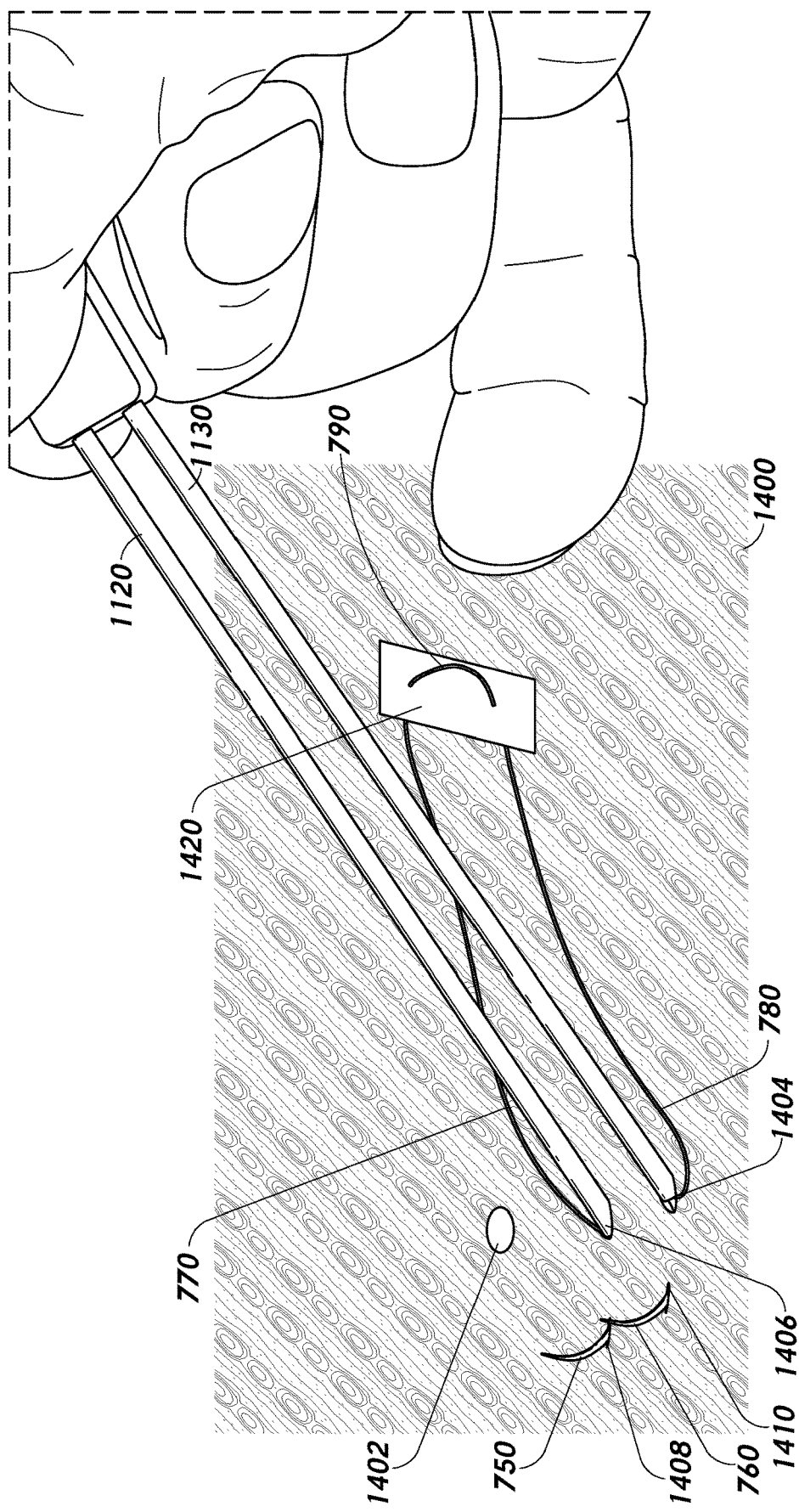

FIGS. 14A through 14C show various steps of using the needle holder 1100 to hold the first and second curved double arm needles 750, 760 in forming a suture in a target tissue 1400 adjacent to an opening 1402 in the target tissue 1400. FIG. 14A shows an operator, such as a surgeon, holding the proximal handle 1140 of the needle holder 1100. The first and second curved double arm needles 750, 760 can extend from distal ends 1128, 1138 of the first shaft 1120 and second shaft 1130. The first suture portion 770 and second suture portion 780 can be coupled to the first and second curved double arm needles 750, 760, respectively. The first suture portion 770 and second suture portion 780 can extend out from the distal ends 1128, 1138 of the first shaft 1120 and second shaft 1130, respectively.

In FIG. 14B, the first and second curved double arm needles 750, 760 are shown as being advanced into the target tissue 1400 at first positions 1404, 1406, while engaged by the needle holder 1100. The distal ends 754, 764 of the needles 750, 760 are shown as extending from second positions 1408, 1410 on the target tissue 1400. FIG. 14C shows a zoomed out view of the first and second curved double arm needles 750, 760 inserted into the target tissue 1400. A first pad 1420 is shown as being coupled to the first and second suture portions 770, 780. The third suture portion 790 is shown as being over the first pad 1420. The first and second curved double arm needles 750, 760 can be further advanced through the target tissue 1400 and removed from the target tissue such that a portion of each of the first and second suture portions 770, 780 can be pulled through the target tissue 1400 to position the first pad 1420 over the first positions 1404, 1406. The third suture portion 790 can then be positioned between the first positions 1404, 1406 and over the first pad 1420. In some cases, the first and second curved double arm needles 750, 760 can be pulled through the target tissue 1400 using any number of surgical pickup tools, including forceps, clamps, and/or tweezers. For example, a surgical pickup tool can be used to engage portions of the first and second curved double arm needles 750, 760 protruding from extending from the second positions 1408, 1410 on the target tissue 1400.

The needle holder 1100 can be used to form one or more suture patterns as described herein, including suture patterns 200, 300, 400, 500, described with reference to FIGS. 2, 3, 4, and 5.

FIG. 15 is a process flow diagram of an example of a suturing process 1500. The suturing process 1500 can be performed using one or more of the needle manipulating instruments described herein. In block 1502, the suturing process 1500 can involve engaging and maintaining a first pair of curved double arm needles in alignment with and parallel to one another using a needle manipulating instrument. Engaging the first pair of curved double arm needles can comprise removing the first pair of curved double arm needles from a needle docking device.

In block 1504, the suturing process 1500 can involve inserting sharp ends of the first pair of curved double arm needles, while the first pair of curved double arm needles is held by the needle manipulating instrument, into a target tissue in an area adjacent to an opening in the target tissue to make a first stitch. In block 1506, the suturing process 1500 can involve inserting sharp ends of one of the first pair of curved double arm needles or a second pair of curved double arm needles, while the first pair or the second pair of curved double arm needles is held by the needle manipulating instrument, into the target tissue in the area adjacent to the opening to make a second stitch. In block 1508, the suturing process 1500 can involve tensioning sutures of the first stitch and the second stitch to reduce a size of the opening in the target tissue.

The needle manipulating instrument can be used to form one or more suture patterns described herein. In some cases, the needle manipulating instrument can be used to form a suture pattern comprising a stitch on each of two sides of the opening in the target tissue, such as on opposing sides of the opening. For example, inserting sharp ends of the first pair of curved double arm needles into the target tissue can comprise inserting the first pair of curved double arm needles on a first side of the opening to position the first stitch on the first side of the opening. Inserting sharp ends of the one of the first or the second pair of curved double arm needles into the target tissue can comprise inserting the one of the first or the second pair of curved double arm needles to a second side of the opening to position the second stitch parallel to and on a second side of the opening. In some cases, the first stitch and the second stitch comprise a same orientation. In some cases, the first stitch and the second stitch comprise opposing orientations.

In some cases, the needle manipulating instrument can be used to form a suture pattern comprising two stitches each having a portion on opposing sides of the opening on the target tissue. For example, inserting sharp ends of the first pair of curved double arm needles into the target tissue comprises inserting a first needle and a second needle of the first pair of curved double arm needles on a first set of opposing sides of the opening to position the first stitch on two sides of the opening, and where inserting sharp ends of the one of the first pair or second pair of curved double arm needles into the target tissue comprises inserting a first needle and a second needle of the first or second pair of curved double arm needles on a second set of opposing sides of the opening to position the second stitch on two sides of the opening. In some cases, the two sutures can be perpendicular or substantially perpendicular. In some cases, the two sutures can have opposing or substantially opposing orientations. For example, the first and second opposing sides are the same set of opposing sides, where suture portions of the first stitch are outside of suture portions of the second stitch, and wherein the first stitch and the second stitch have opposing orientations.

In some cases, engaging and maintaining the first pair of curved double arm needles in alignment with and parallel to one another using the needle manipulating instrument can comprise pivoting a first distal portion of a first arm toward a second distal portion of a second arm of the needle manipulating instrument. The first distal portion and the second distal portion can each comprise a first curvature and a second curvature, respectively. The first arm can comprise a portion distal of the first curvature extending along a first axis perpendicular to that along which a portion proximal of the first curvature extends. The second arm comprises a portion distal of the second curvature extending along a second axis perpendicular to that along which a portion proximal of the second curvature extends. A first and a second needle of the first pair of curved double arm needles can be positioned within a first recess and a second recess on a surface of the first arm oriented toward the second arm and distal of the first curvature, respectively, to fixate the first pair of needles between the first arm and second arm. In some cases, the first and the second needle of the first pair of curved double arm needles can be positioned within a first recess and a second recess on a surface of the second arm oriented toward the first arm and distal of the second curvature, respectively, to fixate the first pair of needles between the first arm and second arm.

In some cases, engaging and maintaining the first pair of curved double arm needles in alignment with and parallel to one another using the needle manipulating instrument can comprise inserting respective proximal portions of a first and second needle of the first pair of curved double arm needles into a first and a second lumen of a shaft portion of the needle manipulating instrument, respectively. Proximal portions of the first and second needle can be engaged with respective needle engagement feature positioned within each of the first and second lumens.

In some cases, proximal ends of each needle of the first pair of curved double arm needles can be coupled to one another via a suture. Each needle of the first pair of curved double arm needles can be threaded through corresponding openings of a pad to position a portion of the suture over the pad.

Tensioning of traditional purse-string sutures to close an opening in a target tissue can result in damage to portions of tethers extending through the opening, for example including abrasive damage to and/or breakage of the tethers. Tensioning of traditional purse-string sutures can cause undesired folding of the target tissue proximate and/or adjacent to the opening and/or movement of the purse-string sutures through the target tissue. Folding of the tissue and movement of the purse-string sutures through the tissue can in turn result in abrasion and/or breakage of the tethers. Described herein are systems, devices and methods relating to an improved suturing structure configured to reduce or eliminate damage to the tethers.

Figure 16A:
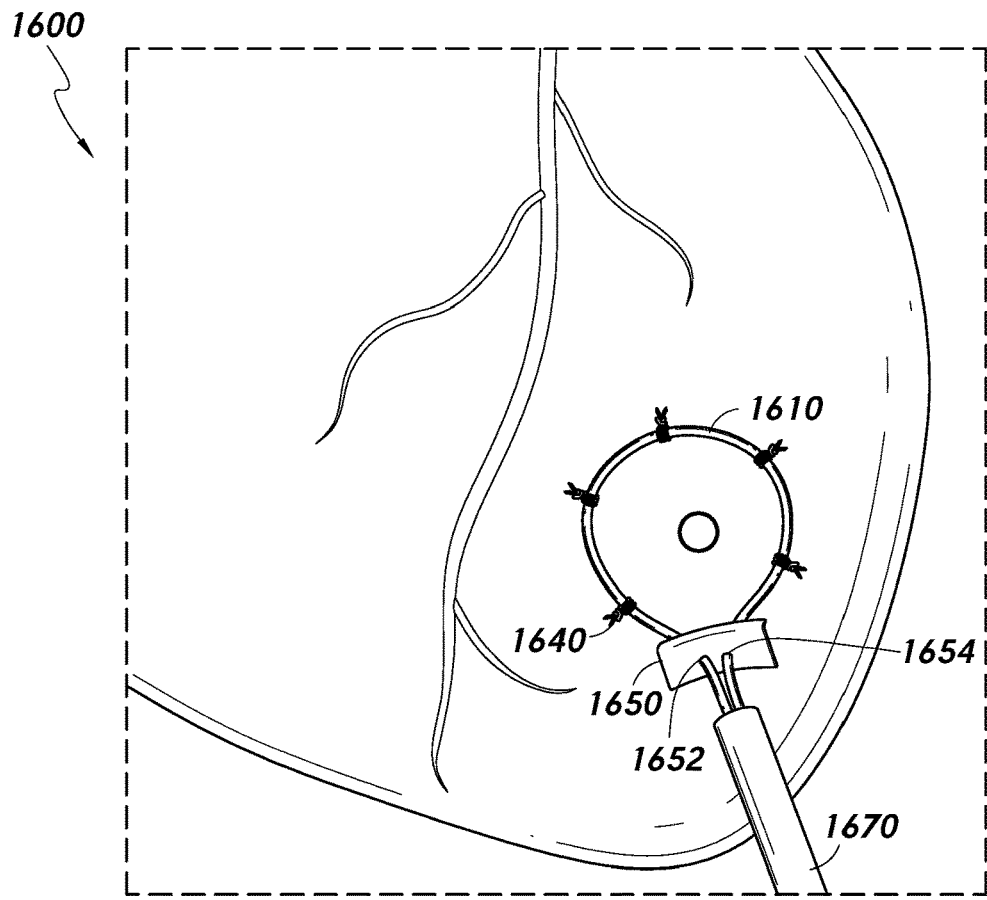
FIG. 16A shows an example of a suture system comprising an elongate tube and a cord extending therethrough, where the suture system can be configured to provide an improved suture pattern for deployment into a target tissue to close an opening in the target tissue.
Figure 16B:
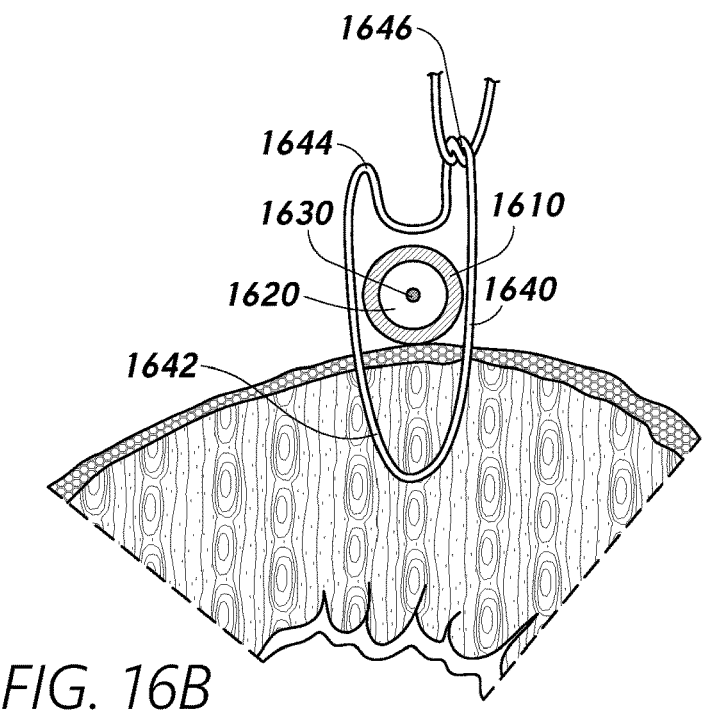
FIG. 16B is a cross-sectional view of the suture system shown in FIG. 16A.

FIGS. 16A and 16B shows a suture system 1600 deployed into a target tissue to form a suture structure configured to close an opening in the target tissue. The suture system 1600 can be configured to provide a suture structure that can demonstrate reduced or no damage to tethers extending through the opening. Referring to FIG. 16A, the suture system 1600 can comprise an elongate tube 1610 configured to be positioned over the target tissue and to at least partially surround the opening in the target tissue, and a plurality of anchors 1640 configured to be partially embedded in the target tissue to couple the elongate tube 1610 to the target tissue. Each of the plurality of anchors 1640 can be configured to be coupled to the suture at predetermined intervals to anchor the elongate tube 1610 to the target tissue. FIG. 16A shows five anchors 1640 coupling the elongate tube 1610 to the target tissue. However, it will be understood that more or fewer anchors 1640 can be used.

The suture system 1600 can comprise a fastener 1650 configured to couple to two portions of the elongate tube 1610. The fastener 1650 can be configured to maintain the two portions of the elongate tube 1610 at predetermined positions relative to one another to facilitate positioning the elongate tube 1610 at least partially surrounds the opening in the target tissue. In some cases, the fastener 1650 comprises a first opening 1652 and a second opening 1654 configured to allow corresponding portions of the elongate tube 1610 to extend therethrough. The first opening 1652 and second opening 1654 of the fastener 1650 can maintain the corresponding portions of the elongate tube 1610 together so as to facilitate maintaining the elongate tube 1610 positioned at least partially around the opening in the target tissue. The elongate tube 1610 can form a loop configuration around the opening. The relative positions of the corresponding portions of the elongate tube 1610 threaded through the fastener 1650 can be selected to provide the desired loop configuration. In some cases, the suture system 1600 can comprise one or more anchors 1640 to couple the fastener 1650 to the target tissue. As described in further detail herein, two anchors 1640 can be used to couple the fastener 1650 to the target tissue.

In some cases, the fastener 1650 can be a surgical pad. The fastener 1650 can comprise a variety of biocompatible materials. In some cases, the fastener 1650 can comprise polytetrafluoroethylene (PTFE), such as PTFE felt. In some cases, the fastener 1650 can be a pledget.

Referring again to FIG. 16A, the suture system 1600 can comprise a cord gathering device 1670. The cord gathering device 1670 can comprise an elongate shape and a lumen extending therethrough. The cord gathering device 1670 can facilitate maintaining the elongate tube 1610 positioned at least partially around the opening in the target tissue. In some cases, the cord gathering device 1670 can comprise a tourniquet, where the tourniquet comprises a lumen extending therethrough. Corresponding portions of the elongate tube 1610 can be inserted within the lumen to facilitate forming the loop configuration around the opening in the target tissue.

FIG. 16B shows a cross-sectional view of a portion of the suture system 1600 deployed into the tissue. The cross-sectional view can be a lateral cross-section taken along a plane that is perpendicular or substantially perpendicular relative to a longitudinal axis of the elongate tube 1610. The elongate tube 1610 can be positioned over the target tissue, including on and in contact with the target tissue. In some cases, the elongate tube 1610 can comprise a lumen 1602 extending therethrough and configured to slidably receive a cord 1630. As described in further detail herein, a mid-portion of the cord 1630 can be received in the lumen 1602, and each of two end portion of the cord 1630 can extend from a respective end of the elongate tube 1610. The cord 1630 can be tensioned to reduce the size of the opening in the target tissue, such as to close the opening. For example, while the cord 1630 is positioned within the elongate tube 1610 that is coupled to the target tissue, an operator can pull on the two end portions of the cord 1630. Pulling on the two end portions of the cord 1630 can tension the cord 1630, which tensions the elongate tube 1610. The tensioned elongate tube 1610 can apply force upon the target tissue to which it is coupled. For example, tensioning the elongate tube 1610 that is positioned in a loop configuration around and coupled to the target tissue adjacent to the opening can result in pulling together the target tissue to reduce the size of the opening. The cord 1630 can comprise any number of biocompatible materials. In some cases, the cord 1630 can comprise a suture, including a polytetrafluoroethylene (PTFE) suture.

An anchor 1640 is shown as being partially embedded within the target tissue to couple the elongate tube 1610 and the cord 1630 extending therein to the target tissue. The anchor 1640 can have a loop configuration, for example comprising a lower portion 1642 configured to extend within the target tissue and an upper portion 1644 configured to extend over a corresponding portion of the elongate tube 1610 to hold the elongate tube 1610 to the target tissue. The upper portion 1644 can be configured to be positioned externally of the target tissue such that the lower portion 1642 and the upper portion 1644 can form a hoop. The hoop can comprise a portion positioned around a circumferential portion of a lateral cross-section of the elongate tube 1610. In some cases, the upper portion 1644 of the anchor 1640 can comprise a knot 1646 such that the anchor 1640 is tied to the elongate tube 1610. In some cases, the anchor 1640 can comprise a suture. In some cases, the suture can comprise a polypropylene suture. For example, the suture system 1600 can comprise a plurality of sutures at discrete positions around the opening in the target tissue. The sutures can be positioned around corresponding circumferential portions of the elongate tube 1610 in the loop configuration on the target tissue. The anchor 1640 can comprise any number of other configurations. In some cases, the anchor 1640 can comprise a staple. For example, the elongate tube 1610 can be stapled to the target tissue.

As described herein, the opening in the target tissue can be formed in an apex region of a heart ventricular wall. A size, such as a length, of the anchor 1640 can be selected such that the anchor 1640 can be deployed to the desired depth into the heart wall. In some cases, each of the plurality of anchors 1640 can be configured to penetrate one or more layers of the heart wall. For example, an anchor 1640 can be configured to extend partially through the myocardium. In some cases, an anchor 1640 can be configured to extend entirely through the myocardium. In some cases, the elongate tube 1610 can be positioned over the epicardium, and each of the plurality of anchors 1640 can extend through the epicardium and partially into the myocardium. In some cases, the elongate tube 1610 can be positioned over the epicardium, and each of the plurality of anchors 1640 can extend through the epicardium, and the myocardium. In some cases, each of the plurality of anchors 1640 can extend through the endothelium. In some cases, the elongate tube 1610 can be positioned over the pericardium, and each of the plurality of anchors 1640 can extend through the pericardium, epicardium, and partially into the myocardium. In some cases, the elongate tube 1610 can be positioned over the pericardium, and each of the plurality of anchors 1640 can extend through the pericardium, epicardium, and myocardium. In some cases, the elongate tube 1610 can be positioned over the pericardium, and each of the plurality of anchors 1640 can extend through the pericardium, epicardium, myocardium and endothelium.

Referring again to FIG. 16B, the orientation in which the anchor 1640 extends into the target tissue can be such that the anchor 1640 avoids crossing paths with any tethers extending through the opening in the target tissue. The anchor 1640 can be deployed into the target tissue such that it is positioned away from the paths of the tethers. For example, the anchor 1640 can extend downward into the target tissue such that the anchor 1640 can avoid interaction with any tethers. An orientation of the anchor 1640 can be along a direction perpendicular or substantially perpendicular to an orientation of an externally oriented surface of the target tissue portion to which it is coupled.

Figure 17:
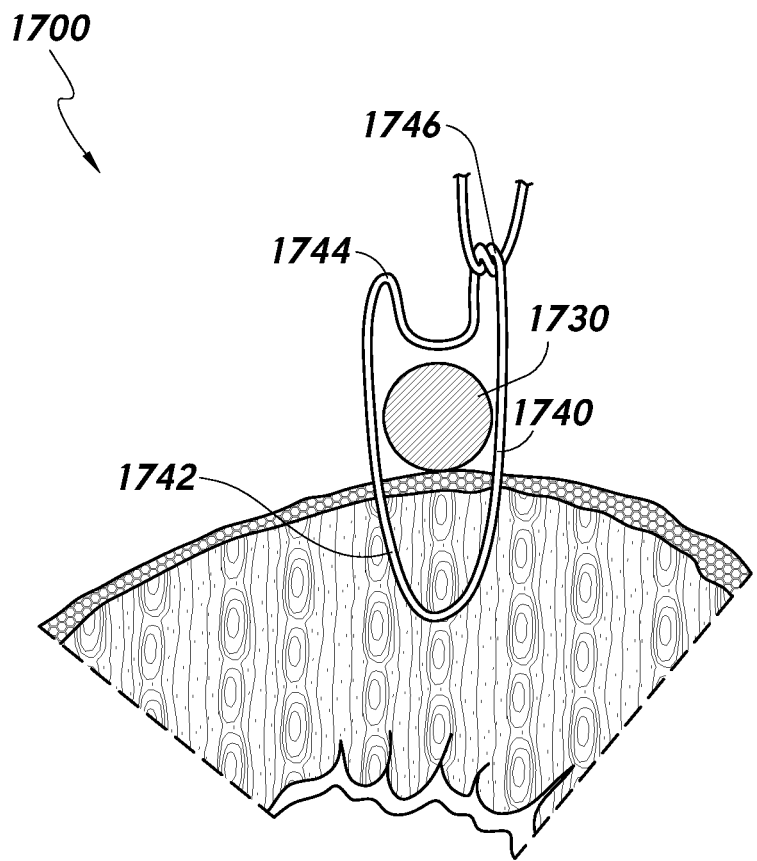
FIG. 17 is a cross-sectional view of an example of a suture system comprising a cord, and not an elongate tube, as deployed into a target tissue.

In some cases, a suture system can comprise either an elongate tube or a cord configured to be positioned over the target tissue and at least partially around the opening in the target tissue, but not both. FIG. 17 is a cross-sectional view of an example of a suture system 1700 comprising a cord 1730 positioned over the target tissue, including on and in contact with the target tissue. The cross-sectional view can be a lateral cross-section taken along a plane that is perpendicular or substantially perpendicular relative to a longitudinal axis of the cord 1730. The cord 1730 can be positioned around the opening in the target tissue. The cord 1730 can be disposed directly on the target tissue without an elongate tube. An anchor 1740 is shown. The anchor 1740 can couple the cord 1730 to the target tissue. The anchor 1740 can be in contact with the cord 1730 to couple the cord 1730 to the target tissue and maintain the cord 1730 in a loop configuration at least partially around the opening in the target tissue. The anchor 1740 can comprise one or more features of the anchor 1640 described with reference to FIG. 16. For example, the anchor 1740 can have a loop configuration comprising a lower portion 1742 configured to extend within the target tissue and an upper portion 1744 configured to extend over a corresponding portion of the cord 1730 to hold the cord 1730 to the target tissue. In some cases, the anchor 1740 can comprise a knot 1746 configured to tie the anchor 1740 to the cord 1730. The suture system 1700 can comprise a plurality of anchors 1740 to couple the cord 1730 to the target tissue so as to position the cord 1730 in a loop configuration around the opening in the target tissue.

The suture system 1700 can comprise one or more other features of the suture system 1600 described with reference to FIG. 16. For example, a fastener can be configured to be coupled to two corresponding portions of the cord 1730 and maintain the two corresponding portions of the cord 1730 at predetermined positions relative to one another such that the 1730 at least partially surrounds the opening in the target tissue. For example, the two corresponding portions of the cord 1730 can each be inserted through a respective opening of the fastener to facilitate maintaining the cord 1730 in a loop configuration around the opening. The suture system 1700 can comprise a cord gathering device to receive at least a portion of the end portions of the cord 1730. Corresponding portions of the cord 1730 can be inserted within a lumen of the cord gathering device to facilitate forming the loop configuration with the cord 1730 around the opening in the target tissue. End portions of the cord 1730 can be tensioned to reduce a size of the opening in the target tissue.

In some cases, a suture system can comprise an elongate tube, rather than a cord, configured to at least partially surround the opening in the target tissue. For example, the suture system can comprise an elongate tube positioned over the target tissue, without a cord extending through the elongate tube. The elongate tube, rather than the cord, can be tensioned to reduce the size of the opening in the target tissue.

The suture systems as described herein (e.g., suture systems 1600, 1700 described with reference to FIGS. 16 and 17) can advantageously provide suture structures comprising the elongate tube and/or cord maintained above the target tissue. Maintaining the elongate tube and/or cord above the target tissue can reduce or avoid interaction with any tethers extending through the opening in the target tissue. For example, maintaining the loop portion of the suture structure above the target tissue can reduce interaction with the tethers, reducing or eliminating abrasion and/or breakage of the tethers. Using a plurality of discrete anchors can simplify the deployment of the anchors, such as compared to forming a traditional purse-string suture. The plurality of anchors can be embedded into the target tissue such that interactions with the tethers can be prevented or reduced. Spacing of the plurality anchors and/or the depth to which the plurality of anchors is deployed into the target tissue can be controlled to provide more uniform suture structures. In some cases, the plurality of anchors can be automatically deployed to reduce time needed for the procedure. For example, the plurality of anchors can comprise a plurality of automatically deployed sutures and/or staples at predetermined intervals around the loop portion.

Figure 18:
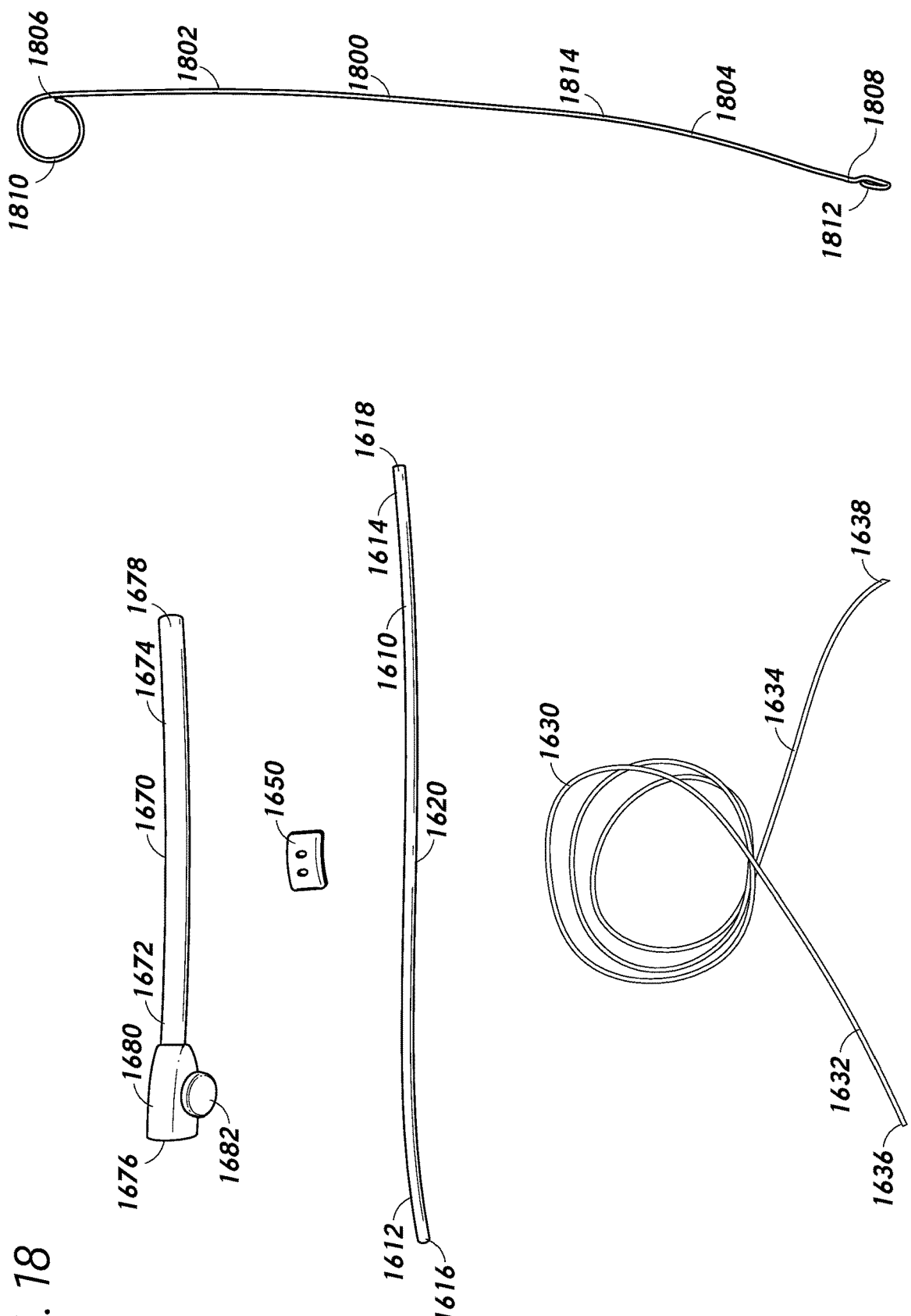
FIG. 18 shows examples of various components of the suture system described with reference to FIG. 16.

FIG. 18 shows various components of the suture system 1600 described with reference to FIG. 16. For example, the suture system 1600 can comprise the elongate tube 1610, the cord 1630, the fastener 1650, the cord gathering device 1670, and a cord snare 1800. The cord gathering device 1670 is shown in more detail. In some cases, the cord gathering device 1670 can comprise an elongate shape and a lumen extending therethrough. While the suture system 1600 is in an assembled configuration, a distal portion 1674 of the cord gathering device 1670 can be configured to be oriented toward, and a proximal portion 1672 can be configured to be oriented away from, the loop configuration formed by the elongate tube 1610 and the cord 1630. A portion of the cord 1630 can be positioned within the elongate tube 1610, with a first portion 1632 extending from a first end 1616 of the elongate tube 1610 and a second portion 1634 extending from a second end 1618 of the elongate tube 1610. A first end 1636 of the cord 1630 and a second end 1638 of the cord 1630 can be configured to be disposed proximally of the first end 1616 of the elongate tube 1610 and the second end 1618 of the elongate tube 1610, respectively. As described in further detail herein, portions of the cord 1630 and elongate tube 1610 not forming the loop portion to surround the opening in the target tissue can be inserted into an opening of the lumen of the cord gathering device 1670 at a distal end 1678 of the cord gathering device 1670. The cord 1630 can extend through the cord gathering device 1670 and extend from the distal end 1678 to a proximal end 1676 of the cord gathering device 1670. The cord 1630 can extend out from the proximal end 1676. The cord gathering device 1670 can comprise a cord engagement component 1680 associated with the proximal portion 1672. The cord engagement component 1680 can comprise a cord engagement feature 1682 configured to engage with portions of the cord 1630 extending from the proximal end 1676 of the cord gathering device 1670, so as to fix the position of the cord 1630 relative to the cord gathering device 1670. Fixing the relative position of the cord 1630 can maintain tension applied to the cord 1630 to reduce the size of the opening in the target tissue. In some cases, the cord engagement feature 1682 can comprise a protrusion (e.g., a knob) around which corresponding portions of the cord 1630 can be wound to fix the position of the cord 1630.

In some cases, the cord gathering device 1670 can comprise a tourniquet. For example, the tourniquet can comprise a lumen extending therethrough. The lumen can be configured to receive corresponding portions of the cord and elongate tube. A cord engagement component can be associated with a proximal portion of the tourniquet such that a portion of the cord can be fixated on the cord engagement component to fix the position of the cord relative to the tourniquet.

Referring again to FIG. 18, the cord snare 1800 can be used to thread the cord 1630 through the lumen of the cord gathering device 1670 and/or the elongate tube 1610. A handle 1810 can be associated with a proximal portion 1802 of the cord snare 1800. A snare portion 1812 can be associated with a distal portion 1804 of the cord snare 1800. For example, the handle 1810 can be at a proximal end 1806 of an elongate rod portion 1814 and the snare portion 1812 can be at a distal end 1808 of the elongate rod portion 1814. The snare portion 1812 can comprise any number of configurations for capturing the cord 1630 while threading the cord 1630 through the cord gathering device 1670 and/or the elongate tube 1610. For example, the snare portion 1812 can comprise a hook configuration.

Figure 19C:
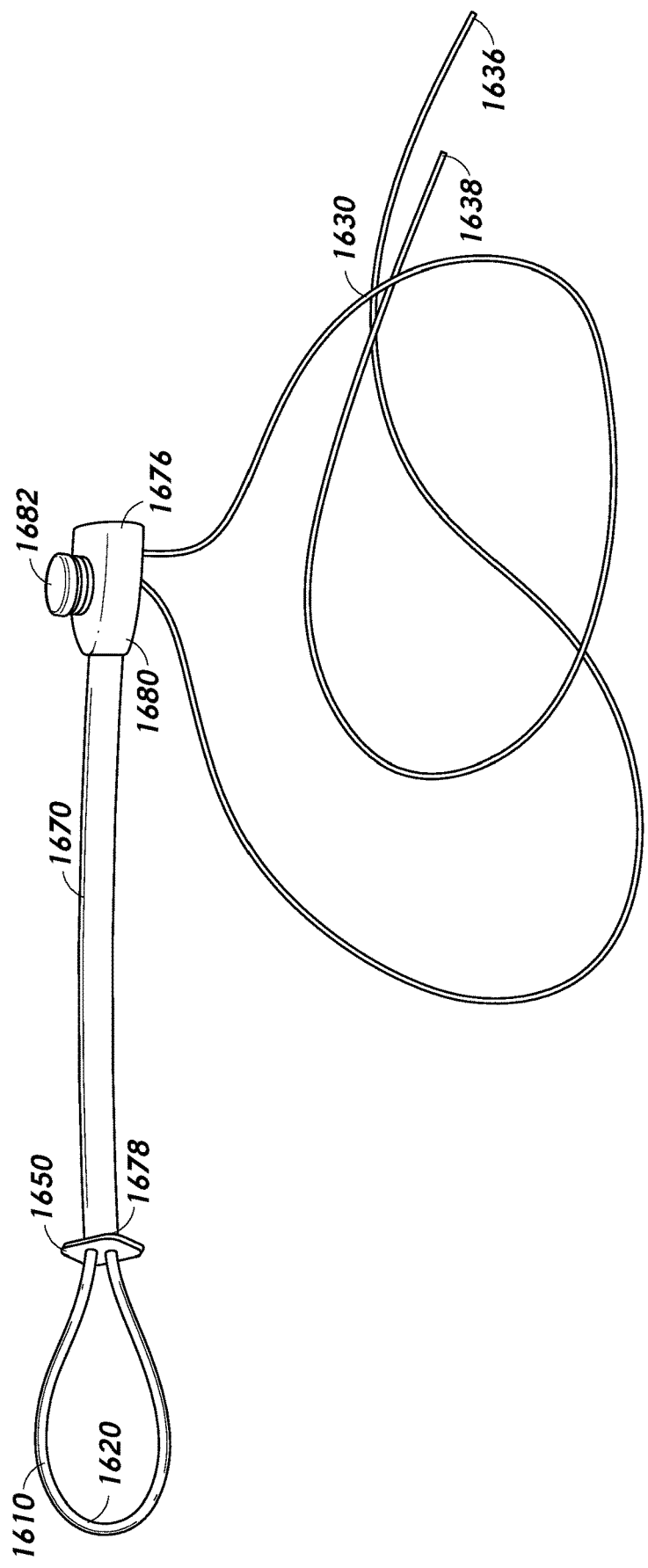

FIGS. 19A through 19C show various stages in the assembling of some components of the suture system 1600. FIG. 19A shows a portion of the cord 1630 extending through the lumen of the elongate tube 1610. As described herein, a portion of the cord 1630 can be received within the lumen of the elongate tube 1610 such that a first portion 1632 of the cord 1630 can extend through the first end 1616 of the elongate tube 1610 and a second portion 1634 of the cord 1630 can extend through the second end 1618 of the elongate tube 1610.

FIG. 19B shows the fastener 1650 coupled to the elongate tube 1610. For example, with the portion of the cord 1630 received within the lumen of the elongate tube 1610, a first end portion 1612 and a second end portion 1614 of the elongate tube 1610 can be advanced through the first and second openings 1652, 1654 on the fastener 1650, respectively. Advancing the first and second end portions 1612, 1614 through the openings 1652, 1654 in the fastener 1650 can facilitate maintaining the elongate tube 1610, with the cord 1630 extending therethrough, in a desired configuration, such as a loop configuration. For example, a midportion 1620 of the elongate tube 1610 extending between the first and second end portions 1612, 1614, can form the loop portion to at least partially surround the target opening. The portion of the elongate tube 1610 disposed within the openings 1652, 1654 can be adjusted based on a desired size of the loop portion.

Referring to FIG. 19C, at least some portions of the elongate tube 1610 and cord 1630 not forming the loop can be inserted into the cord gathering device 1670. For example, the first end portion 1612 and second end portion 1614 of the elongate tube 1610, and the first portion 1632 and second portion 1634 of the cord 1630, not forming the loop can be advanced through at least a portion of the lumen of the cord gathering device 1670. For example, portions of the elongate tube 1610 and cord 1630 configured to be proximal of the fastener 1650 can be inserted into the lumen of the cord gathering device 1670 at the distal end 1678 of the cord gathering device 1670. The first and second ends 1616, 1618 of the elongate tube 1610 can be configured to be positioned within the lumen of the cord gathering device 1670. The first and second ends 1636, 1638 of the cord 1630 can extend proximally from the first and second ends 1616, 1618 of the elongate tube 1610 disposed within the lumen of the cord gathering device 1670. The cord 1630 can have portions which extend through the entire length of the lumen of the cord gathering device 1670 such that the first and second ends 1636, 1638 of the cord 1630 are configured to be disposed proximally of the proximal end 1676 of the cord gathering device 1670. The cord 1630 can extend through the cord gathering device 1670 and extend from the distal end 1678 to a proximal end 1676 of the cord gathering device 1670. The cord 1630 can extend out from the proximal end 1676 and engage with the cord engagement feature 1682. For example, portions of the cord 1630 extending from the proximal end 1676 of the cord gathering device 1670 can be wound around the cord engagement feature 1682. An operator, such as a surgeon, can manipulate portions of the cord 1630, including the first and second ends 1636, 1638 of the cord 1630, extending proximally of the proximal end 1676 of the cord gathering device 1670 to tension the cord 1630. The operator can pull on portions of the cord 1630 proximal of the cord gathering device 1670 to achieve the desired tension. After the desired tension is achieved, the cord 1630 can be secured to the cord engagement feature 1682 to maintain the desired tension. Fixating the position of the cord 1630 using the cord engagement feature 1682 can be used to temporarily maintain desired tension on the cord 1630, such as during a surgical procedure. In some cases, after the cord 1630 has been tensioned to provide the desired force to close the opening in the target tissue around a surgical instrument (e.g., an introducer) positioned within the opening, a portion of the cord 1630 can be wound around the cord engagement feature 1682 to maintain the tension. Maintaining the tension in the cord 1630 can keep the opening sealed around the surgical instrument such that hemostasis can be maintained.

In some cases, the suture system 1600 can be provided in various pre-assembled forms. In some cases, the cord 1630 can be pre-threaded through the elongate tube 1610. In some cases, the elongate tube 1610, comprising the cord 1630 extending therethrough, can be pre-coupled to the fastener 1650 such that the loop portion is pre-formed. The position of the fastener 1650 relative to the elongate tube 1610 can be adjusted to adjust the size of the loop portion. In some cases, corresponding portions of the elongate tube 1610 and cord 1630 can be pre-inserted into the cord gathering device 1670. Providing a suture system comprising one or more pre-assembled components can simplify surgical procedures and decrease procedure durations to save resources and reduce impact to patients.

Figure 21:
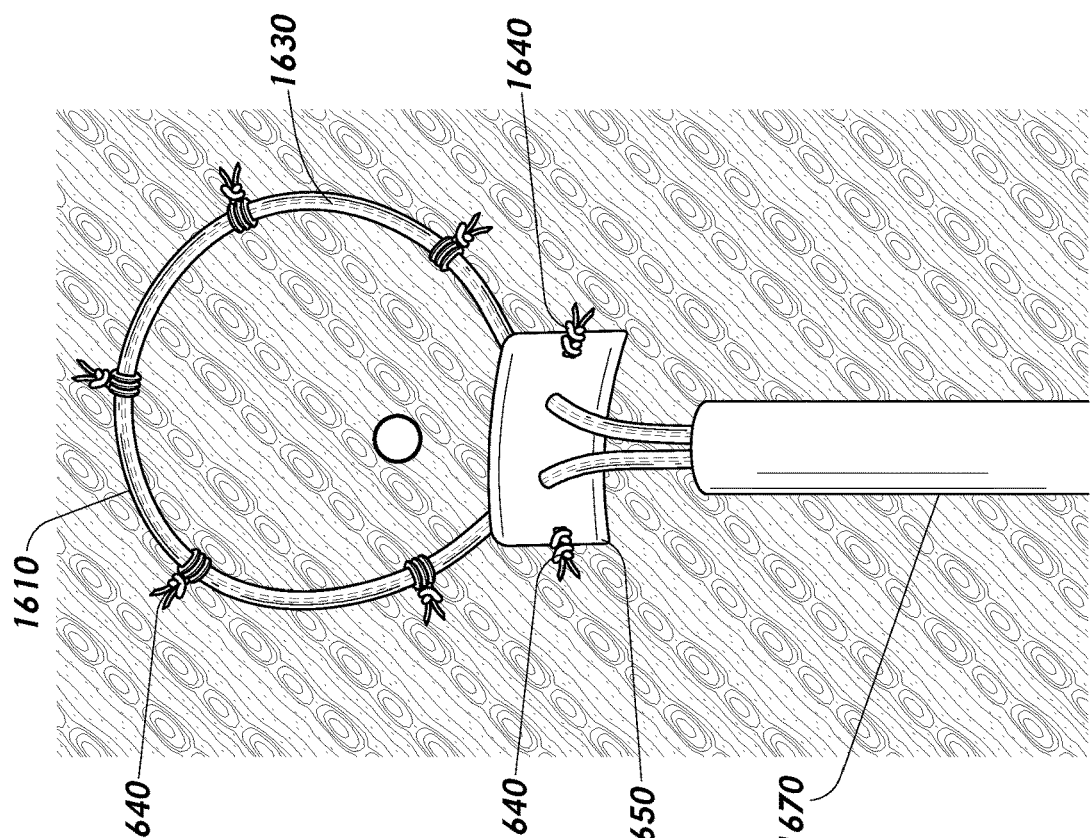
FIG. 21 shows another example of an elongate tube and cord positioned over a target tissue in an un-tensioned state to at least partially surround an opening in the target tissue.
Figure 20:
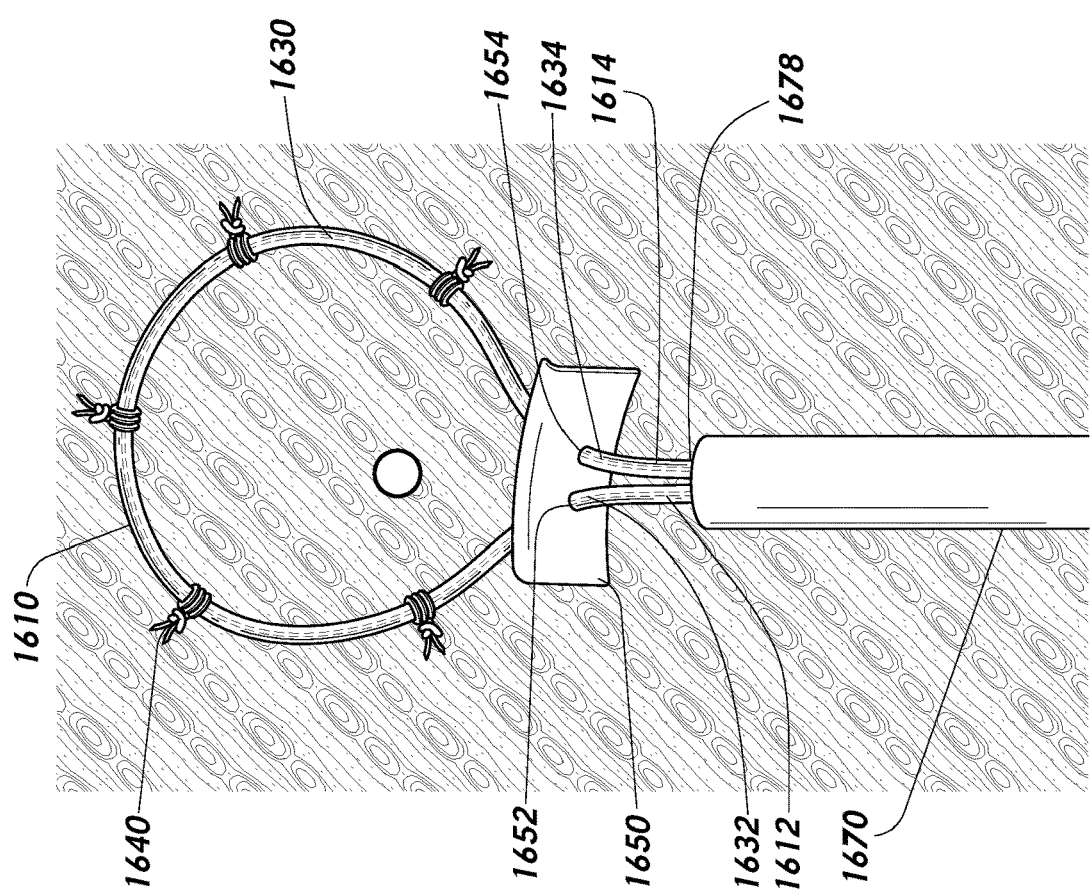
FIG. 20 shows an example of an elongate tube and cord positioned over a target tissue in an un-tensioned state to at least partially surround an opening in the target tissue.

FIGS. 20 and 21 show the elongate tube 1610, comprising the cord 1630 extending therethrough, positioned to at least partially surround the opening in the target tissue, and the plurality of anchors 1640 coupling the elongate tube 1610 and cord 1630 to the target tissue. Corresponding portions of the elongate tube 1610 and cord 1630 can be coupled to the fastener 1650, extending through respective openings 1652, 1654 of the fastener 1650. At least a portion of the first portion 1612 and second portion 1614 of the elongate tube 1610, not forming the loop, and at least a portion of the first portion 1632 and second portion 1634 of the cord 1630, not forming the loop, can be inserted into the lumen of the cord gathering device 1670 through the distal end 1678 of the cord gathering device 1670. FIG. 20 shows a plurality of anchors 1640 (e.g., five) spaced from one another around the loop portion of the elongate tube 1610. FIG. 21 shows a plurality of anchors 1640 (e.g., five) spaced from one another around the loop portion of the elongate tube 1610, as well as a plurality of anchors 1640 to couple the fastener 1650 to the target tissue. For example, two anchors 1640 can be used to couple the fastener 1650 to the target tissue. In some cases, the two anchors 1640 can be positioned at opposing locations on the fastener 1650. It will be understood that the number of anchors 1640 coupling the elongate tube 1610, cord 1630 and/or fastener 1650 to the target tissue can be different from that shown in FIGS. 20 and 21.

FIGS. 20 and 21 show the elongate tube 1610 and cord 1630 in an un-tensioned state. In some cases, the loop portion formed by elongate tube 1610 and the cord 1630 in the un-tensioned state can comprise a circular or substantially circular shape. In some cases, the loop portion formed by elongate tube 1610 and the cord 1630 in the un-tensioned state can comprise an oval shape. In some cases, the loop portion formed by elongate tube 1610 and the cord 1630 in the un-tensioned state can comprise a non-rounded shape, such as a star shape, pentagon shape, a hexagon shape, and/or a rectangular circular, including a square shape.

Figure 22:
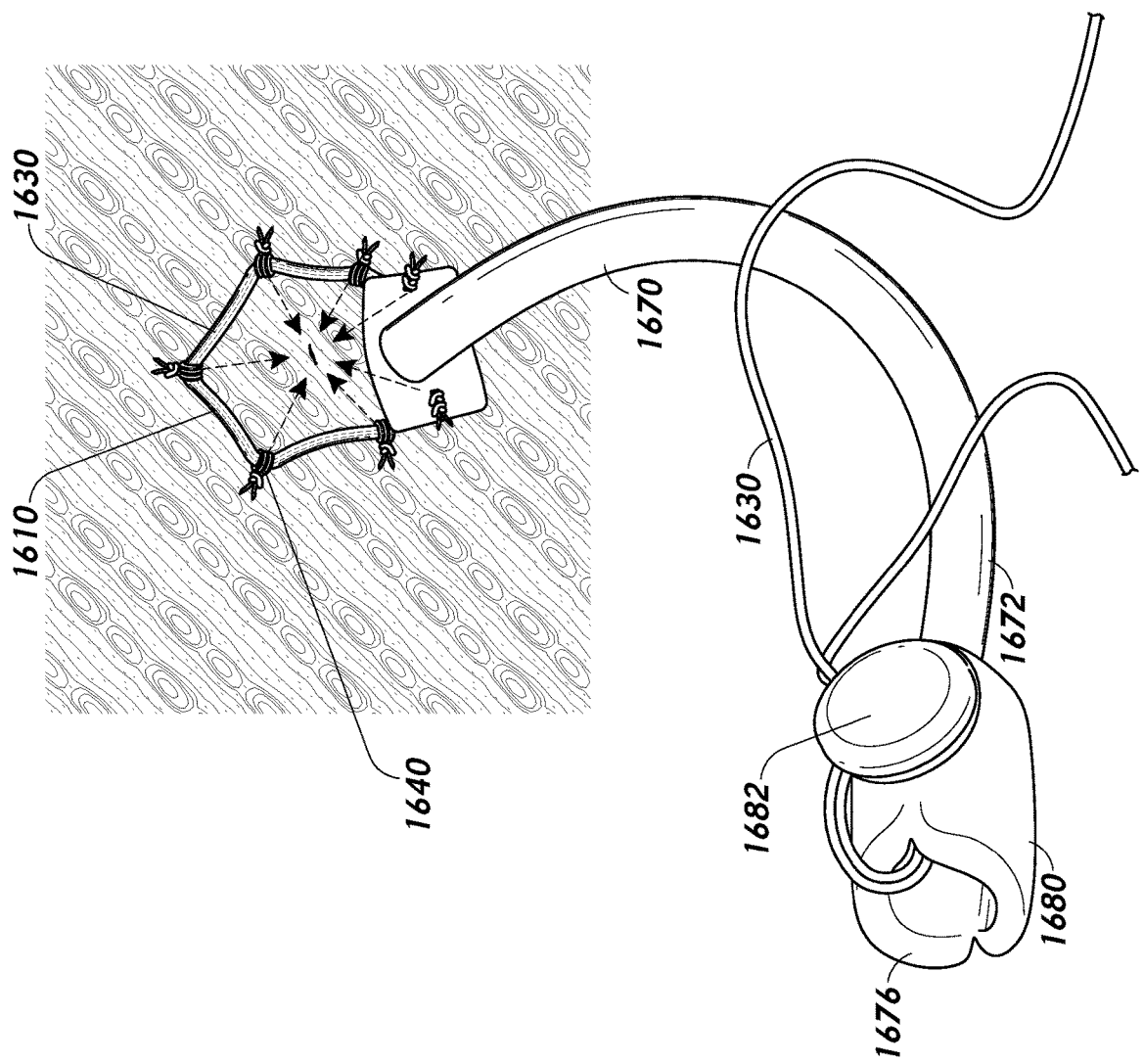
FIG. 22 shows the elongate tube and cord of FIG. 21 in a tensioned state such that the opening in the target tissue is closed.

FIG. 22 shows the elongate tube 1610 and cord 1630 in FIG. 21 in a tensioned state. The cord 1630 extending from the proximal end 1676 of the cord gathering device 1670 can be tensioned and wound around the cord engagement feature 1682 on the cord engagement component 1680 associated with the proximal portion 1672 of the cord gathering device 1670. Tensioning the cord 1630 extending within the elongate tube 1610 while the anchors 1640 are coupled to the tissue and the elongate tube 1610 can thereby exert force upon the tissue to pull the tissue toward the opening and reduce the size of the opening. For example, arrows in FIG. 22 show the directions of the forces exerted upon the tissue when the cord 1630 is tensioned. The arrows show that forces can be exerted upon the tissue to move the tissue together toward the opening to thereby reduce the size of the opening, including to close the opening. For example, concentric forces exerted upon the tissue, due to pulling together of the anchors 1640 when the cord 1630 is tensioned, can push the tissue together at the opening. As shown in FIG. 22, in some cases, the loop portion formed by the elongate tube 1610, and cord 1630 extending therethrough, can comprise a pentagon shape when in a tensioned state.

Figure 23:
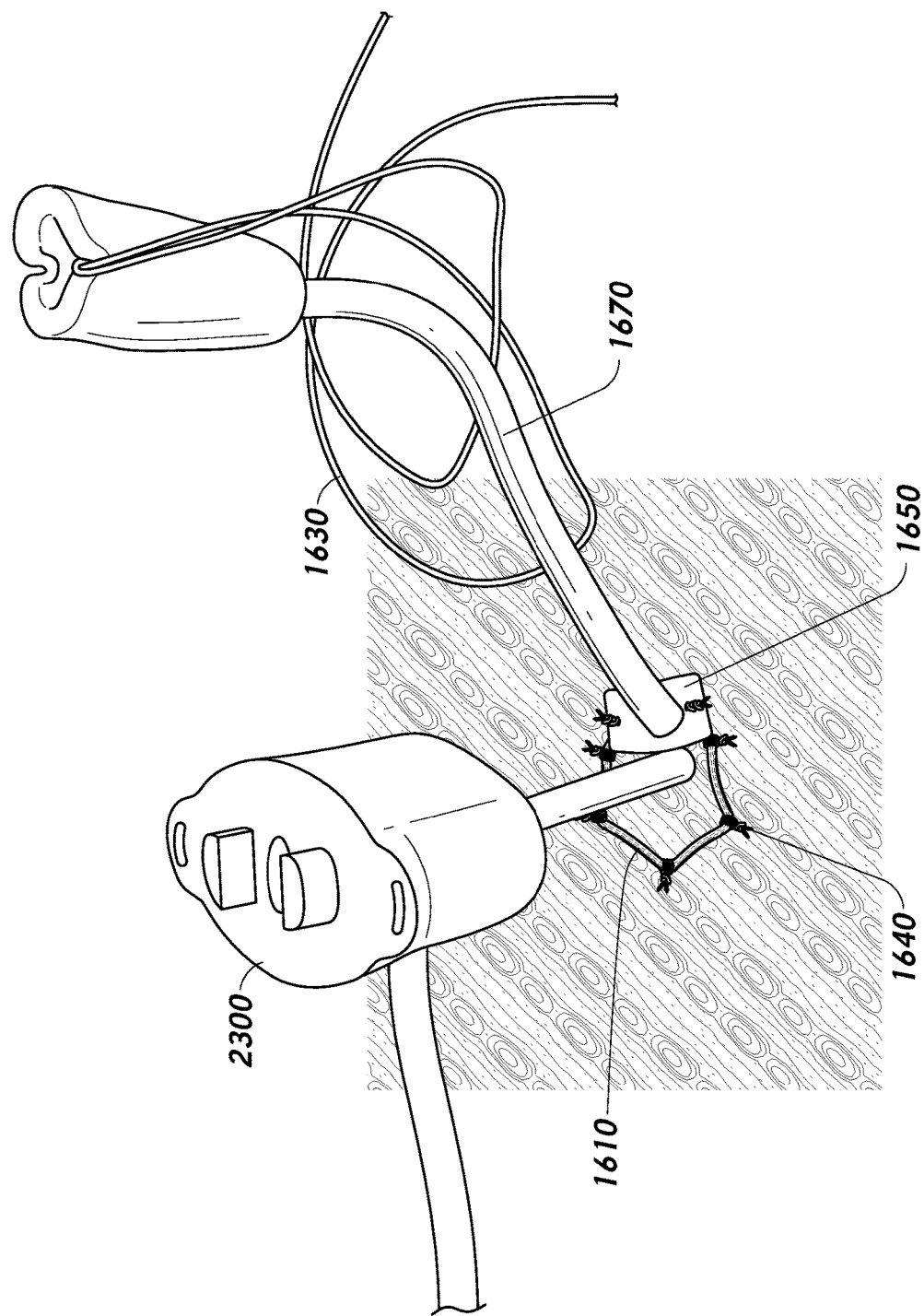
FIG. 23 shows the elongate tube and cord of FIG. 21 in a tensioned state such that the opening in the target tissue is closed around a surgical instrumentation inserted within the opening.

FIG. 23 shows a surgical instrumentation 2300 inserted within the opening in the target tissue. The surgical instrumentation 2300 can comprise an introducer through which one or more medical devices and/or therapies can be delivered. In some cases, as described herein, the opening can be formed on the ventricular heart wall. One or more tethers can be delivered through an introducer positioned through the opening to one or more heart valve leaflets. The elongate tube 1610 and cord 1630 can be maintained in a tensioned state such that the opening is closed around the surgical instrumentation 2300. The opening can be closed around the surgical instrumentation 2300 during the procedure such that hemostasis can be maintained. Portions of the cord 1630 extending from the proximal end 1676 of the cord gathering device 1670 can be tensioned and wound around the cord engagement feature 1682 (not shown) on the cord engagement component 1680 to maintain the tension in the cord 1630 temporarily during surgical procedures.

Figure 24:
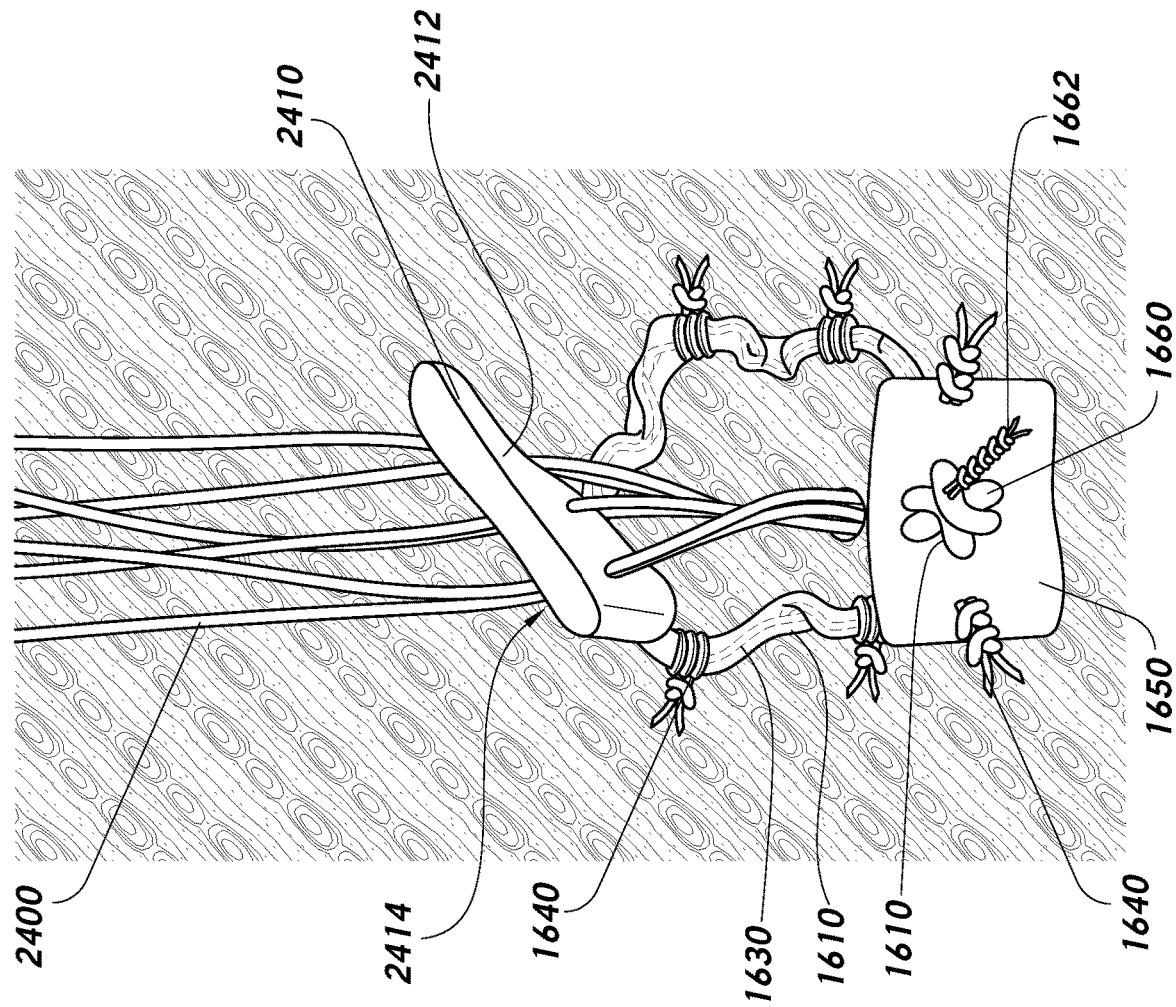
FIG. 24 shows the elongate tube and cord of FIG. 21 in a tensioned state and the opening in the target tissue closed around a plurality of tethers extending through the opening.

FIG. 24 shows a plurality of tethers 2400 extending through the opening in the target tissue. A process for tethering a heart valve leaflet to a heart wall can comprise delivering a first distal portion of each of the plurality of tethers 2400 to the heart valve leaflet, such as a mitral valve leaflet. The first distal portions can each be anchored to the heart valve leaflet. A second distal portion of the plurality of tethers 2400 can be anchored to the heart wall so as to tether the heart valve leaflet to the heart wall. The plurality of tethers 2400 can be coupled to a pad 2410. The process for tethering the heart valve leaflet can comprise securing the second distal portions of each of the plurality of tethers 2400 to the pad 2410. The elongate tube 1610 and cord 1630 can be maintained in a tensioned state such that the opening is closed around the plurality of tethers 2400. For example, after implantation of the tethers 2400 is complete, any surgical instrumentation can be withdrawn from the opening in the target tissue. The cord 1630 can be further tensioned to further reduce the size of the opening so as to close the opening around the plurality of tethers 2400 extending therethrough. The pad 2410 can be positioned at least partially over the closed opening in the target tissue, comprising a first surface 2412 oriented toward the tissue and a second surface 2414 oriented away from the tissue. The plurality of tethers 2400 can each comprise a portion extending from the opening in the target tissue. Respective portions of the plurality of tethers 2400 can be threaded through the pad 2410 from the first surface 2412 through to the second surface 2414 and secured to the pad 2410. For example, knots can be formed over the second surface 2414 using the tethers 2400.

The tensioned state of the elongate tube 1610 and the cord 1630 can be made more permanent such that the opening can be closed, such as after completion of the surgical procedure. In some cases, loose ends of the elongate tube 1610 and cord 1630 can be tied off. For example, one or more knots 1660 can be formed with loose ends of the elongate tube 1610. One or more knots 1662 can be formed using the loose ends of the cord 1630. The elongate tube 1610 and the cord 1630 can be tied before or after the tethers 2400 are secured to the pad 2410.

Figure 25:
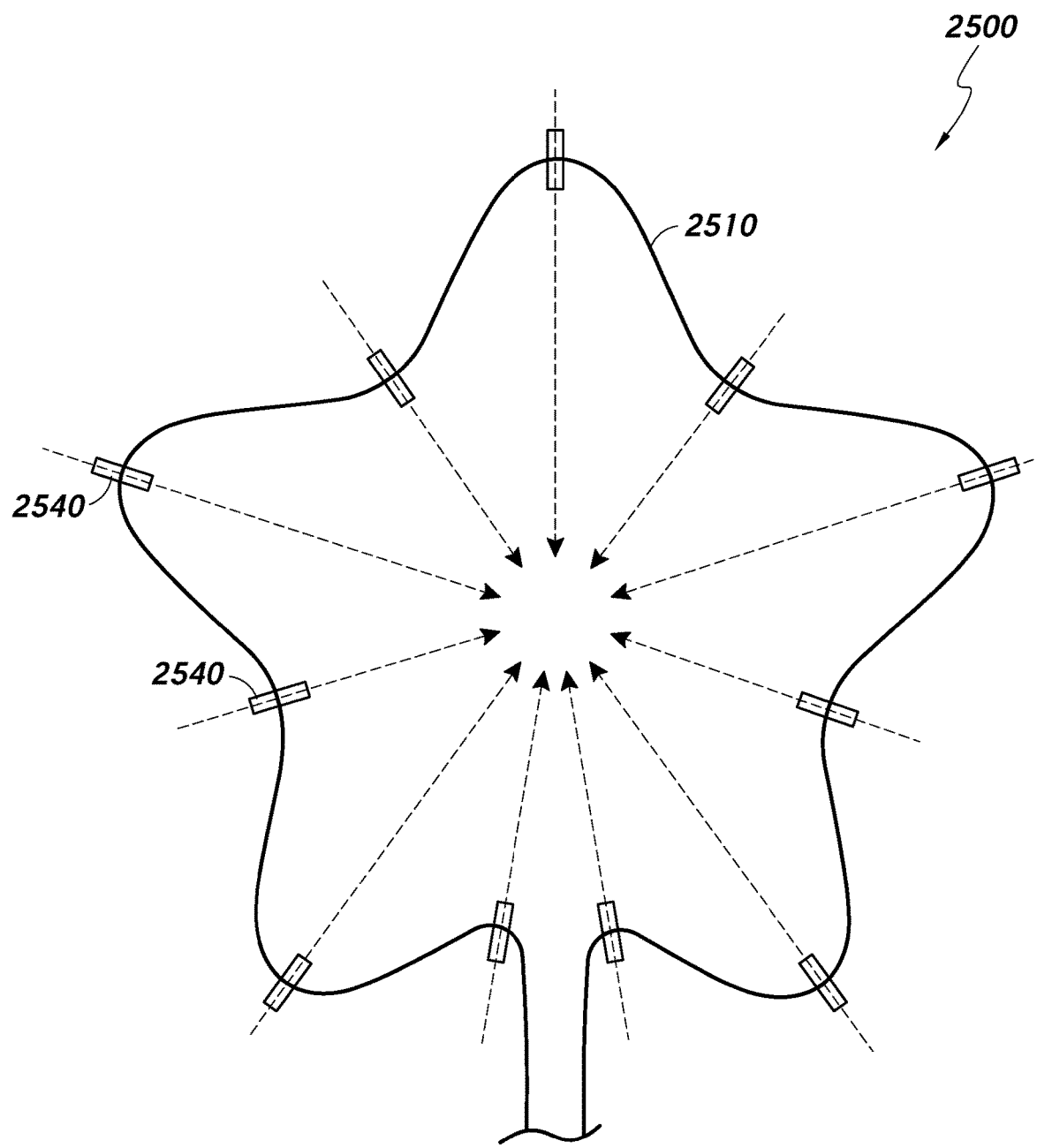
FIG. 25 is a schematic diagram showing an example of a suture pattern comprising a star-shaped loop portion.

As described herein, the loop portion formed by the elongate tube 1610 and cord 1630 can comprise a number of different shapes. FIG. 25 shows a schematic diagram of an example of suture structure 2500 comprising a loop portion 2510 that forms a star shape. FIG. 25 shows a suture structure comprising eleven anchors 2540 to form a star-shaped suture pattern around the opening in the target tissue. The plurality of anchors 2540 can be positioned at varying distances from the opening, for example, at the corner portions of the star, to form the star shape. In some cases, more or fewer anchors 2540 can be used. For example, the suture structure 2500 can be formed by the elongate tube 1610, and/or the cord 1630, and the anchors 1640. The elongate tube 1610 comprising the cord 1630 extending therethrough can be used to form a loop portion comprising a star shape. The elongate tube 1610 and cord 1630 can be coupled to the tissue using a plurality of the anchors 1640. The arrows show the force exerted upon the target tissue when the cord 1630 is tensioned. Tensioning of the elongate tube 1610 and cord 1630 can pull on the anchors 1640 coupled to the tissue to thereby cause tissue adjacent to the opening to be pushed inward toward the opening to reduce the size of the opening, including to close the opening.

Figure 26:
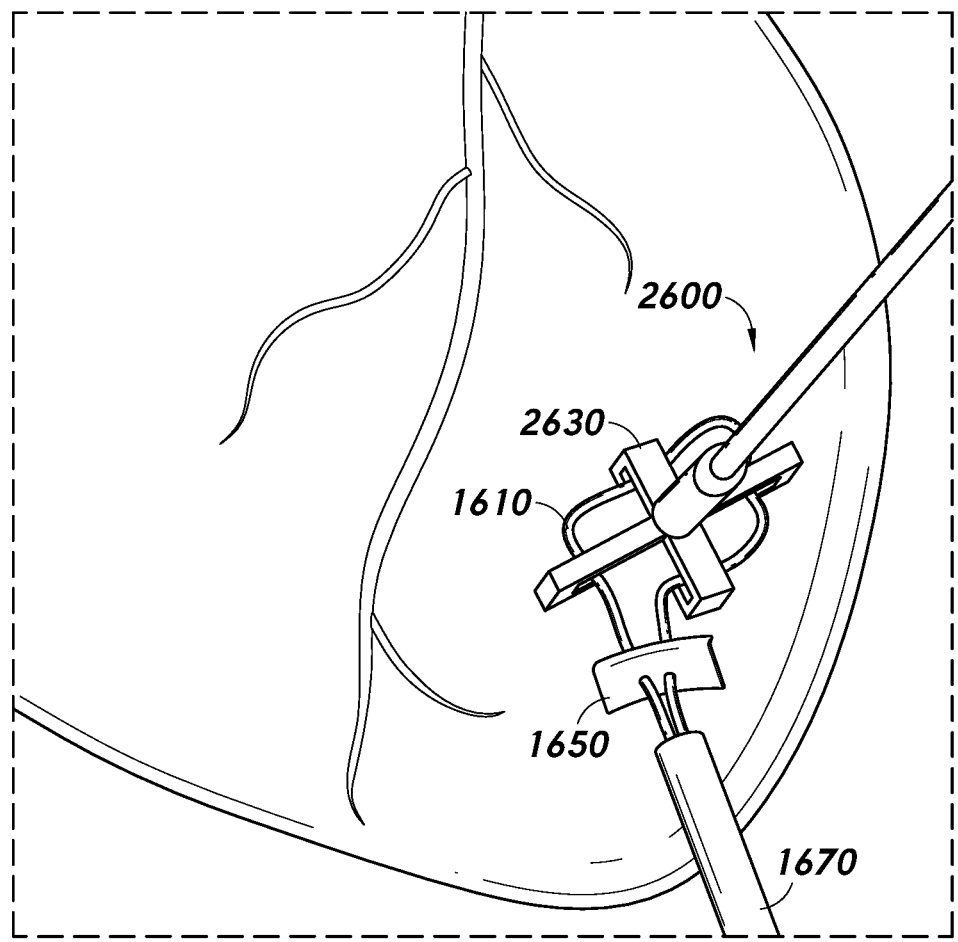
FIG. 26 shows use of an example of an elongate tube applicator to maintain an elongate tube in a desired configuration over a target tissue.

In some cases, an applicator can be used to facilitate positioning an elongate tube over the target tissue. FIG. 26 shows an example of an elongate tube applicator 2600 positioned against the target tissue to maintain the elongate tube 1610 in a desired loop configuration and at a desired position over the target tissue. As described in further detail herein, an elongate tube engagement component 2630 can be associated with a distal portion of the elongate tube applicator 2600. The elongate tube engagement component 2630 can be configured to engage the elongate tube 1610 so as to maintain the elongate tube in a predetermined shape over the target tissue while the elongate tube is anchored to the target tissue.

Figure 27B:
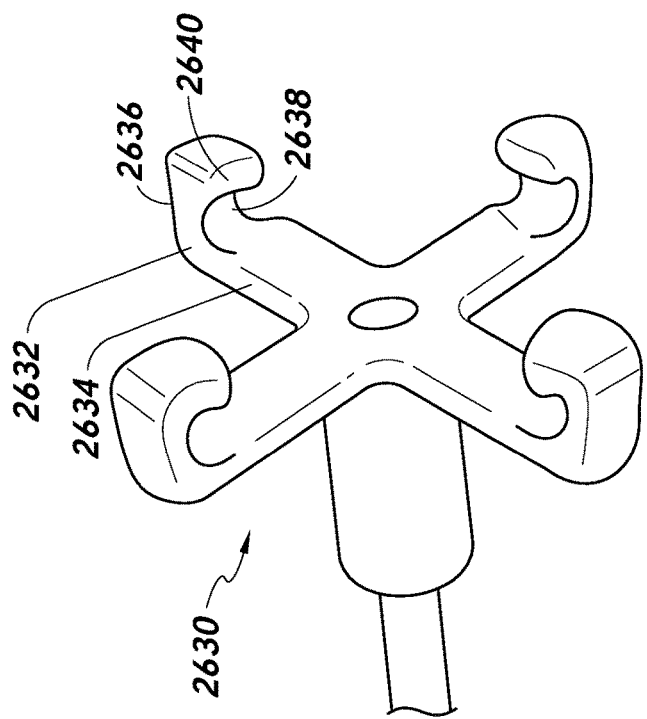
FIG. 27B is a more detailed perspective view of a distal portion of the elongate tube applicator.
Figure 27A:
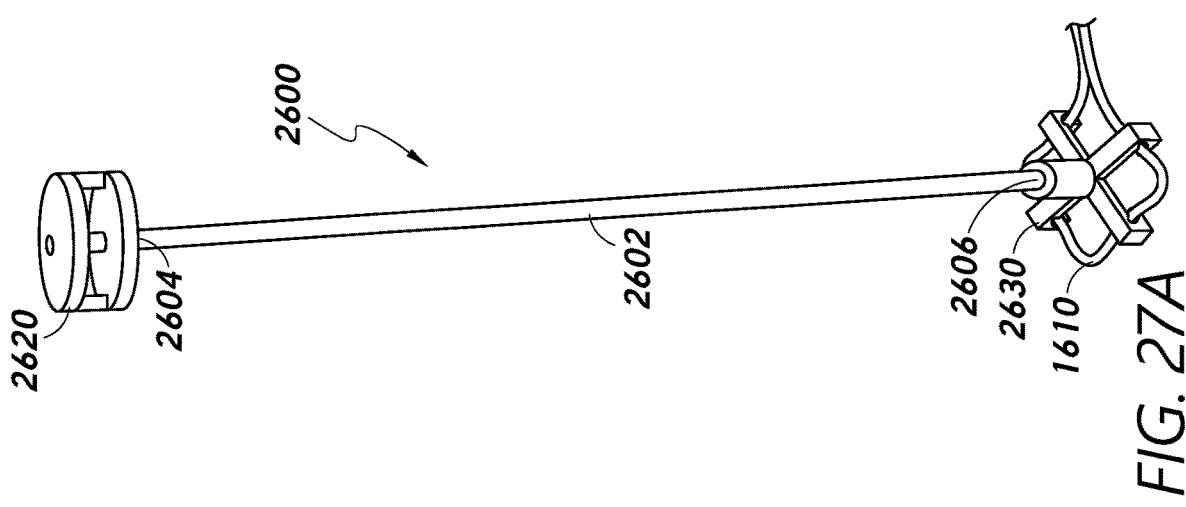
FIG. 27A is a perspective view of an example of an elongate tube applicator.

FIGS. 27A and 27B show the elongate tube applicator 2600 in further detail. Referring to FIG. 27A, the elongate tube applicator 2600 can comprise a proximal handle 2620, and a shaft 2602 extending distally from the proximal handle 2620. A proximal end 2604 of the shaft 2602 can be coupled to the proximal handle 2620 and a distal end 2606 of the shaft 2602 can be coupled to the elongate tube engagement component 2630. The shaft 2602 can comprise a linear or substantially linear rod, such as a cylindrical rod. An operator, such as a surgeon, can use the proximal handle 2620 to position the elongate tube engagement component 2630.

FIG. 27B shows the elongate tube engagement component 2630 in more detail. The elongate tube engagement component 2630 can comprise a plurality of extensions 2632. The plurality of extensions 2632 can each comprise a laterally extending portion 2634 extending laterally, including perpendicularly or substantially perpendicularly, relative to a longitudinal axis of the elongate tube applicator 2600. The longitudinal axis of the elongate tube applicator 2600 can be coaxial with a longitudinal axis of the shaft 2602, extending along a dimension extending between the proximal end 2604 and distal end 2606 of the shaft 2602. For example, a laterally extending portion 2634 can extend laterally, including perpendicularly or substantially perpendicularly, relative to a longitudinal axis of the shaft 2602. The plurality of extensions 2632 can each comprise a plurality of distally extending portions 2636 extending distally from the laterally extending portion 2634. In some cases, each of the extensions 2634 can have an "L" shape. In some cases, the laterally extending portion 2634 can be perpendicular or substantially perpendicular to the shaft 2602. In some cases, the laterally extending portion 2634 and the distally extending portion 2636 can be perpendicular or substantially perpendicular to one another. The distally extending portion 2636 can be parallel or substantially parallel to a longitudinal axis of the shaft 2602. For example, a laterally extending portion 2634 can be a proximal perpendicularly or substantially perpendicularly portion extending from the shaft 2602, including from the distal end 2606 of the shaft 2602. A distally extending portion 2636 can be a distal portion extending distally and perpendicularly or substantially perpendicularly from the proximal perpendicular portion.

In some cases, a laterally extending portion may not be perpendicular to the longitudinal axis of the elongate tube applicator. For example, a laterally extending portion can extend distally at an angle other than a right angle from the distal end of the shaft. In some cases, each of the plurality of extensions can comprise a laterally extending portion extending distally at an angle from the distal end of the shaft and a distally extending portion which is parallel or substantially parallel to the shaft. In some cases, the shaft can be non-linear, for example comprising a curvature to facilitate access to the target site.

Each of the distally extending portions 2636 can comprise thereon a recess 2638 configured to receive a corresponding portion of the elongate tube. Each distally extending portion 2636 can comprise a recess 2638 on a surface 2640 oriented toward the longitudinal axis of the shaft 2602. Corresponding portions of the elongate tube can be positioned within each recess 2638 such that the elongate tube can be maintained over the target tissue in the desired loop configuration while anchors are deployed into the target tissue to couple the elongate tube to the target tissue. For example, each distally extending portion 2636 can comprise a recess 2638 on an inwardly facing surface, such that the elongate tube can be maintained between the inwardly facing surfaces 2640 of the plurality of distally extending portions 2636. In some cases, the elongate tube engagement component 2630 can comprise a claw configuration, the elongate tube being maintained between inwardly oriented surfaces of the claw configuration while being coupled to the tissue.

In some cases, a longitudinal dimension, such as a length, of the laterally extending portion 2634 can be selected based at least in part on a lateral dimension, such as a diameter, of the loop portion formed by the elongate tube 1610. The elongate tube applicator 2600 shown in FIGS. 27A and 27B includes an elongate tube engagement component 2630 with four extensions 2632. For example, the elongate tube engagement component 2630 can be configured to receive four corresponding portions of the elongate tube 1610. An elongate tube engagement component 2630 can comprise more or fewer extensions. In some cases, the number of extensions can be based on a desired shape of the loop formed by the elongate tube. For example, the elongate tube applicator 2600 of FIG. 27 can be used to form loop comprising a square shape. In some cases, the elongate tube engagement component 2630 can comprise five extensions configured to maintain the elongate tube in a pentagon or substantially pentagon shape, or six extensions configured to maintain the elongate tube in a hexagon or substantially hexagon shape. In some cases, the elongate tube engagement component 2630 can be configured to maintain the elongate tube in a circular or substantially circular shape.

The elongate tube engagement component 2630 shown in FIG. 27 can comprise a plurality of laterally extending portions 2634 comprising the same length. In some cases, the longitudinal dimension of the laterally extending portions may not be uniform. For example, an elongate tube engagement component can comprise one or more laterally extending portions which have a different length from that of one or more other laterally extending portions. In some cases, an elongate tube engagement component comprising laterally extending portions having different lengths can be configured to maintain the elongate tube in a star shape. For example, the elongate tube engagement component can comprise alternating longer and shorter laterally extending portions.

Figure 28:
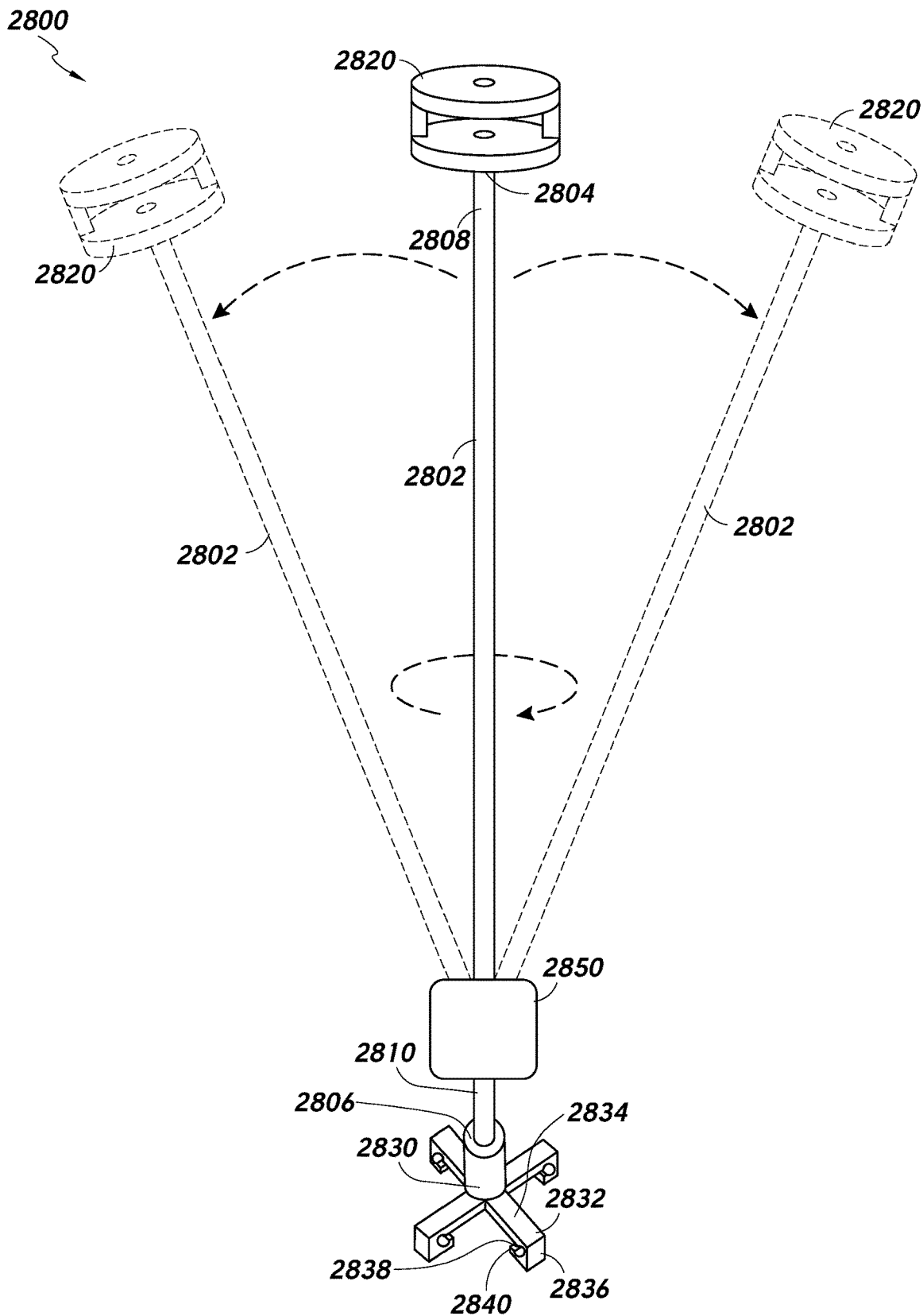
FIG. 28 is a perspective view of an example of an elongate tube applicator comprising a swivel joint.

FIG. 28 shows an example of an elongate tube applicator 2800 comprising a swivel joint 2850. The elongate tube applicator 2800 can comprise a proximal handle 2820, and a shaft 2802 extending distally from the proximal handle 2820. A proximal end 2804 of the shaft 2802 can be coupled to the proximal handle 2820 and a distal end 2806 of the shaft 2802 can be coupled to an elongate tube engagement component 2830. The swivel joint 2850 can bisect the shaft 2802 into a first shaft portion 2808 and a second shaft portion 2810. The first shaft portion 2808 can be proximal relative to the second shaft portion 2810. For example, the first shaft portion 2808 can be coupled to the proximal handle 2820 and the second shaft portion 2810 can be coupled to the elongate tube engagement component 2830. The swivel joint 2850 can be configured to allow the first shaft portion 2808 to both rotate and bend relative to the second shaft portion 2810 of the shaft 2802. In some cases, the swivel joint 2850 can be configured to allow up to about 360 degrees rotation of the first shaft portion 2808 around a longitudinal axis of the elongate tube applicator 2800 relative to the second shaft portion 2810. In some cases, the swivel joint 2850 can be configured to allow bending of the first shaft portion 2808 relative to the second shaft portion 2810, such as to form an angle of between 90 degrees and 180 degrees between the first and second shaft portions 2808, 2810. In some cases, the swivel joint 2850 can be a locking swivel joint such that the first shaft portion 2808 and the second shaft portion 2810 can be rotated and/or bent to a particular configuration and maintained in that configuration.

In some cases, the position of the swivel joint 2850 on the shaft 2802 can be predetermined based at least in part on the location of the target site relative to the access opening through which an operator inserts the elongate tube applicator 2800. For example, a distance between the swivel joint 2850 can be based on a desired range of motion of the elongate tube engagement component 2830 relative to the proximal handle 2820. In some cases, the swivel joint 2850 can be on a portion of the shaft 2802 closer to the distal end 2806 than to the proximal end 2804 such that the first shaft portion 2808 is longer than the second shaft portion 2810.

The elongate tube applicator 2800 can comprise one or more other features of the elongate tube applicator 2600 described with reference to FIGS. 26 and 27. For example, the elongate tube engagement component 2830 can comprise a plurality of extensions 2832 each comprising a laterally extending portion 2834 extending laterally relative to the shaft 2802. Each of the laterally extending portions 2834 can comprise a distally extending portions 2836 extending distally from the laterally extending portion 2834. The laterally extending portion 2834 and the distally extending portion 2836 can be perpendicular or substantially perpendicular to one another. Each of the plurality of distally extending portions 2836 can comprise thereon a recess 2838 on a surface 2840 oriented toward a longitudinal axis of the shaft 2802. The plurality of recesses 2838 can be configured to receive a corresponding portion of the elongate tube 1610 while the elongate tube 1610 is positioned over and coupled to the target tissue.

Figure 29:
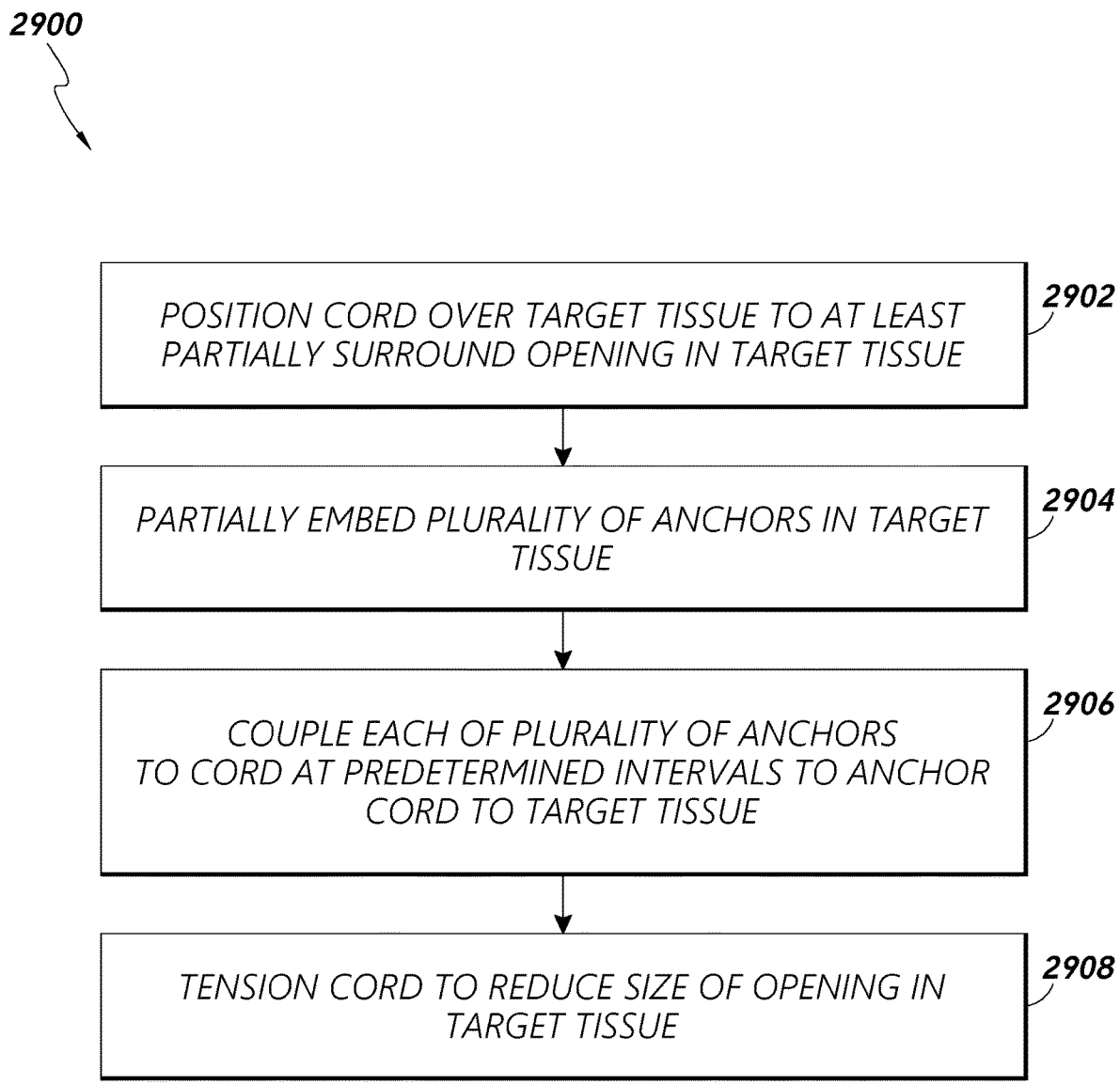
FIG. 29 a process flow diagram of an example of a process for closing a tissue opening.

FIG. 29 is a process flow diagram of an example of a process 2900 for closing a tissue opening using one or more suture systems described herein, including the suture systems 1600, 1700 described with reference to FIGS. 16 and 17. In block 2902, the process 2900 can involve positioning a cord over a target tissue to at least partially surround an opening in the target tissue. As described herein, the target tissue can comprise a heart wall. For example, the cord can be positioned over ventricular heart wall tissue in an apex region of the heart. In block 2904, the suturing process 2900 can involve partially embedding a plurality of anchors in the target tissue. In block 2906, the closing process 2900 can involve coupling each of the plurality of anchors to the cord at predetermined intervals to anchor the cord to the target tissue. The anchors can be distributed along the cord positioned to at least partially surround the opening to anchor the cord to the target tissue. In block 2908, the closing process 2900 can involve tensioning the cord to reduce a size of the opening. In some cases, tensioning the cord can comprise closing the opening around a surgical instrumentation inserted within the opening during a surgical procedure. In some cases, tensioning the cord can comprise closing the opening after completion of the surgical procedure. For example, tensioning the cord can comprise closing the opening around a plurality of tethers extending through the opening after completing deployment of the tethers.

In some cases, an elongate tube comprising a lumen extending therethrough can be provided. At least a portion of the cord can be slidably received within the lumen of the elongate tube. The cord can be longer than the elongate tube such that respective portions of the cord can extend beyond ends of the elongate tube. Suturing the opening can comprise positioning the elongate tube over the target tissue to at least partially surround the opening in the target tissue. Coupling each of the plurality of anchors to the cord at predetermined intervals can comprise coupling each of the plurality of anchors at predetermined interval to the elongate tube to anchor the elongate tube, comprising the cord extending therethrough, to the target tissue.

Suturing the opening can comprise positioning an elongate tube applicator over the target tissue and engaging the elongate tube using the elongate tube applicator to maintain the elongate tube in a predetermined shape while the elongate tube is anchored to the target tissue. The elongate tube applicator can comprise a shaft extending distally from a proximal handle, and an elongate tube engagement component coupled to a distal end of the shaft. Engaging the elongate tube can comprise positioning corresponding portions of the elongate tube in respective recesses on surfaces of the elongate tube engagement component which are oriented toward a longitudinal axis of the shaft.

As described herein, a fastener can be coupled to corresponding portions of one of the suture or the elongate tube to maintain the corresponding portions of the cord or the elongate tube at predetermined positions relative to one another such that the cord or the elongate tube at least partially surrounds the opening in the target tissue. In some cases, suturing the opening can comprise inserting the corresponding portions of the cord or the elongate tube through two openings in the fastener to maintain the corresponding portions of the suture or the elongate tube at predetermined positions relative to one another. A plurality of anchors can be coupled to the fastener and partially embedding the plurality of anchors into the target tissue to anchor the fastener to the target tissue.

Portions of the elongate tube proximal of the fastener can be inserted into a lumen of a tourniquet, such as to facilitate maintaining the elongate tube in a configuration to at least partially surround the opening. Portions of the cord proximal of the fastener can be threaded through the lumen of a tourniquet. The fastener and/or the tourniquet can facilitate maintaining the elongate tube, and the cord extending therethrough, in a configuration to at least partially surround the opening in the target tissue. As described herein, the cord can be tensioned during a surgical procedure to close the opening around a surgical instrumentation inserted within the opening. Tensioning the cord to reduce the size of the opening temporarily can comprise fixating a portion of the suture around a suture engagement feature on a proximal portion of the tourniquet.

In some cases, partially embedding a plurality of anchors in the target tissue and coupling each of the plurality of anchors can comprise deploying a plurality of sutures. In some cases, partially embedding a plurality of anchors in the target tissue and coupling each of the plurality of anchors can comprise deploying a plurality of staples.

As described herein, tensioning of traditional purse-string sutures can result in abrasion and/or breakage of tethers extending through an opening in a target tissue. In some cases, a plurality of tethers extending through an opening in a target tissue can be threaded through an inner lumen of a protective sleeve. The protective sleeve can prevent or reduce abrasion of the tethers to reduce and/or eliminate damage to the tethers. The protective sleeve can be used in combination with one or more purse-string suture patterns traditionally used to close tissue openings. In some cases, the protective sleeve can be used in combination with one or more suture patterns described herein.

Figure 30B:
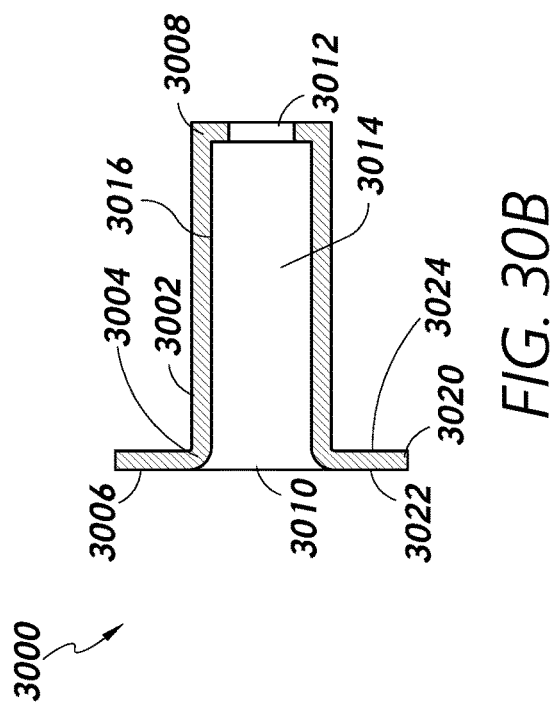
FIGS. 30A, 30B, 30C are a perspective view, cross-sectional view and distal plan view, of an example of a flexible elongate tube.
Figure 30C:
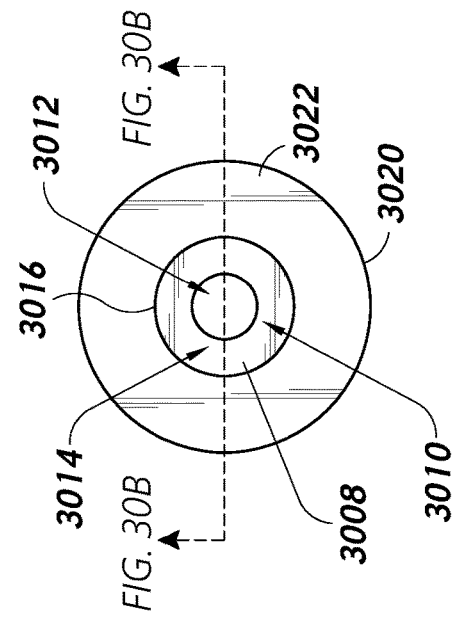
Figure 30A:
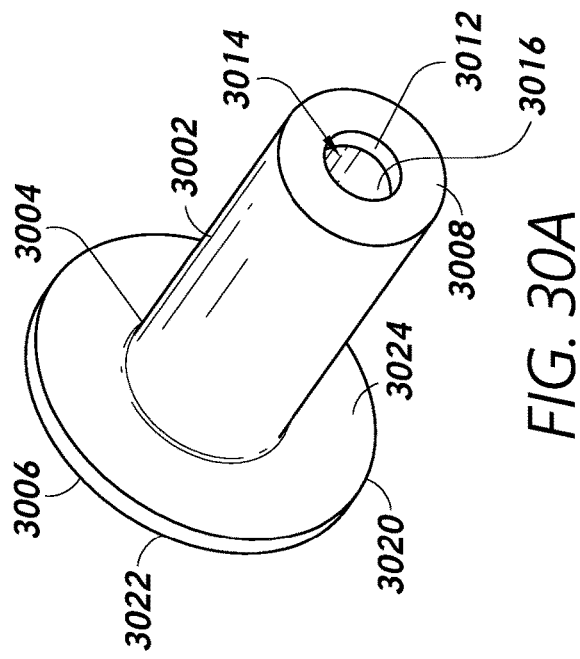

FIGS. 30A through 30C show various views of an example of a flexible elongate tube 3000 configured to be positioned within an opening in a target tissue. FIG. 30A is a perspective view, FIG. 30B is a cross-sectional view along a longitudinal axis, and FIG. 30C is a plan view from a proximal end 3006, of the flexible elongate tube 3000. Referring to FIG. 30A, the flexible elongate tube 3000 can comprise an elongate portion 3002. A flange 3020 can be associated with a proximal end 3004 of the elongate portion 3002. A lumen 3014 can extend along an entire length of the elongate portion 3002 such that a proximal opening 3010 of the lumen 3014 is at a proximal end 3006 of the flexible elongate tube 3000 and a distal opening 3012 of the lumen 3014 is at a distal end 3008 of the flexible elongate tube 3000. An inner lumen surface 3016 can define the lumen 3014. In some cases, the proximal opening 3010 can be larger than the distal opening 3012. For example, at least a portion of the distal end 3008 can be perpendicular or substantially perpendicular to the longitudinal axis of the flexible elongate tube 3000. The longitudinal axis of the flexible elongate tube 3000 can extend between the proximal end 3006 and the distal end 3008 of the flexible elongate tube 3000.

The lumen 3014 can be configured to receive a plurality of tethers extending through the opening in the target tissue. For example, the plurality of tethers can extend through the lumen 3014, through the distal opening 3012 and the proximal opening 3010. The flexible elongate tube 3000 can be configured to be positioned within the opening in the target tissue and collapse along the longitudinal axis of the flexible elongate tube 3000 and around the plurality of tethers extending therethrough. For example, the elongate portion 3002 can collapse along the longitudinal axis around the plurality of tethers, such as due to forces exerted thereupon by the target tissue adjacent to the opening in the target tissue.

As described herein, the flange 3020 can be associated with a proximal end 3004 of the elongate portion 3002. The flange 3020 can extend laterally from the proximal end 3004 of the elongate portion 3002. For example, the flange 3020 can be perpendicular or substantially perpendicular relative to the longitudinal axis of the flexible elongate tube 3000. The flange 3020 can comprise a proximal surface 3022 and a distal surface 3024. The proximal surface 3022 can be configured to be oriented toward a first surface of the target tissue and the distal surface 3024 can be configured to be oriented away from the first surface of the target tissue, while the flexible elongate tube 3000 is positioned at the desired position within the opening in the target tissue. The elongate portion 3002 can be configured to be entirely or substantially entirely be positioned within the opening in the target tissue. For example, the flexible elongate tube 3000 can be inserted in the opening such that the proximal surface 3022 is positioned over and in contact with the first surface of the target tissue. In some cases, the distal end 3008 of the flexible elongate tube 3000 can be in the opening proximate or adjacent to a second surface of the target tissue. For example, the elongate portion 3002 can have a length equal or substantially equal to a length of the opening in the target tissue. In some cases, the distal end 3008 can be flush or substantially flush with the second surface of the target tissue. In some cases, the distal end 3008 of the flexible elongate tube 3000 can be in the opening within the target tissue.

In some cases, the flange 3020 can be configured to facilitate positioning of the flexible elongate tube 3000 at a desired depth into the opening in the target tissue. For example, the flange 3020 can prevent or reduce over-insertion of the flexible elongate tube 3000 into the opening. In some cases, the flange 3020 can facilitate positioning of the flexible elongate tube 3000 such that the distal end 3008 does not extend beyond the length of the opening, for example such that the distal end 3008 is flush or substantially flush with the second surface of the target tissue.

In some cases, the target tissue can comprise the heart wall, including the left ventricular heart wall. In some cases, the flexible elongate tube 3000 can be configured to be extended through one or more of the pericardium, epicardium, myocardium and endothelium. In some cases, the distal end 3008 of the flexible elongate tube 3000 can be flush or substantially flush with a ventricular oriented surface portion of the endothelium. In some cases, the distal end 3008 can be within the heart wall. In some cases, the flange 3020 of the flexible elongate tube 3000 can be positioned over an externally oriented surface of the heart wall. In some cases, the flange 3020 can be positioned against an externally oriented surface portion of the pericardium. In some cases, the flange 3020 can be positioned against an externally oriented surface portion of the epithelium.

FIGS. 31A through 31C show various views of another example of a flexible elongate tube 3100 configured to be positioned within an opening in a target tissue. FIG. 31A is a perspective view, FIG. 31B is a cross-sectional view along a longitudinal axis, and FIG. 31C is a plan view from a proximal end 3106, of the flexible elongate tube 3100. The flexible elongate tube 3100 can comprise an elongate portion 3102 and a flange 3120 extending from a proximal end 3104 of the elongate portion 3102, where the flange 3120 can comprise a reinforced portion 3126. The flange 3120 can extend laterally outward from the elongate portion 3102, including being perpendicular or substantially perpendicular to a longitudinal axis of the flexible elongate tube 3100. The longitudinal axis of the flexible elongate tube 3100 can extend between the proximal end 3106 and a distal end 3108 of the flexible elongate tube 3100. In the example shown, the reinforced portion 3126 can extend circumferentially around the flange 3120. The reinforced portion 3126 can form at least a portion of an outer edge portion 3128 of the flange 3120. The reinforced portion 3126 can provide additional mechanical strength for the flange 3120, such as to facilitate secure positioning of the flange 3120 against the target tissue. In some cases, one or more anchors (e.g., sutures) can be coupled to the reinforced portion 3126 for securing the reinforced portion 3126 to the target tissue.

FIG. 31C shows that the reinforced portion 3126 can extend continuously circumferentially around the flange 3120, for example forming the entirety or substantially the entirety of the outer edge portion 3128. In some cases, the flange 3120 can comprise a circular or substantially circular shape. For example, the outer edge portion 3128 can form a circle. It will be understood that a reinforced portion may not extend continuously around an outer edge portion. In some cases, the reinforced portion can be at intervals, such as regular intervals, around the outer edge portion. In some cases, the reinforced portion can be at a position in addition to or instead of than an outer edge portion of the flange, including for example a center portion of the flange. In some cases, the flange can be entirely or substantially entirely reinforced.

The flexible elongate tube 3100 can have one or more other features of the flexible elongate tube 3000 described with reference to FIG. 30. For example, a lumen 3114 can extend along an entire or substantially entire length of the elongate portion 3102 such that a proximal opening 3110 is at the proximal end 3004 of the elongate portion 3102 and a distal opening 3112 is at a distal end 3108 of the elongate portion 3102. The lumen 3114 can be configured to receive a plurality of tethers and collapse along a longitudinal axis of the flexible elongate tube 3100 around the plurality of tethers. The flange 3120 can comprise a proximal surface 3122 and a distal surface 3124, where the proximal surface 3122 can be configured to be oriented toward the target tissue and the distal surface 3124 can be configured to be oriented away from the target tissue, while the flexible elongate tube 3100 is positioned into the opening in the target tissue. An inner lumen surface 3116 can define the lumen 3114. In some cases, the proximal opening 3110 can be larger than the distal opening 3112. For example, at least a portion of the distal end 3108 can be perpendicular or substantially perpendicular to the longitudinal axis of the flexible elongate tube 3100.

FIGS. 32A through 32C show various views of yet another example of a flexible elongate tube 3200 configured to be positioned within an opening in a target tissue. FIG. 32A is a perspective view, FIG. 32B is a cross-sectional view along a longitudinal axis, and FIG. 32C is a plan view from a proximal end 3206, of the flexible elongate tube 3200. The longitudinal axis of the flexible elongate tube 3200 can extend between the proximal end 3206 and a distal end 3208 of the flexible elongate tube 3200. The flexible elongate tube 3200 can comprise a flange 3220 comprising a reinforced portion 3226, where the flange 3220 can have a non-rounded shape. For example, the flange 3220 can comprise a rectangular shape, including a square shape. The reinforced portion 3226 can extending circumferentially around the flange 3220. For example, the reinforced portion 3226 can form at least a portion of an outer edge portion 3228 of the rectangular shaped flange 3220.

The flexible elongate tube 3200 can have one or more other features of the flexible elongate tube 3100 described with reference to FIG. 31. The flange 3220 can extend from a proximal end 3204 of an elongate portion 3202 of the flexible elongate tube 3200. A lumen 3214 can extend along an entire length of the elongate portion 3202 such that a proximal opening 3210 is at the proximal end 3204 and a distal opening 3212 is at a distal end 3208 of the elongate portion 3202. The lumen 3214 can be configured to receive a plurality of tethers and collapse along the longitudinal axis of the flexible elongate tube 3200 around the plurality of tethers. The flange 3220 can comprise a proximal surface 3222 configured to be oriented toward the target tissue and a distal surface 3124 configured to be oriented away from the target tissue. An inner lumen surface 3216 can define the lumen 3214. In some cases, the proximal opening 3210 can be larger than the distal opening 3212. For example, at least a portion of the distal end 3208 can be perpendicular or substantially perpendicular to the longitudinal axis of the flexible elongate tube 3200.

Figure 33A:
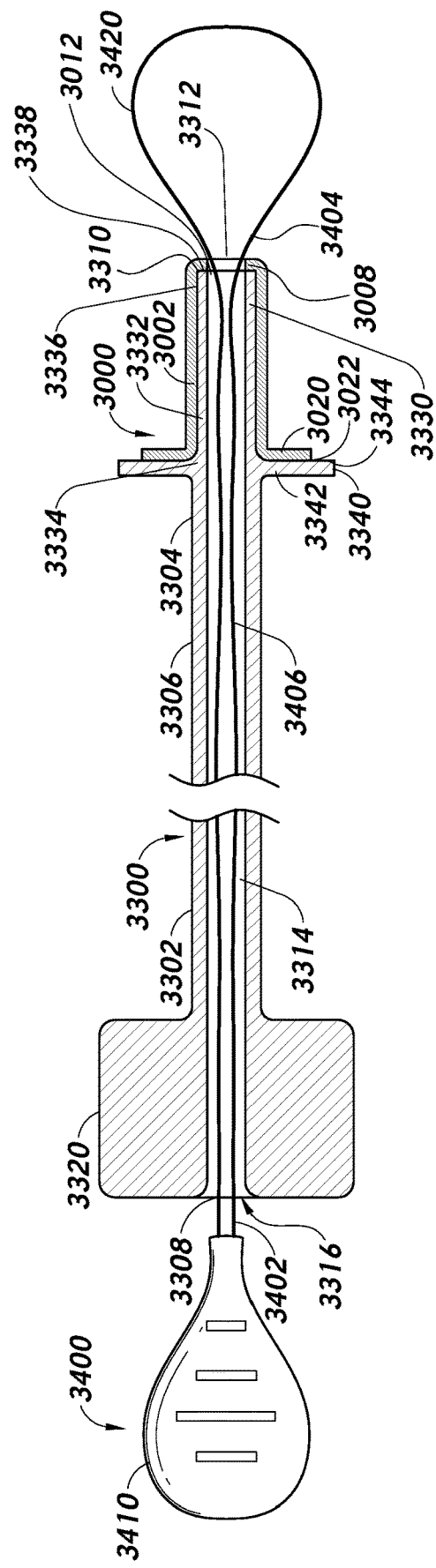
FIG. 33A is a cross-sectional view.
Figure 33B:
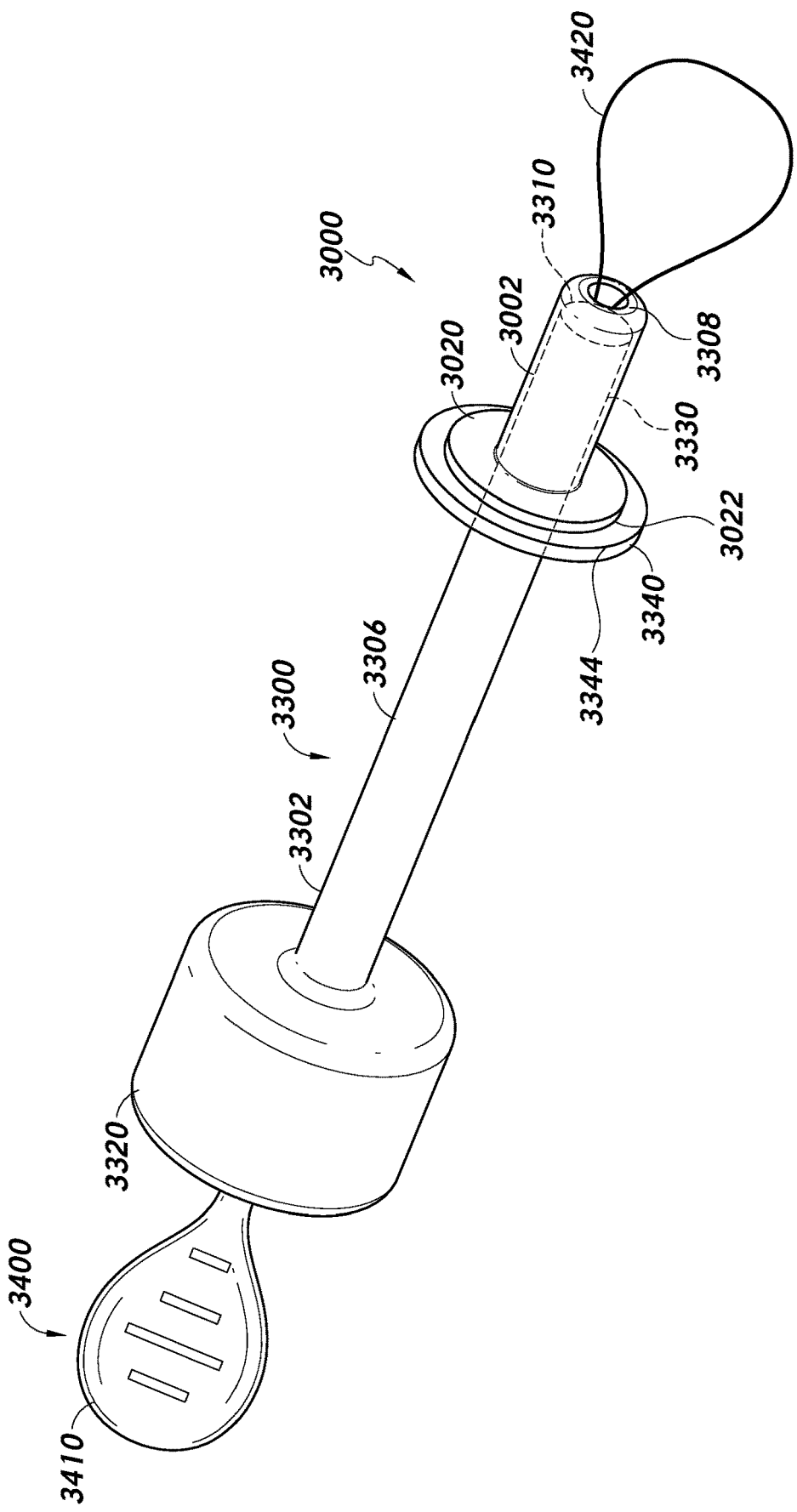
FIG. 33B is a perspective view, of an example of a deployment applicator for deploying a flexible elongate tube.

FIG. 33A is a cross-sectional view, and FIG. 33B is a perspective view, of an example of a deployment applicator 3300 configured to deploy one or more flexible elongate tubes described herein. In the example shown, the flexible elongate tube 3000 described with reference to FIG. 30 is engaged with an elongate tube engagement component 3330 associated a distal portion 3304 of the deployment applicator 3300. The elongate tube engagement component 3330 can be configured to engage with the flexible elongate tube 3000 to facilitate insertion of the flexible elongate tube 3000 into an opening in a target tissue. The deployment applicator 3300 can comprise a handle 3320 associated with a proximal portion 3302. A shaft 3306 can extend distally from the handle 3320, for example extending between the handle 3320 and the elongate tube engagement component 3330.

The elongate tube engagement component 3330 can comprise an elongate engagement portion 3332 and a ridge 3340 associated with a proximal portion 3334 of the elongate engagement portion 3332. The elongate portion 3002 of the flexible elongate tube 3000 can be configured to be positioned over the elongate engagement portion 3332. For example, an outer surface portion 3336 of the elongate engagement portion 3332 can have a shape and size such that the elongate portion 3002 can fit snugly over and around the elongate engagement portion 3332. The elongate engagement portion 3332 can be received within at least a portion of the lumen 3014 of the flexible elongate tube 3000 and the outer surface portion 3336 can be in contact with an inner lumen surface 3016 of the lumen 3014. In some cases, the elongate engagement portion 3332 and the lumen 3014 of the elongate flexible tube 3000 can comprise a cylindrical or substantially cylindrical shape. For example, the inner lumen surface 3016 can comprise at least a portion that forms a cylindrical shape. In some cases, a diameter of the elongate engagement portion 3332 can be the same or similar to that of the lumen 3014.

In some cases, the entirety of the elongate portion 3002 of the flexible elongate tube 3000 can be positioned over the elongate engage portion 3332 such that at least a portion of the distal end 3008 of the flexible elongate tube 3000 can be positioned over the distal end 3338 of the elongate tube engagement component 3330. Positioning the distal end 3008 of the flexible elongate tube 3000 over the distal end 3338 of the elongate tube engagement component 3330 can facilitate maintaining the elongate flexible tube 3000 at a desired position relative to the elongate tube engagement component 3330 as the elongate tube engagement component 3330 is pushed into the opening in the target tissue.

The ridge 3340 can extend laterally from the elongate engagement portion 3332. For example, the ridge 3340 can extend circumferentially around the elongate engagement portion 3332. In some cases, the ridge 3340 can extend laterally and be perpendicular or substantially perpendicular relative to the elongate engagement portion 3332. The ridge 3340 can comprise a proximal surface 3342 and a distal surface 3344. The elongate engagement portion 3332 can extend distally from the ridge 3340. The flexible elongate tube 3000 can be positioned around the elongate tube engagement component 3330 such that the elongate portion 3002 of the flexible elongate tube 3000 is around and/or in contact with the elongate engagement portion 3332. The proximal surface 3022 of the flange 3020 of the flexible elongate tube 3000 can be positioned against the distal surface 3344 of the ridge 3340. In some cases, positioning the proximal surface 3022 of the flange 3020 on the flexible elongate tube 3000 against the distal surface 3344 of the ridge 3340 on the elongate tube engagement component 3330 can facilitate delivery of the flexible elongate tube 3000 to the desired position within the opening in the target tissue. For example, the proximal movement of the flexible elongate tube 3000 is reduced or prevented as the flexible elongate tube 3000 is inserted into the opening in the target tissue.

Referring again to FIG. 33A, a lumen 3314 can extend along an entire length of the deployment applicator 3300, for example from a proximal end 3308 to a distal end 3310 of the deployment applicator 3300. The lumen 3314 can be configured to receive a plurality of tethers extending from the opening in the target tissue. As described in further detail herein, the plurality of tethers can be threaded into the lumen 3314 through a distal opening 3312 of the lumen 3314 at the distal end 3310 of the deployment applicator 3300. The distal opening 3312 can be aligned with the distal opening 3012 of the flexible elongate tube 3000. The plurality of tethers can be threaded through the length of the lumen 3314 and then out of the lumen 3314 through a proximal opening 3316 of the lumen 3314 at the proximal end 3308 of the deployment applicator 3300. After the flexible elongate tube 3000 is positioned in the opening of the target tissue, the deployment applicator 3300 can be retracted to leave the flexible elongate tube 3000 in the opening and corresponding portions of the plurality of tethers extending through the lumen 3014 of the flexible elongate tube 3000.

In some cases, a tether snare 3400 can be used to thread one or more tethers through the lumen 3314 of the deployment applicator 3300. In FIG. 33A, a tether snare 3400 can be positioned through the lumen 3314. The tether snare 3400 can be configured to guide one or more tethers through the lumen 3314. The tether snare 3400 can comprise a handle 3410 associated with a proximal portion 3402 and a snare portion 3420 associated with a distal portion 3404. A shaft portion 3406 can extend between the snare portion 3420 and the handle 3410. For example, the shaft portion 3406 can extend distally from the handle 3410, coupling the handle 3410 and the snare portion 3420. The snare portion 3420 and at least a portion of the shaft portion 3406 can be advanced through the lumen 3314 of the deployment applicator 3300 such that the snare portion 3420 extends beyond the distal end 3310 of the deployment applicator 3300. The tether snare 3400 can be loaded into the deployment applicator 3300 such that the snare portion 3420 can extend distally from the distal opening 3312 and the handle 3410 can extend proximally from the proximal opening 3316. The snare portion 3420 can be used to capture one or more tethers to thread the one or more tethers through the lumen 3314. The tether snare 3400 can be retracted through the distal opening 3312, the lumen 3314 and then the proximal opening 3316 such that the snare portion 3420 having the one or more tethers captured thereon can be retracted through the lumen 3314 to thread the one or more tethers through the lumen 3314.

FIG. 33B is a perspective view of the flexible elongate tube 3000 engaged by the elongate tube engagement component 3330 associated with the distal portion 3304 of the deployment applicator 3300. The elongate portion 3002 of the flexible elongate tube 3000 can be around and/or in contact with the elongate engagement portion 3332 of the deployment applicator 3300. The proximal surface 3022 of the flange 3020 of the flexible elongate tube 3000 can be positioned in contact with the distal surface 3344 of the ridge 3340 of the elongate tube engagement component 3330. The tether snare 3400 is shown as being positioned through the deployment applicator 3300. The snare portion 3420 is shown as extending distally beyond the distal end 3310 and the handle 3410 is shown as extending proximally from the proximal end 3308 of the deployment applicator 3300.

Figure 34:
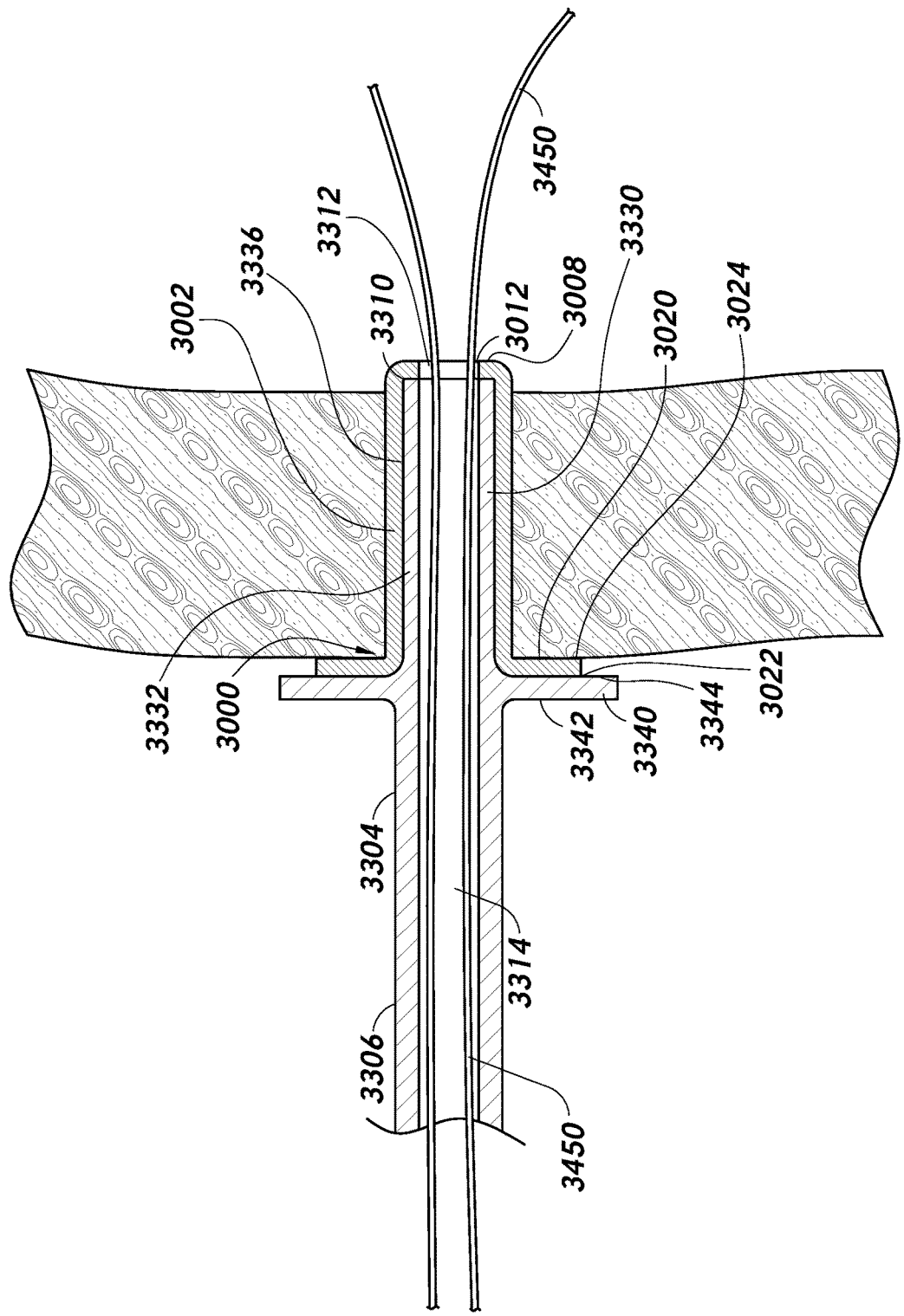
FIG. 34 is a cross-sectional view of using the deployment applicator of FIGS. 33A and 33B to deploy a flexible elongate tube into a target opening.

FIG. 34 is a cross-sectional view of a portion of the deployment applicator 3300 inserted within an opening in the target tissue to facilitate deployment of the flexible elongate tube 3000 into the opening. A portion of the shaft 3306 is shown. The elongate tube engagement component 3330 associated with the distal portion 3304 of the deployment applicator 3300 can be positioned to facilitate the deployment of the flexible elongate tube 3000. For example, at least a portion of the elongate tube engagement component 3330 can be advanced into the opening to position the flexible elongate tube 3000 at a target position within the opening. The flexible elongate tube 3000 can be engaged with the elongate tube engagement component 3330 such that the elongate portion 3002 can be positioned over the elongate engagement portion 3332 of the elongate tube engagement component 3330. The flange 3020 of the flexible elongate tube 3000 can be positioned against the ridge 3340 of the elongate tube engagement component 3330. The distal surface 3344 of the ridge 3340 of the elongate tube engagement component 3330 can be in contact with the proximal surface 3022 of the flange 3020 of the flexible elongate tube 3000. The elongate engagement portion 3332 can be received within the lumen 3014 of the flexible elongate tube 3000 and the outer surface portion 3336 of the elongate engagement portion 3332 can be in contact with the inner lumen surface 3016 of the flexible elongate tube 3000. At least a portion of the distal end 3008 of the flexible elongate tube 3000 can be positioned over the distal end 3310 of the elongate tube engagement component 3330. The distal opening 3312 can be aligned with the distal opening 3012 of the flexible elongate tube 3000. The deployment applicator 3300 can be advanced into the opening such that the ridge 3340 of the elongate tube engagement component 3330 is pressed against the flange 3020 of the flexible elongate tube 3000, which is pressed against a first surface of the target tissue. In some cases, a length of the flexible elongate tube 3000 can be selected such that the distal end 3008 of the flexible elongate tube 3000 can be proximate or adjacent to a second surface of the target tissue while the flange 3020 of the flexible elongate tube 3000 is positioned against the first surface of the target tissue. The distal surface 3024 of the flange 3020 of the flexible elongate tube 3000 can be configured to be in contact with the first surface of the target tissue. The proximal surface 3022 of the flange 3020 of the flexible elongate tube 3000 can be configured to be in contact with the distal surface 3344 of the ridge 3340 of the elongate tube engagement component 3330. The proximal surface 3342 of the ridge 3340 of the elongate tube engagement component 3330 can be oriented away from the first surface of the target tissue.

In FIG. 34, a plurality of tethers 3450 is shown as extending through the lumen 3314 of the deployment applicator 3300. Corresponding portions of the tethers 3450 extend into the lumen 3314 through the distal opening 3312 of the lumen 3314. As described herein, after the flexible elongate tube 3000 is placed at a desired position within the opening, the deployment applicator 3300 can be retracted, leaving respective portions of the plurality of tethers 3450 extending through the lumen 3014 of the flexible elongate tube 3000.

Figure 35:
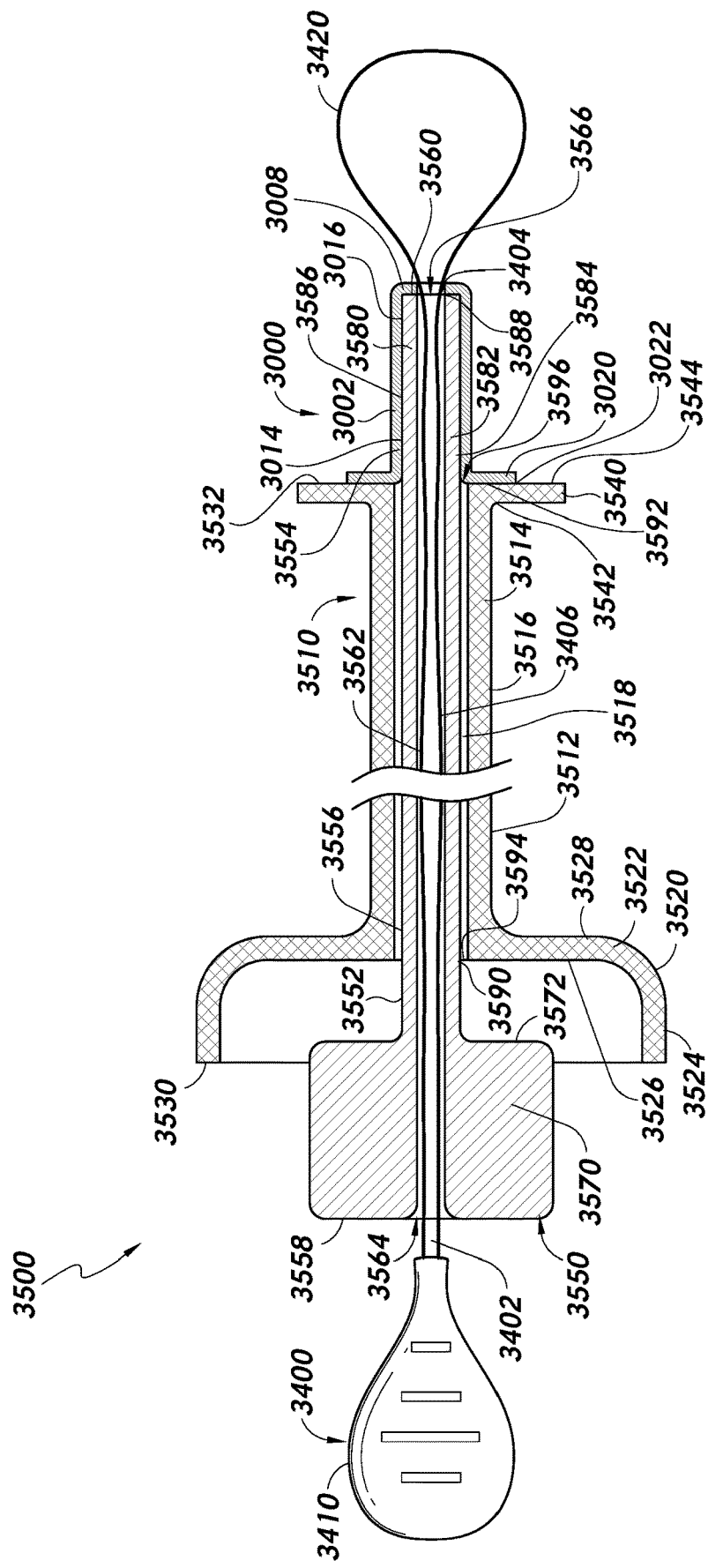
FIG. 35 is a cross-sectional view of an example of a deployment applicator for deploying a flexible elongate tube, where the deployment applicator comprises an inner member and an outer sheath.

FIG. 35 is a cross-sectional view of another example of a deployment applicator 3500. The deployment applicator 3500 can comprise an outer sheath member 3510 and an inner member 3550. The outer sheath member 3510 can comprise a lumen 3518 through which at least a portion of the inner member 3550 can extend. FIG. 35 shows a flexible elongate tube 3000 engaged with an elongate tube engagement component 3580 associated with a distal portion 3554 of the inner member 3550.

The inner member 3550 can comprise a handle 3570 associated with a proximal portion 3552. A shaft 3556 can extend between the handle 3570 and the elongate tube engagement component 3580 associated with the distal portion 3554. The elongate tube engagement component 3580 can comprise an elongate engagement portion 3582 which can be received within the lumen 3014 of the flexible elongate tube 3000. The flexible elongate tube 3000 can be oriented with the flange 3020 over a proximal portion 3584 of the elongate tube engagement component 3580. The distal end 3008 of the flexible elongate tube 3000 can be positioned against the distal end 3588 of the elongate tube engagement component 3580. In some cases, the elongate tube engagement component 3580 can have a shape and size such that the inner lumen surface 3016 of the flexible elongate tube 3000 can be positioned around and in contact with an outer surface portion 3586 of the elongate tube engagement component 3580. For example, an outer diameter of the elongate tube engagement component 3580, such as an outer diameter of the elongate engagement portion 3582, and a shape of the outer surface portion 3586 can be the same or similar to a diameter and shape of the lumen 3014 of the flexible elongate tube 3000. In some cases, the outer surface portion 3586 and the lumen 3014 of the flexible elongate tube 3000 can both comprise a cylindrical or substantially cylindrical shape.

A lumen 3562 can through the entire length of the inner member 3550, for example from a proximal end 3558 to a distal end 3560 of the inner member 3550. The distal end 3560 of the inner member 3550 can be the distal end 3588 of the elongate tube engagement component 3580. The lumen 3562 can be configured to receive a plurality of tethers extending from the opening in the target tissue. The inner member 3550 can be retracted after delivering the flexible elongate tube 3000 to a desired position within the opening, leaving the flexible elongate tube 3000 in the desired position and the plurality of tethers extending through the lumen 3014 of the flexible elongate tube 3000.

In some cases, a tether snare can be used to thread one or more of the tethers through the lumen 3562 of the inner member 3550. In FIG. 35, a tether snare 3400 as described with reference to FIG. 33 can be positioned through the lumen 3562. As described herein, the tether snare 3400 can comprise a handle 3410 associated with a proximal portion 3402 and a snare portion 3420 associated with a distal portion 3404. A shaft portion 3406 can extend between the snare portion 3420 and the handle 3410. The snare portion 3420 and at least a portion of the shaft portion 3406 can be advanced through the lumen 3562 of the inner member 3550 such that the snare portion 3420 extends distally beyond the distal end 3560 of the inner member 3550. For example, the tether snare 3400 can be loaded into the deployment applicator 3500 such that the snare portion 3420 can extend distally from a distal opening 3566 of the lumen 3562 and the handle 3410 can extend proximally from a proximal opening 3564 of the lumen 3562. The snare portion 3420 can be used to capture one or more tethers to thread the one or more tethers through the lumen 3562. The tether snare 3400 can be retracted such that the snare portion 3420 having the one or more tethers captured thereon can be retracted through the lumen 3562 to thread the one or more tethers through the lumen 3562.

Referring again to FIG. 35, a portion of the inner member 3550 can be slidably received within the lumen 3518 of the outer sheath member 3510. The outer sheath member 3510 can comprise a ridge 3540 associated with a distal portion 3514 of the outer sheath member 3510. For example, the ridge 3540 can comprise at least a portion that extends laterally. The ridge 3540 can extend perpendicularly or substantially perpendicularly relative to a longitudinal axis of the outer sheath member 3510. The longitudinal axis of the outer sheath member 3510 can extend along a dimension extending between a proximal end 3590 and a distal end 3592 of the outer sheath member 3510. In some cases, the ridge 3540 can comprise the distal end 3592 of the outer sheath member 3510. The distal end 3592 can extend perpendicularly or substantially perpendicularly relative to the longitudinal axis of the outer sheath member 3510. A handle engagement portion 3520 can be associated with a proximal portion 3512 of the outer sheath member 3510. For example, the handle engagement portion 3520 can be coupled to the proximal end 3590 of the of the outer sheath member 3510. A shaft 3516 can extend between the handle engagement portion 3520 and the ridge 3540. The lumen 3518 of the outer sheath member 3510 can extend from the proximal end 3590 to the distal end 3592 of the outer sheath member 3510, for example, having a proximal opening 3594 at the proximal end 3590 and a distal opening 3596 at the distal end 3592. The inner member 3550 can be configured to be proximally and/or distally translated relative to the outer sheath member 3510 while at least a portion of the inner member 3550 is disposed within the lumen 3518. For example, portions of the inner member 3550 can be configured to be advanced and/or retracted through the proximal and distal openings 3594, 3596.

In some cases, the ridge 3540 can extend laterally from the shaft 3516. The shaft 3516 can be coaxial with the longitudinal axis of the outer sheath member 3510. The ridge 3540 can be perpendicular or substantially perpendicular relative to the shaft 3516. The ridge 3540 can extend circumferentially around the shaft 3516, such as a distal end 3532 of the shaft 3516. The ridge 3540 can comprise a proximal surface 3542 and a distal surface 3544. While the flexible elongate tube 3000 is engaged by the elongate tube engagement component 3580 of the inner member 3550, the flange 3020 of the flexible elongate tube 3000 can be positioned against the ridge 3540 of the elongate tube engagement component 3580. The distal surface 3544 of the ridge 3540 can be in contact with the proximal surface 3022 of the flange 3020 of the flexible elongate tube 3000. As described in further detail herein, positioning the proximal surface 3022 of the flange 3020 of the flexible elongate tube 3000 against the distal surface 3544 of the ridge 3540 on the outer sheath member 3510 can facilitate delivery of the flexible elongate tube 3000 to the desired position within the opening in the target tissue.

The handle engagement portion 3520 of the outer sheath member 3510 can be configured to engage with the handle 3570 of the inner member 3550. The handle engagement portion 3520 can comprise a laterally extending portion 3522 which extends laterally from the proximal end 3590 of the shaft 3516, and a longitudinally extending portion 3524 which extends proximally from the laterally extending portion 3522. The handle engagement portion 3520 can extend circumferentially around the shaft 3516, such as a proximal end 3530 of the shaft 3516. For example, the handle engagement portion 3520 can comprise a cup shape configured to accommodate the handle 3570 of the inner member 3550. In some cases, the laterally extending portion 3522 can be perpendicular or substantially perpendicular to the shaft 3516. The laterally extending portion 3522 can contact the handle 3570 to prevent over-insertion of the inner member 3550 into the lumen 3518 of the outer sheath member 3510. The laterally extending portion 3522 can comprise a proximal surface 3526 and a distal surface 3528. For example, the handle 3570 can contact the proximal surface 3526 for preventing over-insertion of the inner member 3550. Preventing over-insertion of the inner member 3550 relative to the outer sheath member 3510 can facilitate maintaining the inner member 3550 at a desired position relative to the outer sheath member 3510 during delivery of the flexible elongate tube 3000.

In some cases, a handle engagement portion can comprise only a laterally extending portion extending around a shaft to engage with a handle of an inner member, for example without a proximally extending portion. In some cases, the handle engagement portion may not extend circumferentially from a shaft. The handle engagement portion can extend from the shaft at intervals. In some cases, the handle engagement portion can comprise two laterally extending portions extending from opposing positions around the shaft.

Figure 36A:
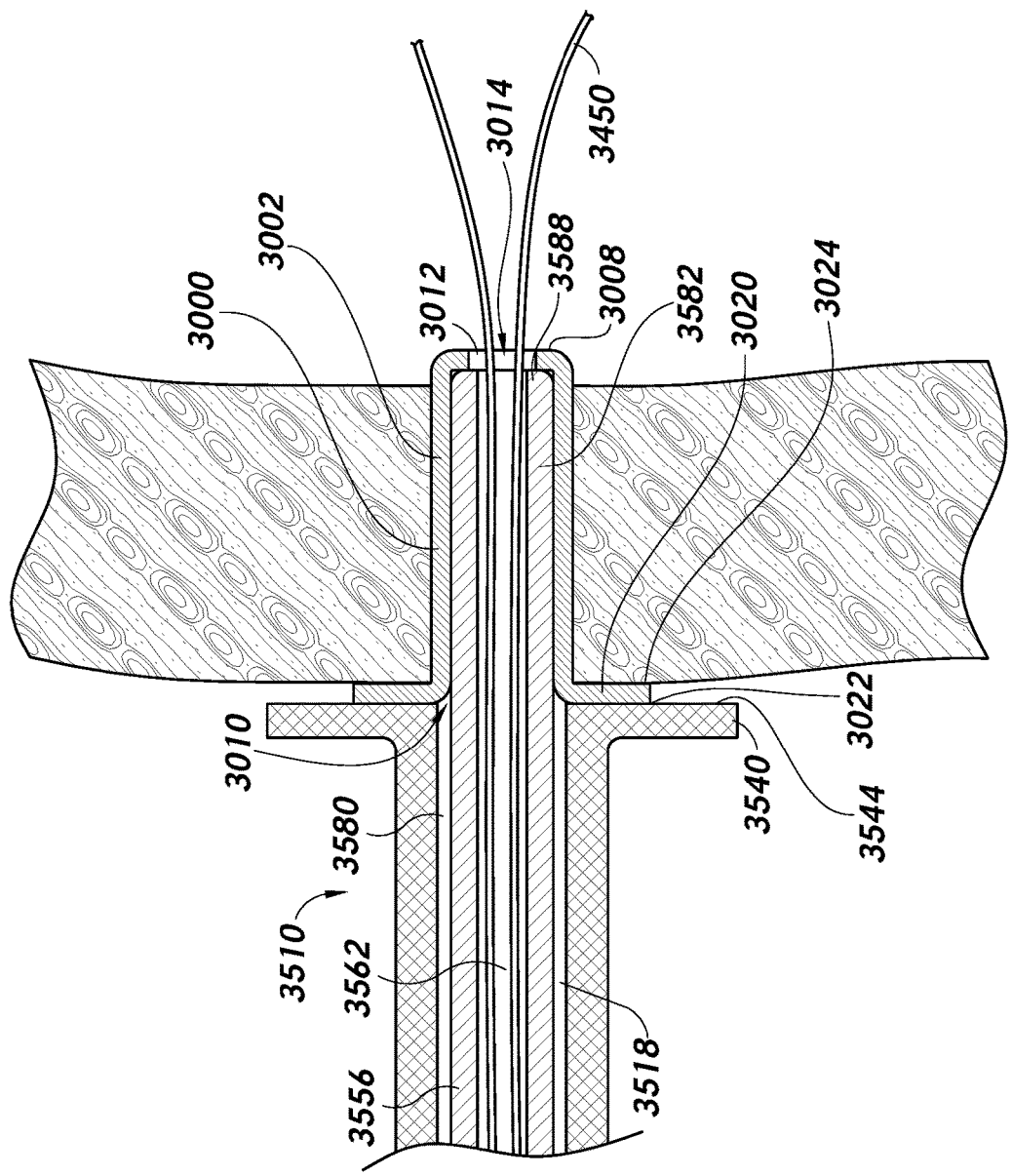
FIGS. 36A and 36B are cross-sectional views of using the deployment applicator of FIG. 35 to deploy a flexible elongate tube into a target opening.
Figure 36B:
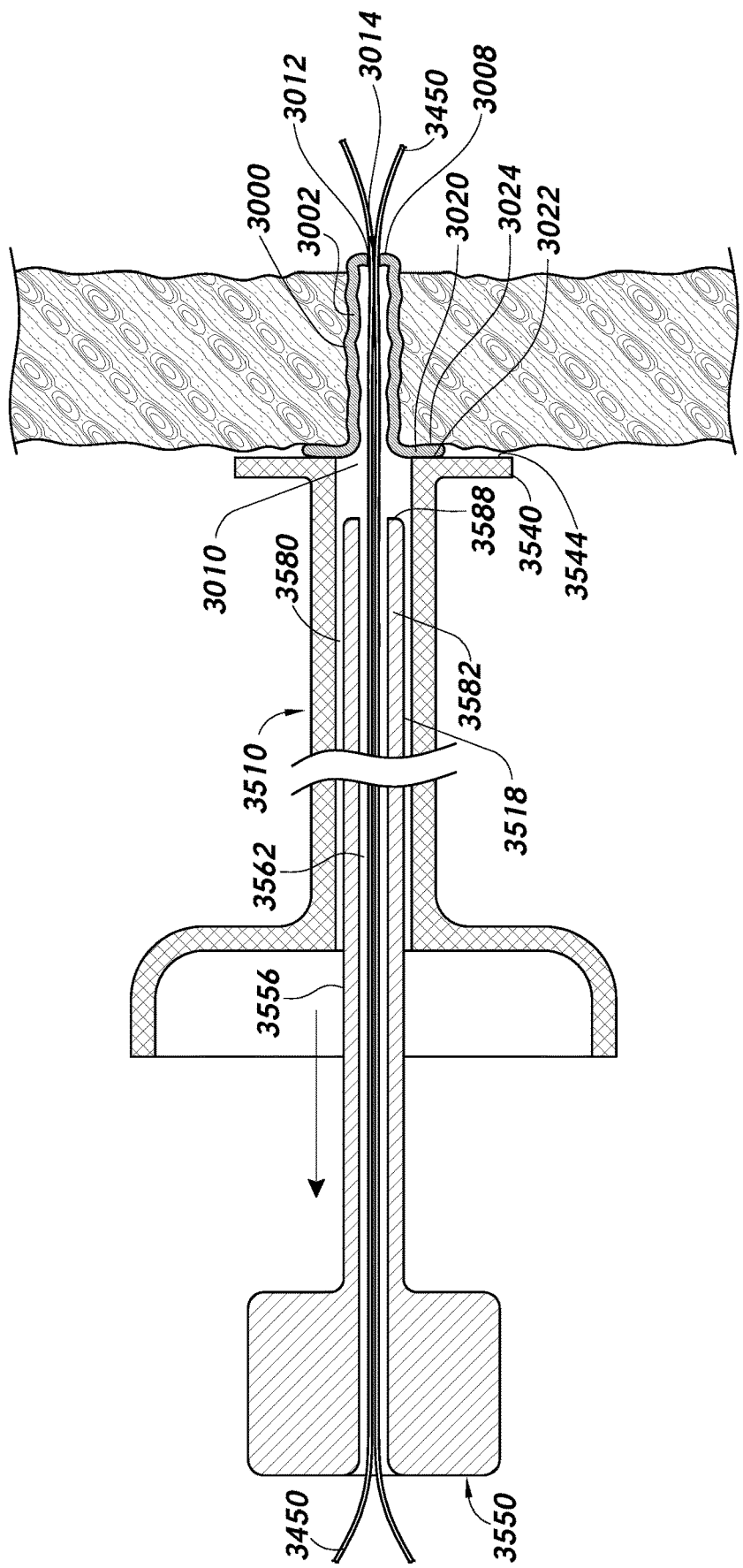

FIGS. 36A and 36B show an example of deploying the flexible elongate tube 3000 from the deployment applicator 3500. Referring to FIG. 36A, the elongate engagement portion 3582 of the inner member 3550 can be inserted into the opening in the target tissue. The elongate portion 3002 of the flexible elongate tube 3000 can be disposed around the elongate engagement portion 3582 such that the elongate portion 3002 is at least partially disposed within the opening in the target tissue. Corresponding portions of a plurality of tethers 3450 can be disposed within the lumen 3562 of the inner member 3550. Maintaining contact between the ridge 3540 of the outer sheath member 3510 and the flange 3020 of the flexible elongate tube 3000 can facilitate positioning of the desired portion of the flexible elongate tube 3000 in the opening in the target tissue. The ridge 3540 of the outer sheath member 3510 can be used to press the flange 3020 of the flexible elongate tube 3000 against a first surface of the target tissue. The distal surface 3544 of the ridge 3540 can be pressed against the proximal surface 3022 of the flange 3020 of the flexible elongate tube 3000 to maintain the flange 3020 against the first surface of the target tissue. For example, the distal surface 3544 of the ridge 3540 can be over and in contact with the proximal surface 3022 of the flexible elongate tube flange 3020 such that the distal surface 3024 of the flexible elongate tube flange 3020 can be over and in contact with the first surface of the target tissue.

The inner member 3550 can then be translated proximally relative to the outer sheath member 3510 to deploy the flexible elongate tube 3000 into the opening in the target tissue. FIG. 36B shows that the distal end 3588 of the elongate tube engagement component 3580 can be retracted into the lumen 3518 of the outer sheath member 3510. For example, the shaft 3556 of the inner member 3550 can be translated proximally within the lumen 3518 of the outer member 3510 such that distal end 3588 of the elongate tube engagement component 3580 is positioned within the lumen 3518 of the outer member 3510. The outer sheath member 3510 can be maintained in position, such as by maintaining the ridge 3340 against the first surface of the target tissue, while the inner member 3550 is retracted. The flexible elongate tube 3000 can remain positioned within the opening in the target tissue after the inner member 3550 is retracted, leaving the plurality of tethers 3450 extending through the lumen 3014 of the flexible elongate tube 3000. The inner member 3550 can be translated proximally until it is slid off of the plurality of tethers 3450. The outer sheath member 3510 can be removed from its position on the target tissue. The plurality of tethers 3450 can be left extending through the distal opening 3012 at the distal end 3008 of the flexible elongate tube 3000, through the lumen 3014 and the proximal opening 3010 of the lumen 3014 of the flexible elongate tube 3000.

As described herein, in some cases, the target tissue can be heart wall tissue, such as ventricular heart wall tissue. The opening can be formed in a left ventricular heart wall tissue to permit access to one or more heart valve leaflets. For example, the first surface can be an externally oriented surface of the left ventricular wall. In some cases, the second surface can be a surface of the left ventricular wall oriented toward the left ventricle.

Figure 37B:
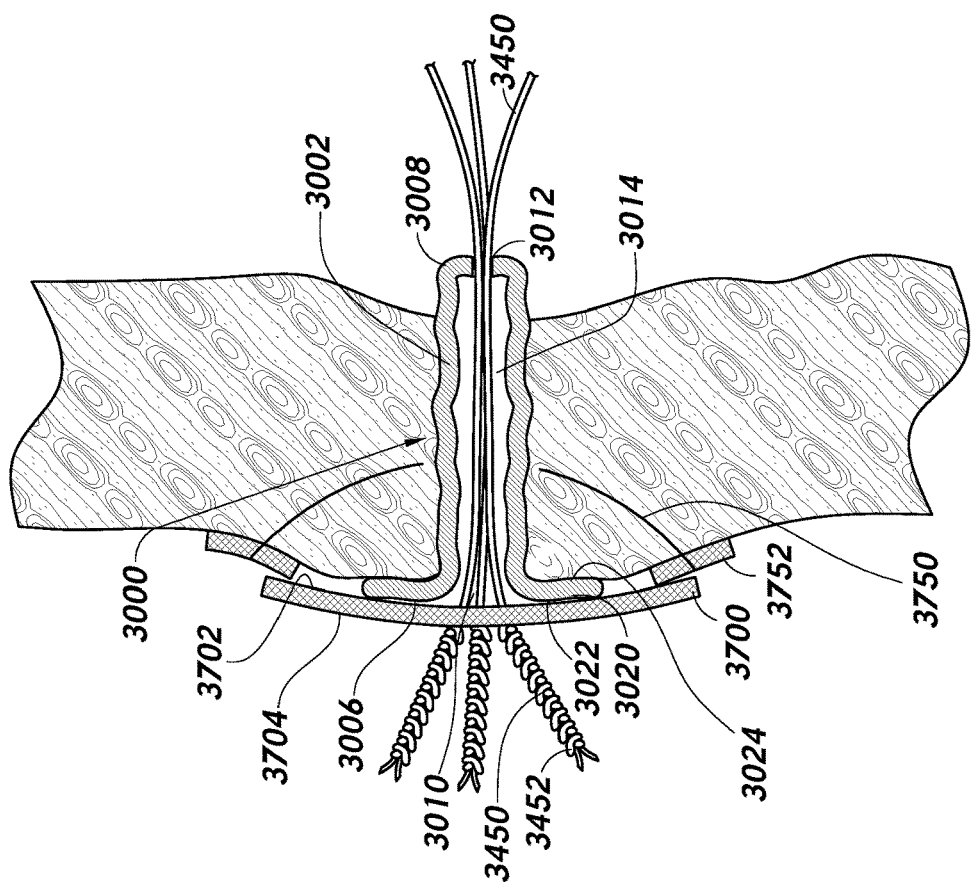
FIGS. 37A and 37B are cross-sectional views of the flexible elongate tube described with reference to FIG. 30 positioned within a target opening.
Figure 37A:
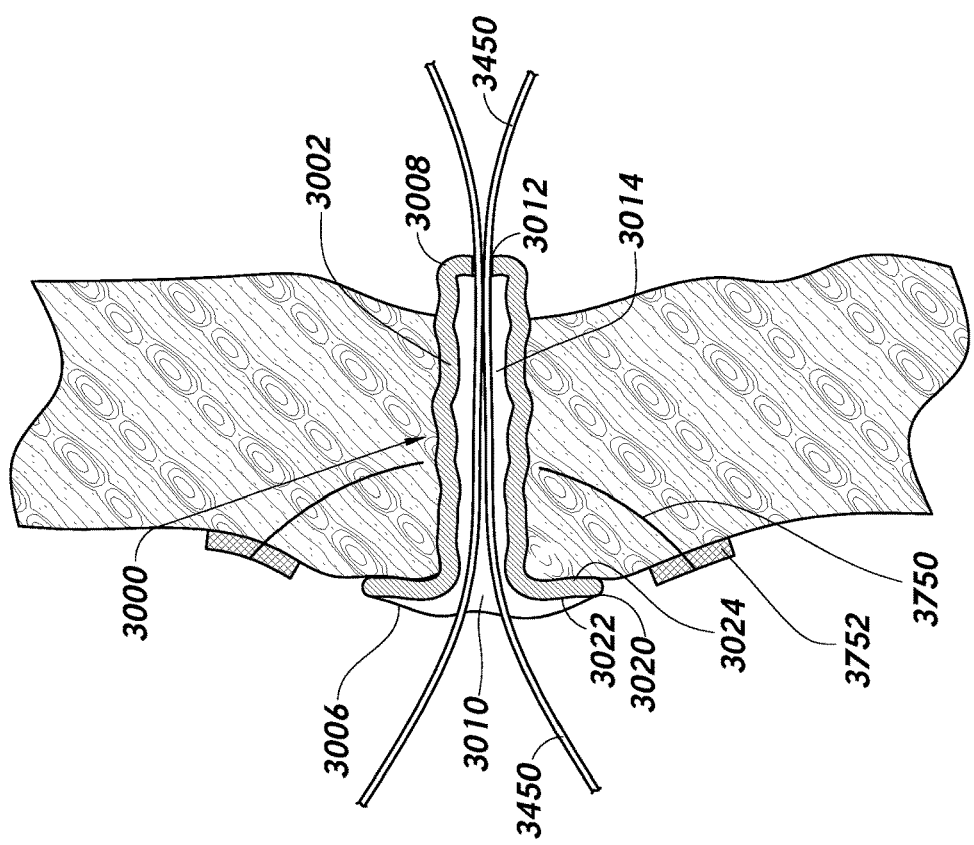

FIG. 37A is a cross-sectional view of the flexible elongate tube 3000 positioned within an opening in a target tissue. FIG. 37B is a cross-sectional view of a pad 3700 deployed over the flange 3020 of the flexible elongate tube 3000 while the flexible elongate tube 3000 is positioned within the opening. Portions of a plurality of tethers 3450 extending through the opening in the target tissue can extend through the pad 3700. Referring to FIG. 37A, a plurality of tethers 3450 can extend through the lumen 3014 of the flexible elongate tube 3000. The plurality of tethers 3450 can extend through the proximal opening 3010 of the lumen 3014 at the proximal end 3006 of the flexible elongate tube 3000, and through the distal opening 3012 at the distal end 3008 of the flexible elongate tube 3000. The flexible elongate tube 3000 can be collapsed around the plurality of tethers 3450. The elongate portion 3002 can be collapsed around a longitudinal axis of the flexible elongate tube 3000 due to force exerted thereupon by the target tissue. For example, a purse-string suture 3750 formed around the opening in the target tissue can be tensioned to push the target tissue together and close the opening around the flexible elongate tube 3000 and the plurality of tethers 3450. In some cases, a plurality of pads 3752 can be used to form the purse-string suture 3750 to reduce or eliminate abrasion of the target tissue caused by the purse-string suture 3750. The target tissue can thereby push against the flexible elongate tube 3000 to collapse the elongate portion 3002 around the plurality of tethers 3450. The flexible elongate tube 3000 can be positioned within the opening such that the flange 3020, such as the distal surface 3024 of the flange 3020, is positioned against a first surface of the target tissue. The distal end 3008 of the flexible elongate tube 3000 can be proximate or adjacent to the second surface of the target tissue. In some cases, the distal end 3008 can be flush or substantially flush with the second surface of the target tissue.

In FIG. 37B, the pad 3700 is positioned over at least a portion of the flexible elongate tube 3000 protruding from the opening over the first surface of the target tissue. For example, the pad 3700 can be positioned against the proximal surface 3022 of the flange 3020. The plurality of tethers 3450 can be secured to the pad 3700. In some cases, portions of the plurality of tethers 3450 can be extended through the pad 3700 to facilitate securement to the pad 3700. For example, the plurality of tethers can be threaded through the pad 3700 from a first surface 3702 oriented toward the target tissue to a second surface 3704 oriented away from the target tissue. The first surface 3702 can be in contact with the proximal surface 3222 of the flange 3220. Portions of the plurality of tethers 3450 extending externally from the pad 3700 can be secured to the pad 3700 after desired tension in the tethers 3450 have been achieved, facilitating maintaining the tension in the tethers 3450. In some cases, knots 3452 can be formed using the portions of the plurality of tethers 3450 extending externally from the second surface 3704 of the pad 3700. Securing the plurality of tethers 3450 to the pad 3700 can facilitate stable positioning of the pad 3700 against the flange 3020 and/or target tissue.

Figures 38A, 38B:
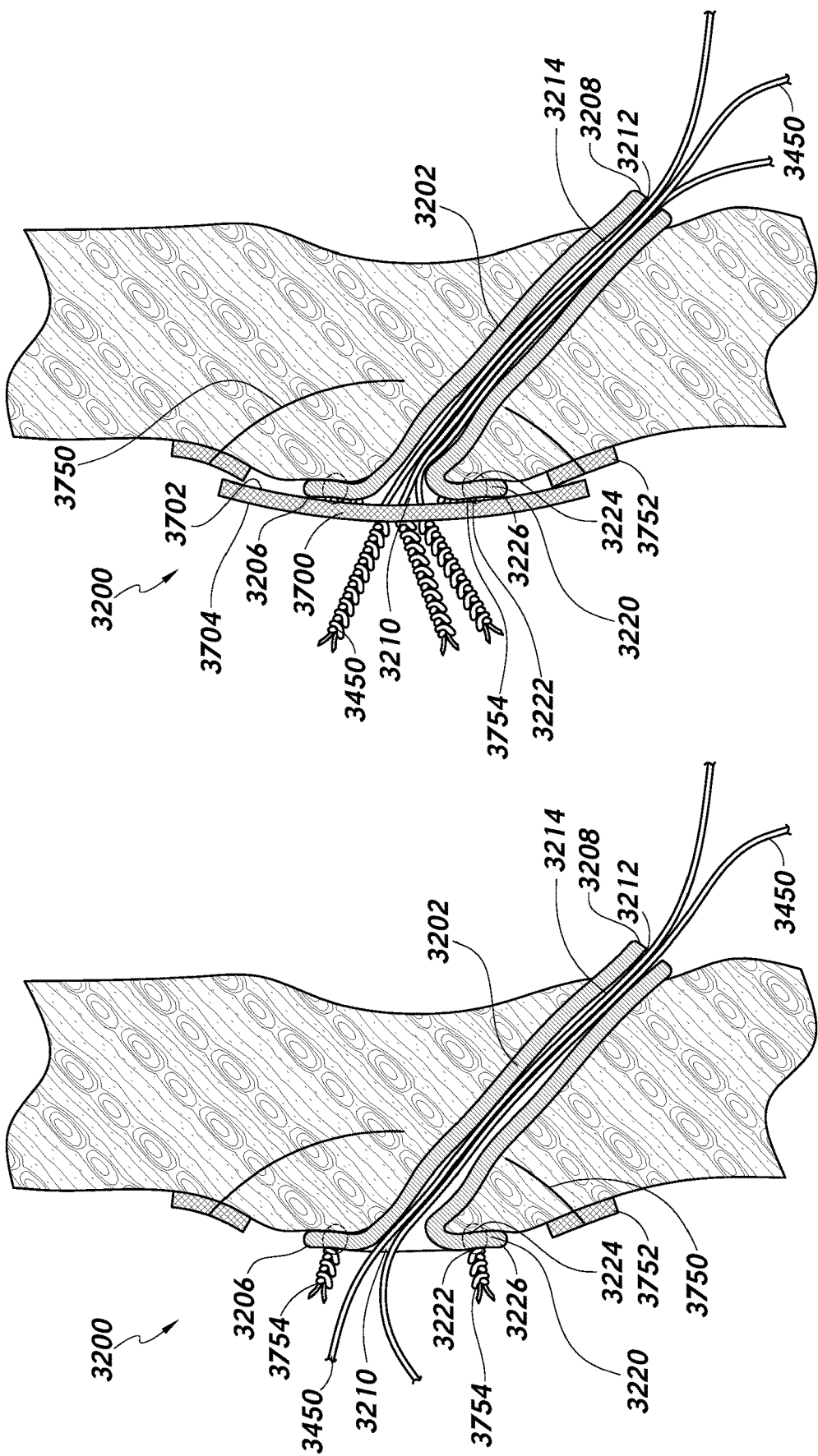
FIGS. 38A and 38B are cross-sectional views of the flexible elongate tube described with reference to FIG. 32 positioned within a target opening.

FIG. 38A is a cross-sectional view of the flexible elongate tube 3200 positioned within an opening in a target tissue, and FIG. 38B is a cross-sectional view of a pad 3700 deployed over the flange 3220 of the flexible elongate tube 3200 while the flexible elongate tube 3200 is positioned within the opening. Referring to FIG. 38A, a plurality of tethers 3450 can extend through the lumen 3214 of the flexible elongate tube 3200, the plurality of tethers 3450 extending through the proximal opening 3210 of the lumen 3214 at the proximal end 3206 of and the distal opening 3212 at the distal end 3208 of the flexible elongate tube 3200. The purse-string suture 3750 can be tensioned to close the opening in the target tissue around the plurality of tethers 3450 and the flexible elongate tube 3200. The elongate portion 3202 of the flexible elongate tube 3200 can be collapsed around the plurality of tethers 3450 due to tensioning of the purse-string suture 3750. A plurality of pads 3752 can be used to form the purse-string suture 3750 to reduce or eliminate abrasion of the target tissue caused by the purse-string suture 3750. The flexible elongate tube 3200 can be positioned within the opening such that the flange 3220, such as the distal surface 3224 of the flange 3020, is positioned against a first surface of the target tissue. The distal end 3208 of the flexible elongate tube 3200 can be proximate or adjacent to the second surface of the target tissue. In some cases, the distal end 3208 can be flush or substantially flush with the second surface of the target tissue.

One or more anchors 3754 (e.g., one or more sutures) can couple the reinforced portion 3226 of the flange 3220 to the target tissue. Anchoring the flange 3220 to the target tissue can improve secure placement of the flexible elongate tube 3200 within the opening. The reinforced portion 3226 can provide desired strength to withstand extension therethrough of the one or more anchors 3754. For example, anchoring the flange 3220 to the target tissue can be advantageous for secure positioning of the flexible elongate tube 3200 within openings which are at an angle other than a right angle relative to one or more surfaces of the adjacent target tissue, such as openings which extend at a slant into the target tissue.

Referring to FIG. 37B, the pad 3700 can be positioned over at least a portion of the flexible elongate tube 3200 protruding from the opening over the first surface of the target tissue, such as the proximal surface 3222 of the flange 3220. The plurality of tethers 3450 can be secured to the pad 3700. Portions of the plurality of tethers 3450 extending externally from the pad 3700 can be secured to the pad 3700 after desired tension in the tethers 3450 have been achieved. In some cases, portions of the plurality of tethers 3450 can be extended through the pad 3700 to facilitate securement to the pad 3700. For example, the plurality of tethers can be threaded through the pad 3700 from a first surface 3702 oriented toward the target tissue to a second surface 3704 oriented away from the target tissue. The first surface 3702 can be in contact with the proximal surface 3222 of the flange 3220. Knots 3452 can be formed using the portions of the plurality of tethers 3450 extending from the pad 3700. In some cases, anchors 3754 coupled to the reinforced portion 3226 of the flange 3220 can be trimmed prior to positioning the pad 3700 over the flange 3220. In some cases, the pad 3700 can be positioned over the flange 3220 without trimming the anchors 3754.

Figure 39:
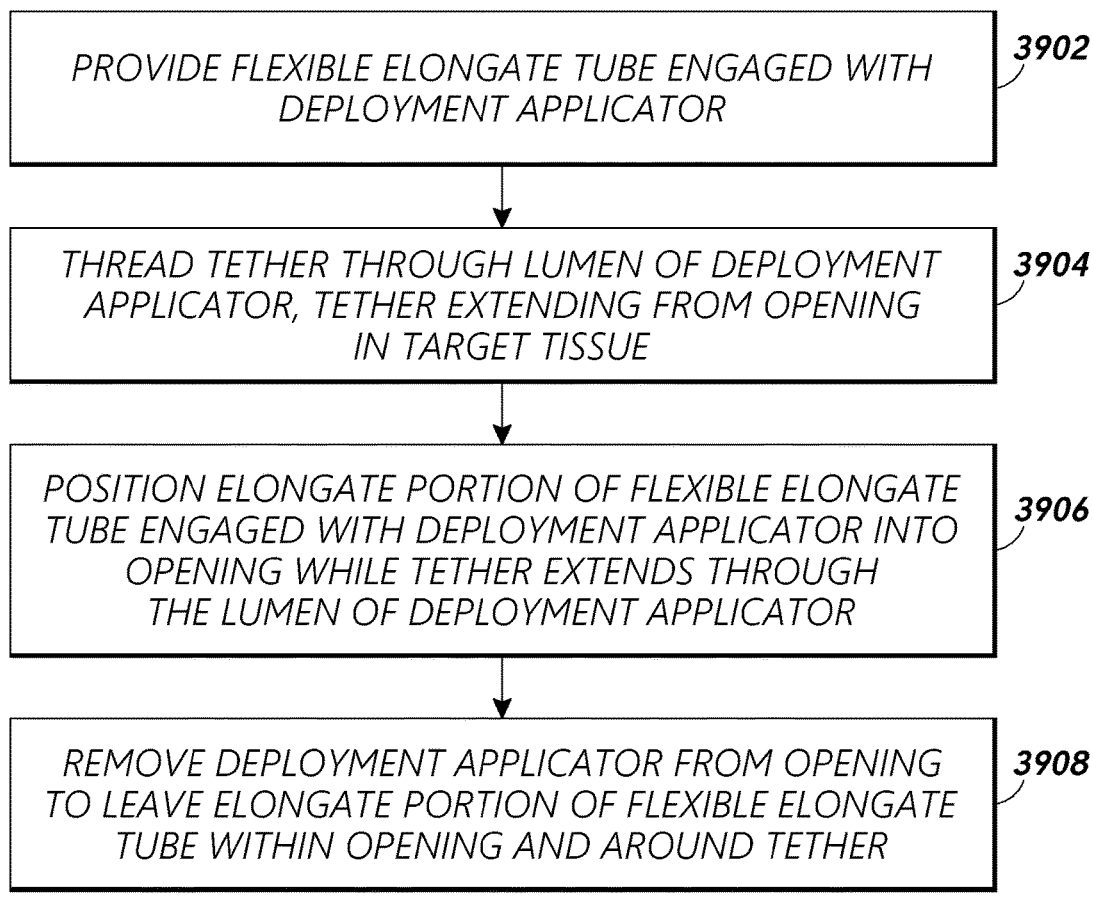
FIG. 39 is a process flow diagram of an example of a process to deploy a flexible elongate tube for positioning around portions of one or more tethers extending through a target opening.

FIG. 39 is a process flow diagram of an example of a process 3900 for deploying a protective sleeve, the protective sleeve comprising one or more features as described herein. In block 3902, the process 3900 can involve providing a flexible elongate tube engaged with a deployment applicator. The flexible elongate tube can comprise a lumen extending therethrough. The deployment applicator can comprise an elongate tube engagement component associate with a distal portion such that the engagement component is configured to be received within the lumen of the flexible elongate tube.

In block 3904, the process 3900 can involve threading a tether through the lumen of the deployment applicator, the tether extending from an opening in a target tissue. In block 3906, the process 3900 can involve positioning an elongate portion of the flexible elongate tube engaged with the deployment applicator into the opening in the target tissue while the tether extends through the lumen of the deployment applicator. The flexible elongate tube can be received around the engagement component of the deployment applicator. The elongate portion received around the engagement component can be positioned into the opening in the target tissue while the tether extends through the lumen of the deployment applicator. In some cases, the flexible elongate tube can be pre-seated over the elongate tube engagement component of the deployment applicator. In some cases, the flexible elongate tube can be positioned over the elongate tube engagement component of the deployment applicator. In block 3908, the process can involve removing the deployment applicator from the opening to leave the elongate portion of the flexible elongate tube within the opening and around the tether. The elongate portion of the flexible elongate tube can be collapsed within the opening around a longitudinal axis of the flexible elongate tube. The flexible elongate tube can be collapsed around the tether.

As described herein, the flexible elongate tube can comprise an elongate portion and a flange around a proximal end of the elongate portion. In some cases, positioning the predetermined portion of the flexible elongate tube received around the engagement component into the opening comprises positioning the flange of the flexible elongate tube against the target tissue. In some cases, a proximal portion of the elongate tube engagement component can comprise a ridge around a circumference thereof. Positioning the flexible elongate tube over the elongate tube engagement component can comprise positioning a proximal surface of the flange against a distal surface of the ridge.

In some cases, the deployment applicator can comprise an inner member and an outer sheath member. The elongate tube engagement component can be associated with a distal portion of the inner member. The outer sheath member comprising an outer sheath lumen extending therethrough. A portion of the inner member can be slidably received within the outer sheath lumen. In some cases, deploying the flexible elongate tube into the opening in the target tissue can comprise advancing the distal portion of the inner member comprising the elongate tube engagement component associated therewith into the opening, and proximally displacing the inner member relative to the outer sheath member. The inner member can be proximally displaced until the flexible elongate tube is removed from around the elongate tube engagement component. The inner member can be proximally displaced while contact between the outer sheath member and a portion of the flexible elongate tube extending externally of the opening is maintained such that the flexible elongate tube remains in the opening.

In some cases, the outer sheath member can comprise a ridge associated with a distal portion. Deploying the flexible elongate tube can comprise contacting the ridge of the outer sheath member and the portion of the flexible elongate tube extending externally of the opening to maintain the flexible elongate tube in the opening. The flexible elongate tube can comprise a flange around a proximal end, and contacting the ridge of the outer sheath member and the portion of the flexible elongate tube extending externally of the opening can comprise contacting the ridge of the outer sheath member and the flange.

Additional Cases

Depending on the embodiment, certain acts, events, or functions of any of the processes or algorithms described herein can be performed in a different sequence, may be added, merged, or left out altogether. Thus, in certain cases, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain cases include, while other cases do not include, certain features, elements and/or steps. Thus, such conditional language is not generally intended to imply that features, elements and/or steps are in any way required for one or more cases or that one or more cases necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain cases require at least one of X, at least one of Y and at least one of Z to each be present.

It should be appreciated that in the above description of cases, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular cases described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example cases belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A suture system, comprising:
   a first and a second curved double arm needle;
   a needle docking device configured to maintain the first and the second curved double arm needles in alignment with and parallel to one another and at predetermined orientations relative to the needle docking device; and
   a needle manipulating instrument comprising a distal portion configured to engage the first and the second curved double arm needles while the first and second curved double arm needles are in the needle docking device, and to maintain the needles in alignment with and parallel to one another and at a predetermined orientation relative to the needle manipulating instrument.

2. The system of claim 1, wherein the distal portion of the needle manipulating instrument is configured to maintain the needles in alignment with and parallel to one another and at the predetermined orientation relative to the needle manipulating instrument while the needles are removed from the needle docking device.

3. The system of claim 1, wherein the needle docking device comprises:
   a first wall portion comprising a first pair of openings sized to allow extension therethrough of first respective portions of the first and second curved double arm needles; and
   a second wall portion spaced from the first wall portion, the second wall portion comprising a second pair of openings sized to allow extension therethrough of second respective portions of the first and second curved double arm needles,
   wherein a distance between the first pair of openings and a distance between the second pair of openings are predetermined to provide a predetermined distance between the first and second curved double arm needles.

4. The system of claim 3, wherein a cross-sectional size of each of the first and second curved double arm needles vary along a respective length of the needles, and wherein a size of the first pair of openings and a size of the second pair of openings are configured to allow a predetermined length of the first and the second curved double arm needles to extend through the docking device.

5. The system of claim 3, wherein the needle docking device comprises a solid configuration.

6. The system of claim 5, wherein the docking device comprises a first lumen extending between corresponding openings on the first wall portion and the second wall portion for receiving the first curved double arm needle and a second lumen extending between corresponding openings on the first wall portion and the second wall portion for receiving the second curved double arm needle, wherein the first lumen and the second lumen each comprises engagement features configured to engage with the first and second curved double arm needles to maintain a predetermined orientation of the needles.

7. The system of claim 1, wherein the needle manipulating instrument comprises a surgical clamp, the surgical clamp comprising:
   a first arm pivotally coupled to a second arm;
   a first handle and a second handle associated with respective proximal portions of the first arm and the second arm; and
   a first distal portion of the first arm and a second distal portion of the second arm being configured to be pivoted toward one another to engage the first and the second curved double arm needles,
   wherein the first and second distal portions comprise a first curvature and a second curvature, respectively, wherein the first arm comprises a portion distal of the first curvature extending along a first axis which is perpendicular to that along which a portion proximal of the first curvature extends, and wherein the second arm comprises a portion distal of the second curvature extending along a second axis which is perpendicular to that along which a portion proximal of the second curvature extends, and
   wherein at least one of the portion of the first arm distal of the first curvature and the portion of the second arm distal of the second curvature comprises a first recess and a second recess on a surface oriented toward the other arm, the first and the second recesses being configured to receive the first and the second curved double arm needles.

8. The system of claim 7, wherein a length of each of the first arm and the second arm can be adjustable.

9. The system of claim 7, wherein the first distal portion and the second distal portion are configured to pivot toward one another to position the first and the second curved double arm needles within corresponding first and second recesses and maintain the first and the second curved double arm needles at a predetermined distance from one another.

10. The system of claim 7, wherein, while the first and second curved double arm needles are held by the surgical clamp, the first and second curved double arm needles are parallel to the portion of the first arm proximal of the first curvature and the portion of the second arm proximal of the second curvature, and wherein sharp ends of the first and the second curved double arm needles are aligned with one another and positioned distally of the surgical clamp.

11. The system of claim 7, wherein a cross-sectional size of each of the first and second curved double arm needles vary along a respective length of the needles, and wherein a width of the first recess and the second recess are configured to allow a predetermined length of the first and the second curved double arm needles to be positioned within the first and second recesses.

12. The system of claim 1, wherein the needle manipulating instrument comprises:
   a proximal handle; and
   a shaft portion extending distally from the proximal handle, a distal portion of the shaft portion comprising a first and a second lumen extending to a distal end of the shaft portion and a respective needle engagement feature within each of the first and second lumens, wherein the respective needle engagement feature extends from a corresponding lumen wall and is configured to engage with a respective proximal portion of the first or second curved double arm needle positioned within the lumen.

13. The system of claim 12, wherein the shaft portion comprises a first and a second shaft extending distally from the proximal handle, wherein the first shaft comprises the first lumen and the second shaft comprises the second lumen.

14. The system of claim 12, wherein the shaft portion comprises a curvature.

15. The system of claim 12, wherein the shaft portion is linear.

16. The system of claim 12, wherein respective proximal portions of the first and second curved double arm needles are coupled to a suture, and wherein respective portions of the suture are received within the first lumen and the second lumen.

17. The system of claim 12, wherein wall portions of the shaft portion defining the first lumen and the second lumen comprise respective openings to allow extension therethrough of a suture portion coupled to the respective proximal portions of the first and second curved double arm needles, the respective openings to the distal end of the shaft portion.

* * * * *